(12) United States Patent
Brueggemeier et al.

(10) Patent No.: US 10,611,765 B2
(45) Date of Patent: Apr. 7, 2020

(54) PYRROLOPYRIMIDINE DERIVATIVES AS MPS1/TTK KINASE INHIBITORS

(71) Applicant: Ohio State Innovation Foundation, Columbus, OH (US)

(72) Inventors: Robert Brueggemeier, Dublin, OH (US); Harold Fisk, Dublin, OH (US); Pui-Kai Li, Dublin, OH (US); Chenglong Li, Dublin, OH (US); Yasuro Sugimoto, Dublin, OH (US)

(*) Notice: Subject to any disclaimer, the term of this patent is extended or adjusted under 35 U.S.C. 154(b) by 246 days.

(21) Appl. No.: 15/524,606

(22) PCT Filed: Nov. 5, 2015

(86) PCT No.: PCT/US2015/059312
§ 371 (c)(1),
(2) Date: May 4, 2017

(87) PCT Pub. No.: WO2016/073771
PCT Pub. Date: May 12, 2016

(65) Prior Publication Data
US 2019/0106422 A1    Apr. 11, 2019

Related U.S. Application Data

(60) Provisional application No. 62/076,434, filed on Nov. 6, 2014.

(51) Int. Cl.
*C07D 487/04* (2006.01)
*C07D 471/04* (2006.01)
*A61P 35/00* (2006.01)

(52) U.S. Cl.
CPC ......... *C07D 487/04* (2013.01); *C07D 471/04* (2013.01); *A61P 35/00* (2018.01)

(58) Field of Classification Search
CPC .................... C07D 487/04; C07D 471/04
USPC ....................................... 544/280
See application file for complete search history.

(56) References Cited

U.S. PATENT DOCUMENTS

| | | | |
|---|---|---|---|
| 2012/0015937 | A1 | 1/2012 | Ding et al. |
| 2013/0303534 | A1 | 11/2013 | Ibrahim et al. |
| 2013/0345101 | A1 | 12/2013 | Imai et al. |
| 2014/0200206 | A1 | 7/2014 | Calabrese et al. |

FOREIGN PATENT DOCUMENTS

| | | | | |
|---|---|---|---|---|
| WO | WO-2009/032694 A1 | 3/2009 | | |
| WO | WO-2009032703 A1 | * | 3/2009 | ........... C07D 239/50 |

OTHER PUBLICATIONS

Bursavich, Matthew G. et al., "Novel Mps1 kinase inhibitors: From purine to pyrrolopyrimidine and quinazoline leads", Bioorganic & Medicinal Chemistry Letters 23 (2013)6829-6833, 5 pages.
Daniel, Jewel et al., "High levels of the Mps1 checkpoint protein are protective of aneuploidy cancer cells", Proceedings of the National Academy of Sciences, vol. 108 No. 13, Mar. 29, 2011, 12 pages.
International Search Report and Written Opinion for corresponding International Patent Application No. PCT/US2015/059312, dated May 16, 2016, 12 pages.

* cited by examiner

*Primary Examiner* — Kahsay Habte
(74) *Attorney, Agent, or Firm* — Foley & Lardner LLP; Antoinette F. Konski; Alice Lee-Dutra

(57) ABSTRACT

Disclosed herein are novel compounds that are Mps1/TTK inhibitors. Also disclosed are compositions comprising the compounds and methods of using the compounds in treating various diseases.

14 Claims, 7 Drawing Sheets

A

DMSO (Control)

Cmpd-13

B

C

| Mouse # | Starting weight (grams) | Week 5 weight (grams) |
|---|---|---|
| Mouse 1 | 25 | 24 |
| Mouse 2 | 21 | 21 |
| Mouse 3 | 22 | 23 |
| Mouse 4 | 22 | 23 |
| Mouse 5 | 25 | 24 |

PYRROLOPYRIMIDINE DERIVATIVES AS MPS1/TTK KINASE INHIBITORS

CROSS-REFERENCE TO RELATED APPLICATIONS

This application is a national stage application under 35 U.S.C. § 371 of International Application No. PCT/US2015/059312, filed on May 19, 2015, which in turn claims priority under 35 U.S.C § 119(e) of U.S. Provisional Application No. 62/076,434, filed Nov. 6, 2014, the content of each of which is incorporated by reference in its entirety into the current disclosure.

STATEMENT OF GOVERNMENT SUPPORT

The presently disclosed subject matter was made in part with United States Government support under Grant Nos. UL1 RR025755(TR00090), 1UL1TR001070 and GM07731, each awarded by the National Institutes of Health. Accordingly, the United States Government has certain rights in the presently disclosed subject matter.

BACKGROUND

Breast cancer is a heterogeneous group of tumors which can be subdivided on the basis of histopathological features, genetic alterations, and gene-expression profiles (1; 2). Approximately 50-60% of all breast cancer patients and two-thirds of postmenopausal breast cancer patients have estrogen receptor positive tumors (ER+). Adjuvant hormonal therapy is the primary therapy for ER+ breast cancer. TNBC is defined by the absence of staining for estrogen receptors, progesterone receptors, and HER2/neu. These tumors have poor clinical outcome and represent a recognized prognostic group characterized by aggressiveness (3) and resistance to available systemic therapy. Approximately 10-25% of all breast cancers in the U.S. are TNBC.

Current therapies for certain subtypes of breast cancer (BC), such as triple negative BC (TNBC) and other aggressive phenotypes, rely on standard chemotherapy approaches with significant side effects; therefore, newer targeted therapy approaches are needed.

SUMMARY

Disclosed herein are Mps1/TTK kinase inhibitory compounds, compositions, and uses thereof.

In one aspect, provided herein are compounds of Formula IV-A or V-A:

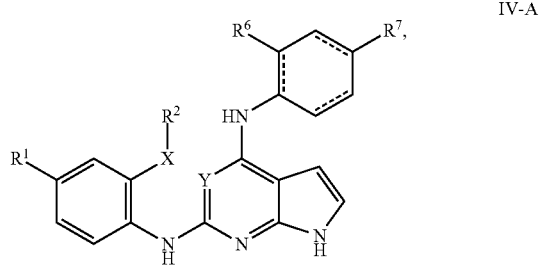

IV-A

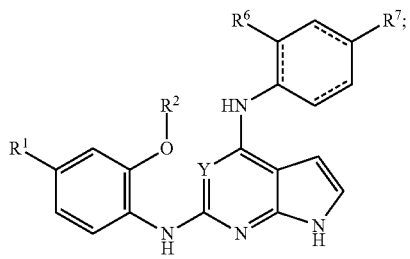

V-A or a tautomer, a pharmaceutically acceptable salt and/or a solvate thereof;
wherein
X is O, S or $SO_2$;
Y is CH or N;
$R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —C(O)O—$R^{10}$, —$NR^{10}R^{11}$, —C(O)$NR^{10}R^{11}$, —C(S)$NR^{10}R^{11}$, —$NR^{13}C(O)NR^{10}R^{11}$, —$NR^{13}C(S)NR^{10}R^{11}$, —O—C(O)$NR^{10}R^{11}$, —S(O)$_2NR^{10}R^{11}$, —O—S(O)$_2NR^{10}R^{11}$, —$NR^{13}$—S(O)$_2NR^{10}R^{11}$, CN, halo, $NO_2$, and —S(O)$_2$—$R^{12}$;
$R^2$ is selected from the group consisting of hydrogen, $C_1$-$C_3$ alkyl and $C_1$-$C_3$ haloalkyl; provided that when X is $SO_2$, or when $R^1$ is hydrogen, then $R^2$ is not hydrogen;
$R^6$ is selected from the group consisting of hydrogen, halo, —O—$R^{20}$, —C(O)—$R^{20}$, —C(O)O—$R^{20}$, —$NR^{20}R^{21}$, —C(S)$NR^{20}R^{21}$, —$NR^{23}C(O)NR^{20}R^{21}$, —$NR^{23}C(S)NR^{20}R^{21}$, —O—C(O)$NR^{20}R^{21}$, —S(O)$_2NR^{20}R^{21}$, —O—S(O)$_2NR^{20}R^{21}$, —$NR^{23}$—S(O)$_2NR^{20}R^{21}$, CN, $NO_2$, $C_1$-$C_6$ alkyl and —S(O)$_2$—$R^{22}$;
$R^7$ is selected from the group consisting of hydrogen, halo, —O—$R^{20}$, —C(O)—$R^{20}$, —C(O)O—$R^{20}$, —$NR^{20}R^{21}$, —C(O)$NR^{20}R^{21}$, —C(S)$NR^{20}R^{21}$, —$NR^{23}C(O)NR^{20}R^{21}$, —$NR^{23}C(S)NR^{20}R^{21}$, —O—C(O)$NR^{20}R^{21}$, —S(O)$_2NR^{20}R^{21}$, —O—S(O)$_2NR^{20}R^{21}NR^{23}$—S(O)$_2NR^{20}R^{21}$, CN, $NO_2$, $C_1$-$C_6$ alkyl and —S(O)$_2$—$R^{22}$;
each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle; or $R^{20}$ and $R^{21}$ together with the atom attached thereto form a 5- to 7-membered heterocycle;
each of $R^{12}$ and $R^{22}$ is independently $C_1$-$C_6$ alkyl; and
==== represents a single bond or a double bond.

In some embodiments, $R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —C(O)O—$R^{10}$, —$NR^{10}R^{11}$, —C(O)$NR^{10}R^{11}$, —$NR^{13}C(O)NR^{10}R^{11}$, —O—C(O)$NR^{10}R^{11}$, —$NR^{13}$—S(O)$_2NR^{10}R^{11}$, CN, halo, and —S(O)$_2$—$R^{12}$. In some embodiments, $R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —$NR^{10}R^{11}$, —$NR^{13}C(O)NR^{10}R^{11}$, —O—C(O)$NR^{10}R^{11}$, and —$NR^{13}$—S(O)$_2NR^{10}R^{11}$. In some embodiments, $R^1$ is selected from the group consisting of hydrogen and 5- to 7-membered heterocycle optionally substituted with one or two $R^3$, wherein $R^3$ is independently selected from the group consisting of —O—$R^{10}$ and —O—C(O)$NR^{10}R^{11}$. In some embodiments, $R^1$ is hydrogen. In some embodiments, $R^1$ is a 5- to 7-membered heterocycle substituted with one or two $R^3$, wherein $R^3$ is independently selected from the group consisting of —O—$R^{10}$ and —O—C(O)N$R^{10}R^{11}$. In some embodiments, $R^1$ is a 5- to 7-membered heterocycle. In some embodiments, $R^6$ is selected from the group consisting of hydrogen, halo, —O—$R^{20}$, —C(O)—$R^{20}$, —C(O)O—$R^{20}$, —N$R^{20}R^{21}$, —N$R^{23}$C(O)N$R^{20}R^{21}$, —O—C(O)N$R^{20}R^{21}$, —S(O)$_2$N$R^{20}R^{21}$, CN, $C_1$-$C_6$ alkyl and —S(O)$_2$—$R^{22}$. In some embodiments, $R^6$ is selected from the group consisting of hydrogen, halo, —C(O)—$R^{20}$, —C(O)O—$R^{20}$, —S(O)$_2$N$R^{20}R^{21}$, CN, and —S(O)$_2$—$R^{22}$. In some embodiments, $R^6$ is selected from the group consisting of hydrogen, and —S(O)$_2$—$R^{22}$. In some embodiments, $R^7$ is selected from the group consisting of hydrogen, halo, —C(O)—$R^{20}$, —C(O)O—$R^{20}$, —C(O)N$R^{20}R^{21}$, —S(O)$_2$N$R^{20}R^{21}$, CN, NO$_2$, and —S(O)$_2$—$R^{22}$. In some embodiments, $R^7$ is selected from the group consisting of hydrogen, halo, —C(O)—$R^{20}$, —C(O)O—$R^{20}$, —C(O)N$R^{20}R^{21}$, and CN. In some embodiments, $R^7$ is selected from the group consisting of hydrogen, and —C(O)N$R^{20}R^{21}$. In some embodiments, X is O. In some embodiments, X is S. In some embodiments, X is SO$_2$. In some embodiments, Y is N. In some embodiments, Y is CH. In some embodiments, the compound is of Formula VI, or a tautomer, a pharmaceutically acceptable salt and/or a solvate thereof. In some embodiments, the compound is of Formula VII, or a tautomer, a pharmaceutically acceptable salt and/or a solvate thereof. In some embodiments, the compound is of Formula VIII, or a tautomer, a pharmaceutically acceptable salt and/or a solvate thereof.

In one aspect, provided herein are compounds of Formula IV-A, IV-B, IV-C, V-A, V-B, or V-C:

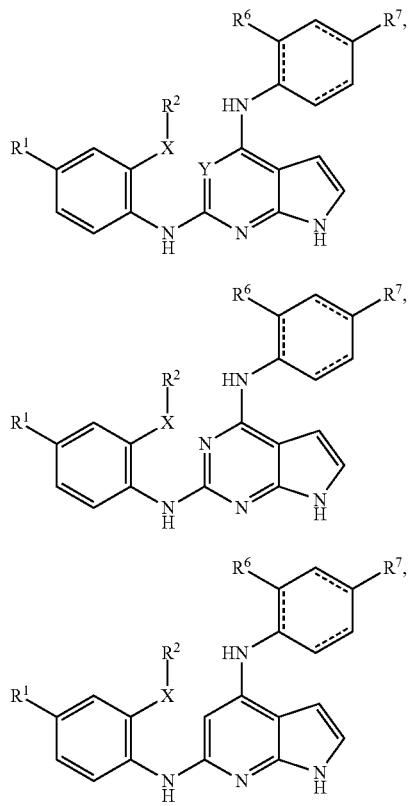

IV-A

IV-B

IV-C

-continued

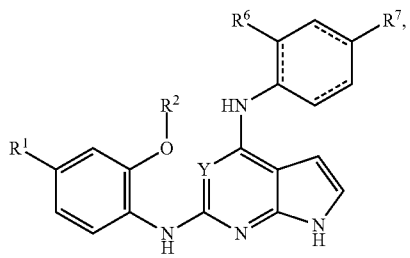

V-A

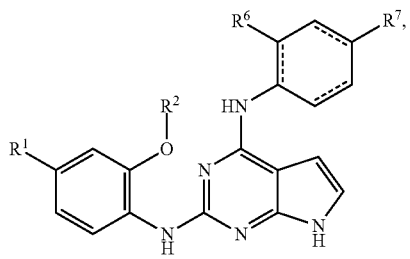

V-B

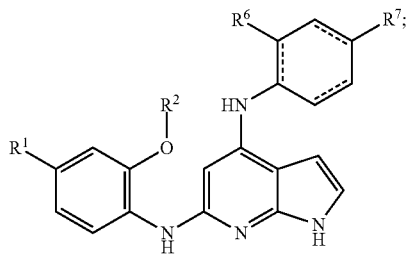

V-C or a tautomer, a pharmaceutically acceptable salt and/or a solvate thereof;

wherein

X is O, S or SO$_2$;

Y is CH or N;

$R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —N$R^{10}$C(O)$R^{12}$, —C(O)O—$R^{10}$, —N$R^{10}R^{11}$, —C(O)N$R^{10}R^{11}$, —C(S)N$R^{10}R^{11}$, —N$R^{13}$C(O)N$R^{10}R^{11}$, —N$R^{13}$C(S)N$R^{10}R^{11}$, —O—C(O)N$R^{10}R^{11}$, —S(O)$_2$N$R^{10}R^{11}$, —O—S(O)$_2$N$R^{10}R^{11}$, —N$R^{13}$—S(O)$_2$N$R^{10}R^{11}$, CN, halo, NO$_2$, and —S(O)$_2$—$R^{12}$;

$R^2$ is selected from the group consisting of hydrogen, $C_1$-$C_3$ alkyl and $C_1$-$C_3$ haloalkyl; provided that when X is SO$_2$, or when $R^1$ is hydrogen, then $R^2$ is not hydrogen;

$R^6$ is selected from the group consisting of hydrogen, halo, —O—$R^{20}$, —C(O)—$R^{20}$, —C(O)O—$R^{20}$, —N$R^{20}R^{21}$, —C(S)N$R^{20}R^{21}$, —N$R^{23}$C(O)N$R^{21}R^{21}$, —N$R^{23}$C(S)N$R^{20}R^{21}$, —O—C(O)N$R^{20}R^{21}$, —S(O)$_2$N$R^{20}R^{21}$, —O—S(O)$_2$N$R^{20}R^{20}$, —N$R^{23}$—S(O)$_2$N$R^{20}R^{21}$, CN, NO$_2$, $C_1$-$C_6$ alkyl and —S(O)$_2$—$R^{22}$;

$R^7$ is selected from the group consisting of hydrogen, halo, —O—$R^{20}$, —C(O)—$R^{20}$, —C(O)O—$R^{20}$, —N$R^{20}R^{21}$, —C(O)N$R^{20}R^{21}$, —C(S)N$R^{20}R^{21}$, —N$R^{23}$C(O)N$R^{20}R^{21}$, —N$R^{23}$C(S)N$R^{20}R^{21}$, —O—C(O)N$R^{20}R^{21}$, —S(O)$_2$N$R^{20}R^{21}$, —O—S(O)$_2$N$R^{20}R^{21}$, —N$R^{23}$—S(O)$_2$ $R^{20}R^{21}$, CN, NO$_2$, $C_1$-$C_6$ alkyl and —S(O)$_2$—$R^{22}$;

each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle; or R²⁰ and R²¹ together with the atom attached thereto form a 5- to 7-membered heterocycle;
each of R¹² and R²² is independently $C_1$-$C_6$ alkyl; and
==== represents a single bond or a double bond.

In one aspect, provided herein are the following compounds

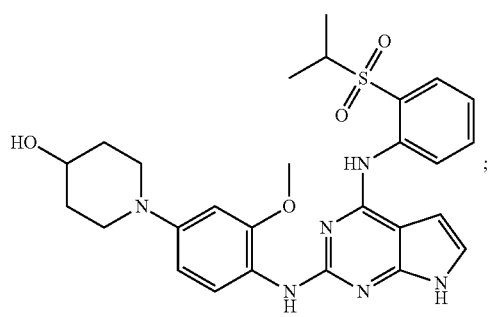

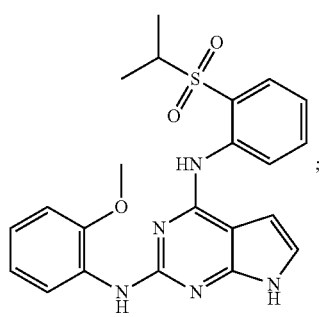

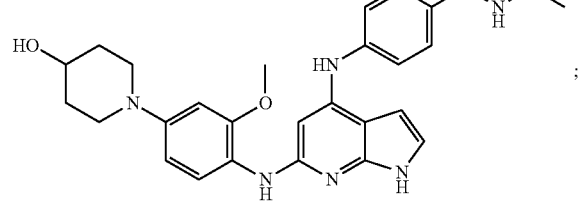

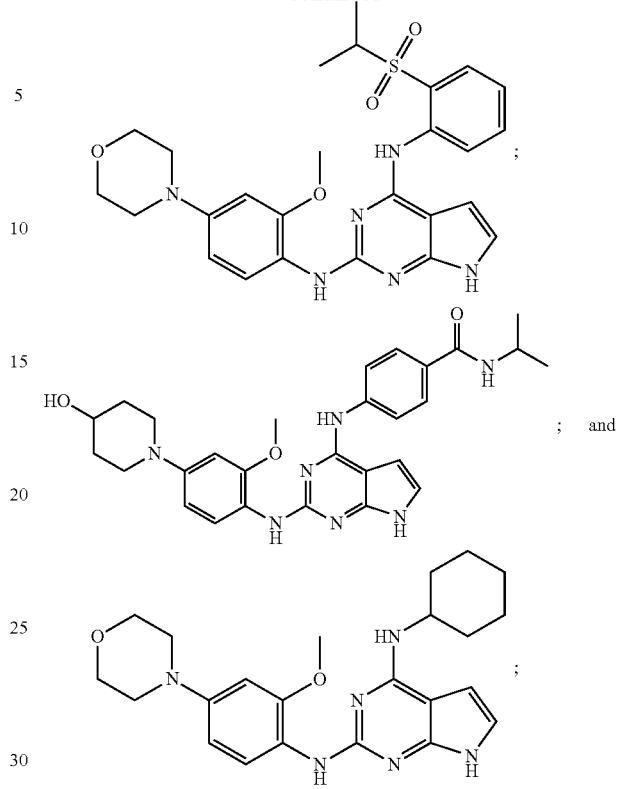

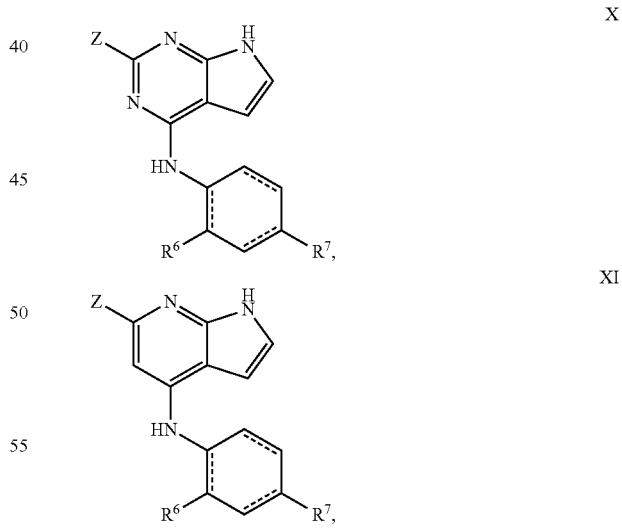

or a tautomer, a pharmaceutically acceptable salt and/or a solvate thereof.

In one aspect, provided herein are compounds of Formula X or XI:

or a tautomer, a pharmaceutically acceptable salt and/or a solvate thereof;
wherein
Z is chloro or bromo;
R⁶ is selected from the group consisting of hydrogen, halo, —O—R²⁰, —C(O)—R²⁰, —C(O)O—R²⁰, —NR²⁰R²¹, —C(S)NR²⁰R²¹, —NR²³C(O)NR²⁰R²¹, —NR²³C(S) NR²⁰R²¹, —O—C(O)NR²⁰R²¹, —S(O)₂NR²⁰R²¹, —O—S(O)$_2$NR$^{20}$R$^{21}$, —NR$^{23}$—S(O)$_2$NR$^{20}$R$^{21}$, CN, NO$_2$, C$_1$-C$_6$ alkyl and —S(O)$_2$—R$^{22}$;

R$^7$ is selected from the group consisting of hydrogen, halo, —O—R$^{20}$, —C(O)—R$^{20}$, —C(O)O—R$^{20}$, —NR$^{20}$R$^{21}$, —C(O)NR$^{20}$R$^{21}$, —C(S)NR$^{20}$R$^{21}$, —NR$^{23}$C(O) NR$^{20}$R$^{21}$, —NR$^{23}$C(S)NR$^{20}$R$^{21}$, —O—C(O)NR$^{20}$R$^{21}$, —S(O)$_2$NR$^{20}$R$^{21}$, —O—S(O)$_2$NR$^{20}$R$^{21}$, —NR$^{23}$—S(O)$_2$NR$^{20}$R$^{21}$, CN, NO$_2$, C$_1$-C$_6$ alkyl and —S(O)$_2$—R$^{22}$;

each of R$^{20}$, R$^{21}$, and R$^{23}$ is independently hydrogen or C$_1$-C$_6$ alkyl; or R$^{20}$ and R$^{21}$ together with the atom attached thereto form a 5- to 7-membered heterocycle;

R$^{22}$ is C$_1$-C$_6$ alkyl; and

==== represents a single bond or a double bond.

In one aspect, provided herein are the following compounds

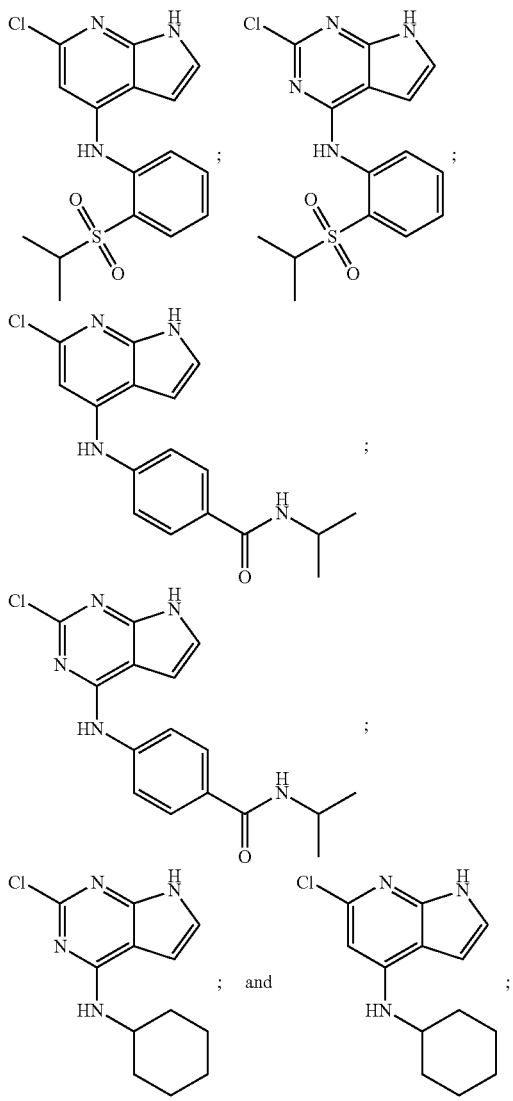

or a tautomer, a pharmaceutically acceptable salt and/or a solvate thereof.

In a further aspect, provided is a method of treating a disease mediated at least in part by protein kinase Mps1, e.g., breast cancer, aggressive breast cancer and triple negative breast cancer, which method comprising administering a therapeutically effective amount of a compound described herein to a patient in need thereof.

In a still further aspect, provided is a method of treating cancer, in particularly breast cancer such as aggressive breast cancer or triple negative breast cancer (TNBC), which method comprising administering a therapeutically effective amount of a compound described herein to a patient in need thereof.

In a still further aspect, provided is a method of treating a patient in need of an inhibitor of protein kinase Mps1, which method comprises determining the level of Mps1 protein and/or mRNA in a tumor cell isolated from the patient; and administering a therapeutically effective amount of a compound described herein to the patient if an overexpression of Mps1 protein and/or mRNA is detected in the patient sample.

In a still further aspect, provided is a method of preparing a compound described herein, or a tautomer, a pharmaceutically acceptable salt and/or a solvate thereof. In some embodiments, the method comprises reacting a 2,4-dihalo-7H-pyrrolo[2,3-d]pyrimidine or an N-protected 2,4-dihalo-7H-pyrrolo[2,3-d]pyrimidine with an optionally substituted aryl amine or an optionally substituted cycloalkyl amine. In some embodiments, the 2,4-dihalo-7H-pyrrolo[2,3-d]pyrimidine is 2,4-dichloro-7H-pyrrolo[2,3-d]pyrimidine. In some embodiments, the N-protected 2,4-dihalo-7H-pyrrolo[2,3-d]pyrimidine is tert-butyl 2,4-dichloro-7H-pyrrolo[2,3-d]pyrimidine-7-carboxylate.

These and other aspects are further described in the text that follows.

DETAILED DESCRIPTION

Definitions

Figure 1:
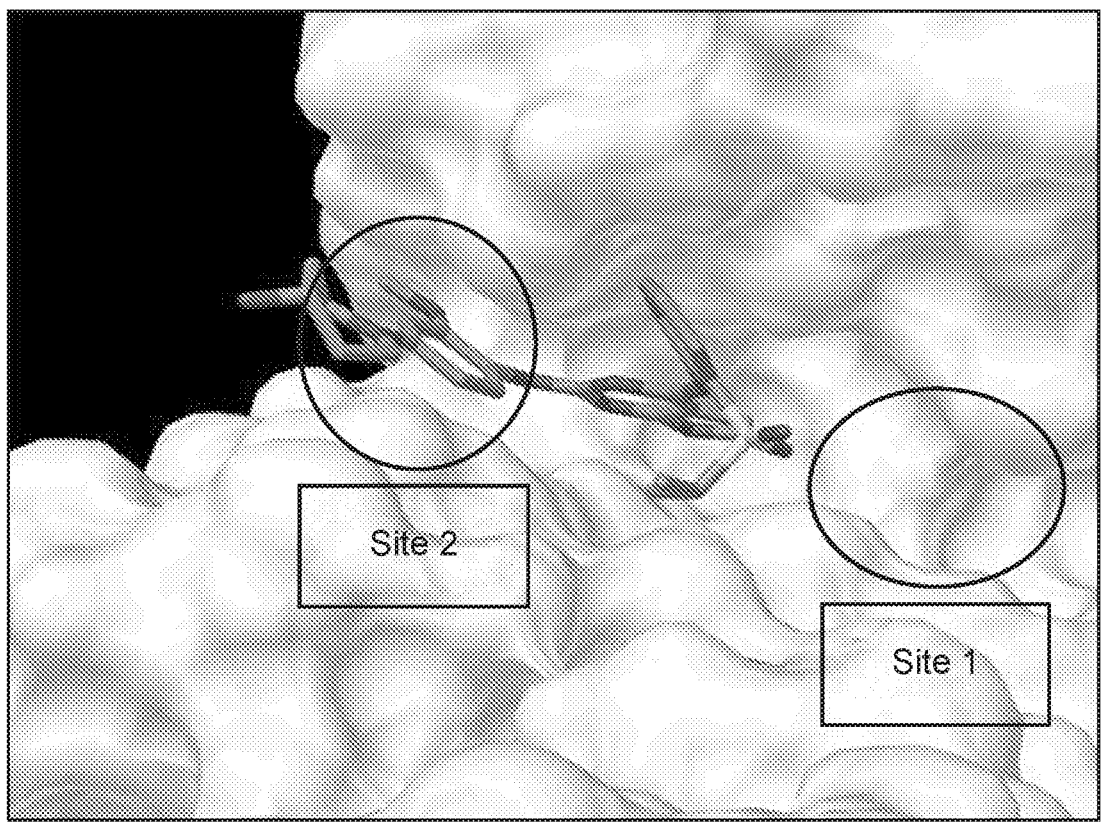
FIG. 1 shows compound 1 and its binding to the Mps1-ATP site.

The practice of the present invention will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

The term "about" when used with numerical designations, e.g., pH, temperature, time, concentration, and molecular weight, including ranges, indicates approximations (+) or (−) 10%, 5%, or 1%, as appropriate.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not. For example, the term "optionally substituted" when describing a moiety means that the moiety is unsubstituted (i.e., all substituents are hydrogen) or substituted (i.e., at least one of the hydrogen atoms of the moiety is replaced by a non-hydrogen substituent).

As used herein, the terms "effective amount" and "amount effective" refer to an amount that is sufficient to achieve the desired result or to have an effect on an undesired condition.

As used herein, "$EC_{50}$," refers to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity.

As used herein, "$IC_{50}$," refers to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

A "composition" is intended to encompass a combination of active agent and a carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodible). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

As used herein, the term "patient" or "subject" refers to an animal, a mammal, in particular a human. For the purpose of illustration only, a mammal includes but is not limited to a human, a feline, a canine, a simian, a murine, a bovine, an equine, a porcine or an ovine. In some aspects, the patient has or is tested to have an increased Mps1 protein level or mRNA expression.

In the context of chemical formulas, the symbol "—" means a single bond, "=" means a double bond, and "≡" means triple bond. The symbol "------" represents an optional bond, which if present is either single or double. The symbol "=====" represents a single bond or a double bond. For example, the structure

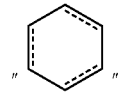

includes the structures

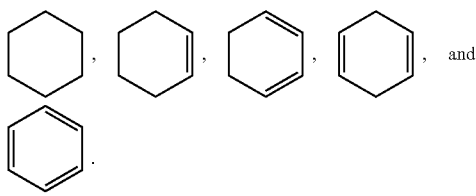

The symbol "⌒⌒⌒" when drawn perpendicularly across a bond indicates a point of attachment of the group.

Embraced herein and unless otherwise indicated, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants, pure isomers or a mixture of the isomers, such as a mixture of enantiomers. A 50:50 mixture of enantiomers is referred to as a racemic mixture.

In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory, and (+) or d meaning that the compound is dextrorotatory. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula.

The symbol "◂▬" means a single bond where the group attached to the thick end of the wedge is "out of the page." The symbol "⋮⋮⋮⋮⋮" means a single bond where the group attached to the thick end of the wedge is "into the page". The symbol "⌒⌒⌒" when used to represent a single bond means that the conformation (e.g., either R or S) or the geometry (e.g., either E or Z) of the bond is undefined, and can be either or both.

It is also appreciated that certain compounds described herein can be present as an equilibrium of tautomers. For example, ketones with an a-hydrogen can exist in an equilibrium of the keto form and the enol form.

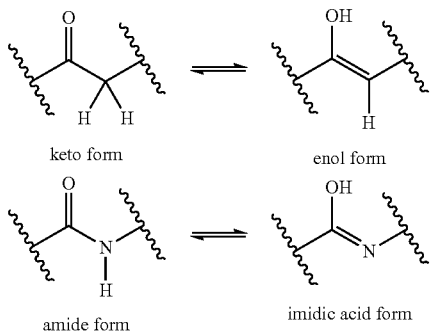

Unless stated to the contrary, the invention includes all such possible tautomers of a compound.

The symbol "($C_n$)" defines the number (n) of carbon atoms in a group. "$C_{n-m}$" defines the range of the number of carbon atoms in a group. For example, $C_3$ alkyl defines an alkyl group having 3 carbon atoms and $C_{3-8}$ cycloalkyl defines a cycloalkyl group having 3 to 8 carbon atoms.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$R^1$," "$R^2$," "$R^3$," and "$R^4$", etc. are used herein as generic symbols to represent various specific substituents. These symbols can be any substituent, not limited to those disclosed herein, and when they are defined to be certain substituents in one instance, they can, in another instance, be defined as some other substituents.

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

When used in the context of a chemical group, "hydrogen" means —H; "hydroxy" and "hydroxyl" can be used interchangeably and mean —OH; "oxo" means =O; "halo" and "halogen", as used herein can be used interchangeably, mean independently —F, —Cl, —Br or —I; "hydroxyamino" means —NHOH; "nitro" means —$NO_2$; imino means =NH; "cyano" and "nitrile" can be used interchangeably and mean —CN; "isocyanate" means —N=C=O; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof, "mercapto" and "thiol" can be used interchangeably and mean —SH; and "thio" means =S; "sulfonyl" means —S(O)$_2$—; and "sulfinyl" means —S(O)—.

The term "alkyl" refers to a straight or branched chain monovalent hydrocarbyl group. In an embodiment, alkyl has from 1 to 20 carbon atoms (i.e., $C_1$-$C_{20}$ alkyl). In some embodiments, alkyl is a $C_1$-$C_{10}$ alkyl group or a $C_1$-$C_6$ alkyl group. The groups —$CH_3$ (Me), —$CH_2CH_3$ (Et), —$CH_2CH_2CH_3$ (n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), and —$CH_2C(CH_3)_3$ are non-limiting examples of alkyl groups.

The term "alkylene" refers to a divalent alkyl group, such as —$CH_2$—, —$CH_2CH_2$—, —$CH_2CH_2CH_2$—, —$CH(CH_3)$$CH_2$—, etc.

The term "alkenyl" refers to a monovalent straight or branched hydrocarbyl group with at least one site of unsaturation, i.e., a carbon-carbon, sp² double bond. In some embodiments, alkenyl is a $C_2$-$C_{20}$ alkenyl group, a $C_2$-$C_{10}$ alkenyl group or a $C_2$-$C_6$ alkenyl group. Examples of alkenyl group include, but are not limited to, —CH═CH₂ (vinyl), —CH═CHCH₃, —CH═CHCH₂CH₃, —CH₂CH═CH₂ (allyl), and —CH₂CH═CHCH₃.

The term "alkenylene" refers to a divalent unsaturated alkenyl group. The groups —CH═CH—, —CH═C(CH₃)CH₂—, and —CH═CHCH₂— are non-limiting examples of alkenylene groups.

"Alkynyl" refers to a monovalent hydrocarbon containing normal, secondary or tertiary carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 10 carbon atoms (i.e., $C_2$-$C_{10}$ alkynyl,) or 2 to 6 carbon atoms (i.e., $C_2$-$C_6$ alkynyl). Examples of alkynyl groups include, but are not limited to, acetylenic (—C≡CH) and propargyl (—CH₂C≡CH).

In some embodiments, the terms "substituted alkyl," "substituted alkylene," "substituted alkenyl," "substituted alkenylene" or "substituted alkynyl" refer to alkyl, alkylene, alkenyl, alkenylene or alkynyl, respectively, wherein at least one of the hydrogen atoms, for example, one to five, one to three, or one or two hydrogen atoms, are independently replaced by a substituent selected from the group consisting of alkenyl, alkynyl, —O—$R^{100}$, —C(O)—$R^{100}$, —$NR^{100}$C(O)$R^{100}$, —C(O)O—$R^{100}$, —$NR^{100}R^{100}$, —C(O)$NR^{100}R^{100}$, —C(S)$NR^{100}R^{100}$, —$NR^{100}$C(O)$NR^{100}R^{100}$, —$NR^{100}$C(S)$NR^{100}R^{100}$, —O—C(O)$NR^{100}R^{100}$, —S(O)₂$NR^{100}R^{100}$, —O—S(O)₂$NR^{100}R^{100}$, —$NR^{100}$—S(O)₂$NR^{100}R^{100}$, —C(═$NR^{100}$)$NR^{100}R^{100}$, aryl, arylthio, azido, carboxyl, —C(O)O—$R^{101}$, —$NR^{100}$—C(O)O—$R^{101}$, —O—C(O)O—$R^{101}$, cyano, cycloalkyl, —$NR^{100}$C(═$NR^{100}$)N($R^{100}$)₂, halo, hydroxy, hydroxyamino, alkoxyamino, —$NR^{100}NR^{100}R^{100}$, heteroaryl, heterocycle, nitro, spirocycloalkyl, —SO₃H, —OS(O)₂—$R^{101}$, —S—$R^{100}$, —S(O)₂—$R^{101}$, —C(S)—$R^{101}$, thiocyanate, thiol, and alkylthio, wherein each $R^{100}$ is independently selected from the group consisting of hydrogen, alkyl, cycloalkyl, aryl, heteroaryl, and heterocycle, or two $R^{100}$ groups attached to a common atom are optionally joined together with the atom bound thereto to form a cycloalkyl or heterocycle; and each $R^{101}$ is independently selected from the group consisting of alkyl, cycloalkyl, aryl, heteroaryl, and heterocycle.

The term "haloalkyl" is a subset of substituted alkyl, in which one or more hydrogens has been substituted with a halo group (i.e., fluorine, chlorine, bromine, or iodine) and no other atoms aside from carbon, hydrogen and halogen are present. The group —CH₂Cl is a non-limiting example of a haloalkyl. The term "fluoroalkyl" is a subset of substituted alkyl, in which one or more hydrogens has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "alkoxy" refers to the group —O-alkyl, and the term "substituted alkoxy" refers the group —O-(substituted alkyl) wherein alkyl and substituted alkyl are as defined herein. Non-limiting examples of alkoxy groups include: —OCH₃, —OCH₂CH₃, —OCH₂CH₂CH₃, —OCH(CH₃)₂, and —OCH(CH₂)₂.

The term "cycloalkyl" as used herein is monovalent a non-aromatic carbon-based ring composed of at least three carbon atoms, for example, 3-14, 3-10 or 3-8 carbons. Cycloalkyl groups include hydrocarbon mono-, bi-, and poly-cyclic rings, whether fused, bridged, or spiro. Examples of cycloalkyl groups include, but are not limited to, cyclopropyl, cyclobutyl, cyclopentyl, cyclohexyl, norbornyl, and the like. The condensed rings may or may not be non-aromatic hydrocarbyl rings provided that the point of attachment is at a cycloalkyl carbon atom. For example, and without limitation, the following is a cycloalkyl group:

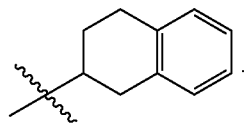 [SMILES: *C1CCc2ccccc2C1]

"Cycloalkylene" refers to a cycloalkyl, as defined herein, having two monovalent radical centers derived by the removal of two hydrogen atoms from the same or two different carbon atoms of a parent cycloalkyl. Examples of cycloalkylene include, but are not limited to, cyclopropylene, cyclobutylene, cyclopentylene and cyclohexylene.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" refers to a monocyclic or bicyclic carbon ring of 5 to 14 carbon ring atoms and up to 7 carbon atoms in each ring, wherein at least one ring is aromatic. Aryl includes a carbocyclic aromatic group fused with a 5-, 6- or 7-membered cycloalkyl group. Non-limiting examples of aryl groups include, but are not limited to, phenyl, naphthyl, biphenyl, tetrahydronaphthyl and indanyl. The condensed ring may or may not be aromatic provided that the point of attachment is at an aromatic carbon atom. For example, and without limitation, the following is an aryl group:

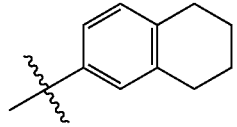

"Arylene" refers to an aryl as defined above having two monovalent radical centers derived by the removal of two hydrogen atoms from two different carbon atoms of a parent aryl. Examples of arylene radicals include, but are not limited to, phenylene, e.g.,

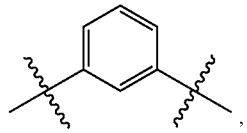 [SMILES: *c1cccc(*)c1]

and naphthylene, e.g.,

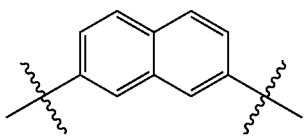

"Arylalkylene" refers to an aralkyl as defined above having two monovalent radical centers derived by the removal of one hydrogen atom from the aryl radical and the other hydrogen removed from the alkyl radical of the group.

The term "heteroaryl" refers to a monocyclic, bicyclic or tricyclic ring having from 5 to 14 ring atoms and from 5 to 7 ring atoms in each ring, wherein at least one ring is aromatic and contains from 1 to 4 heteroatoms in the ring selected from the group consisting of N, O and S. If more than one ring is present, the rings may be fused or unfused. "Heteroaryl" is also understood to include the N-oxide derivative of any nitrogen containing heteroaryl. The condensed rings may or may not be a heteroatom containing aromatic ring provided that the point of attachment is a heteroaryl atom. For example, and without limitation, the following is a heteroaryl group:

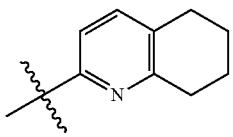
,

The term "heterocycloalkyl" or "heterocycle" is a monovalent non-aromatic ring group comprising 3 to 14, 3 to 10, or 3 to 8 ring atoms, where at least one of the ring atoms is carbon atom, and at least one of the ring atoms, for example, 1, 2, 3, or 4 ring atoms, are heteroatoms such as, but not limited to, nitrogen, oxygen, sulfur, or phosphorus. Heterocycloalkyl groups comprising 3 to 14 or 3 to 10 ring atoms may be referred to as 3 to 14 membered or 3 to 10 membered heterocycloalkyl. Heterocycloalkyl groups include, for example, 4-membered, 5-membered, 6-membered, and 7-membered heterocycloalkyl. The condensed rings may or may not be a non-aromatic heteroatom containing ring provided that the point of attachment is a heterocycle group. For example, and without limitation, the following is a heterocycle group:

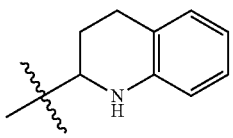
.

Examples of heterocycloalkyl and heteroaryl include, but are not limited to, pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1, 2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl, 1H-pyrrolo[3,2-b]pyridin-3-yl, and 1H-pyrazolo [3,2-b]pyridin-3-yl.

"Heteroarylene" refers to a heteroaryl, as defined above, having two monovalent radical centers derived by the removal of two hydrogen atoms from the same or two different carbon atoms of a parent heteraryl group. Non-limiting examples of heteroarylene groups are:

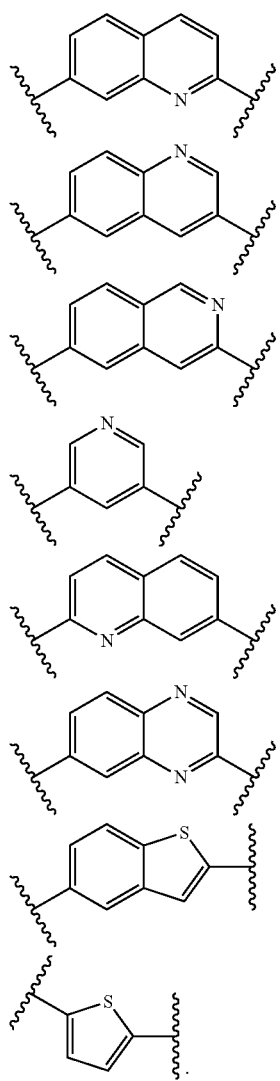

In some embodiments, the terms "substituted cycloalkyl," "substituted cycloalkylene," "substituted aryl," "substituted arylene," "substituted heteroaryl", or "substituted heteroarylene" refer to cycloalkyl, cycloalkylene, aryl, arylene, heteroaryl or heteroarylene wherein at least one of the hydrogen atoms, for example, one to five, one to three, or one or two hydrogen atoms, are independently replaced by a substituent selected from the group consisting of alkyl, alkenyl, alkynyl, —O—R$^{100}$, —C(O)—R$^{10}$, —NR$^{100}$C(O)R$^{100}$, —C(O)O—R$^{100}$, —NR$^{100}$R$^{100}$, —C(O)NR$^{100}$R$^{100}$, —C(S)NR$^{100}$R$^{100}$, —NR$^{100}$C(O)NR$^{100}$R$^{100}$, —NR$^{100}$C(S)

$NR^{100}R^{100}$, —O—C(O)$NR^{100}R^{100}$, —S(O)$_2NR^{100}R^{100}$, —O—S(O)$_2NR^{100}R^{100}$, —$NR^{100}$—S(O)$_2NR^{100}R^{100}$, —C(=$NR^{100}$)$NR^{100}R^{100}$, aryl, arylthio, azido, carboxyl, —C(O)O—$R^{101}$, —$NR^{100}$—C(O)O—$R^{101}$, —O—C(O)O—$R^{101}$, cyano, cycloalkyl, —$NR^{100}$C(=$NR^{00}$)N($R^{100}$)$_2$, halo, hydroxy, hydroxyamino, alkoxyamino, —$NR^{100}NR^{100}R^{100}$, heteroaryl, heterocycle, nitro, spirocycloalkyl, —SO$_3$H, —OS(O)$_2$—$R^{101}$, —S—$R^{100}$, —S(O)$_2$—$R^{101}$, —C(S)—$R^{101}$, thiocyanate, thiol, and alkylthio, wherein each $R^{100}$ is independently selected from the group consisting of hydrogen, alkyl, cycloalkyl, aryl, heteroaryl, and heterocycle, or two $R^{100}$ groups attached to a common atom are optionally joined together with the atom bound thereto to form a heterocycle; and each $R^{101}$ is independently selected from the group consisting of alkyl, cycloalkyl, aryl, heteroaryl, and heterocycle.

"Cycloalkylalkyl" refers to an alkyl moiety substituted with a cycloalkyl group. Examples of cycloalkylalkyl groups include cyclopropylmethyl, cyclobutylmethyl, cyclopentylethyl and cyclohexylmethyl. Substituted cycloalkylalkyl refers to a cycloalkylalkyl wherein either or both the alkyl or cycloalkyl portions are substituted as defined herein.

The term "aralkyl" refers to an alkyl group, as defined herein, in which a hydrogen atom has been replaced with an aryl group. Substituted aralkyl refers to an aralkyl wherein either or both the alkyl or aryl portions are substituted as defined herein.

The term "arylalkylene" refers to an aralkyl as defined above having two monovalent radical centers derived by the removal of one hydrogen atom from the aryl radical and the other hydrogen removed from the alkyl radical of the group.

The term "heteroaralkyl," refers to an alkyl group, as defined herein, in which a hydrogen atom has been replaced with a heteroaryl group. Substituted heteroaralkyl refers to a heteroaralkyl wherein either or both the alkyl or heteroaryl portions are substituted as defined herein.

The term "aldehyde" as used herein is represented by the formula —C(O)H. Throughout this specification "CO" or "C(O)" is a short hand notation for a carbonyl group, i.e., C=O.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, heterocycle, alkynyl, cycloalkynyl, aryl, or heteroaryl group as described herein.

The term "ether" as used herein is represented by the formula $A^1$-O-$A^2$, where $A^1$ and $A^2$ can be, independently, optionally substituted alkyl, cycloalkyl, heterocycle, alkenyl, cycloalkenyl, alkynyl, cycloalkynyl, aryl, or heteroaryl group described herein.

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, halo, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "pharmaceutically acceptable salt" refers to a salt of the compound described herein that is, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein).

A solvate of a compound is a solid-form of the compound that crystallizes with less than one, one or more than one molecules of a solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder, or the relief or elimination of a symptom thereof. Thus, treatment includes:

preventing or protecting against the disease or disorder, that is, causing the clinical symptoms not to develop; and/or inhibiting the disease or disorder, that is, arresting or suppressing the development of clinical symptoms; and/or relieving the disease or disorder that is, causing the regression of clinical symptoms; and/or reducing the metastasis of the primary tumor or cancer.

"Administration" can be effected in one dose, continuously or intermittently throughout the course of treatment. Methods of determining the effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intraperitoneal, intravenous and by inhalation. An agent of the present invention can be administered for therapy by any suitable route of administration. It will also be appreciated that the preferred route will vary with the condition and age of the recipient, and the disease being treated. Administration includes the act of applying a therapy to a patient, or prescribing a therapy to a patient, or instructing or advising a patient to take a therapy.

As used herein the term "aggressive breast cancer" intends invasive (infiltrating) breast cancer. The cancerous cells break through normal breast tissue barriers and spread to other parts of the body through the bloodstream and lymph nodes.

As used herein the term "triple negative breast cancer" (TNBC) is used to describe breast cancer (usually invasive ductal carcinomas) whose cells lack estrogen receptors and progesterone receptors and do not have an excess of the HER2 protein on their surface. These cancers tend to grow and spread more quickly than most other types of breast cancers. A diagnosis of TNBC is based on a test for the presence or absence of these receptors on tumor cells isolated from the patient.

As used herein, the term "disease mediated in least in part by protein kinase Mps1" intends a disease state that is related or correlated to increased Mps1 protein or mRNA expression in a cell isolated from a patient. Methods to determine the relative level of protein and mRNA expression in a sample are known in the art and briefly described herein.

The agents and compositions can be used in the manufacture of medicaments and kits that are useful in the treatment of humans and other animals by administration in accordance with conventional procedures, such as an active ingredient in pharmaceutical compositions.

Compounds

Provided herein are Mps1/TTK kinase inhibitory compounds useful in treating breast cancer. A 2011 study reported a high-throughput RNAi screening of a series of pharmacologically tractable genes followed by comprehensive functional viability assay profiles for a panel in >30 commonly used breast tumor cell models to identify genes critical to the growth of specific breast cancer subtypes (4). Analysis of these profiles identified a series of novel genetic dependencies and suggested potential new therapeutic targets for aggressive breast cancers. One group of genes identified was mitotic checkpoint kinases, including Mps1/TTK. Other studies in 2011 and 2013 reported that high levels of Mps1 protein has been correlated with high histologic grade in BC, while reducing Mps1 levels in BC cells by RNAi resulted in aberrant mitoses, induction of apoptosis, and decreased ability of BC cells to grow as xenografts in nude mice (5; 6). These studies suggest Mps1 as a potential therapeutic target in aggressive BCs.

The dual specificity protein kinase Mps1 (also known as TTK or Mps1/TTK) is required for centrosome duplication and the spindle assembly checkpoint. While the Mps1 gene (monopolar spindle) was first identified in the budding yeast, Saccharomyces cerevisiase (7), its orthologs from humans [phosphotyrosine-picked threonine kinase/threonine and tyrosine kinase (PYT/TTK)] had been discovered as a dual specificity protein kinase (8; 9). Mps1/TTK regulates centrosome duplication and the spindle checkpoint (10). Its substrates include the centriolar protein Centrin 2 (11) and its centrosomal levels are controlled by proteasome-mediated degradation (12-14). Preventing this degradation is sufficient to cause centrosome re-duplication (13-15), and defects in this control are correlated with centrosome amplification and tumorigenesis (12; 13). Further, Mps1/TTK directly phosphorylates Chk2 in vitro (16). In addition both mRNA and protein levels of Mps1/TTK are readily detectable in all proliferating cells and tissues, but markedly reduced or absent in resting cells and tissues with a low proliferative index. Mps1/TTK regulates cell cycle progression (17; 18), and alterations to Mps1/TTK have been associated with cell transformation and chromosome instability in different tumor models (19). Both mRNA and protein levels of Mps1 are readily detectable in proliferating BC cells, while markedly reduced or absent in breast cancer cells with a low proliferative index. Notably, breast cells are particularly sensitive to increases in Mps1/TTK protein levels and, unlike in other cell types, overexpression of wild type Mps1/TTK causes centrosome re-duplication in breast-derived cells (13). Amplification of centrosomes is particularly prevalent in breast cancer. As many as 80% of invasive breast tumors have extra centrosomes (20) that generate aberrant mitotic spindles in situ (21). The appearance of extra centrosomes is an early occurrence in breast tumorigenesis (20) and correlates with aneuploidy in invasive tumors (20; 22). Also, reports suggest that silencing Mps1/TTK, which has dual roles in checkpoint activation and chromosome alignment, can sensitize cancer cells to sub-lethal doses of paclitaxel, whereas non-tumorigenic cells cannot be sensitized. Several Mps1/TTK inhibitors have been developed and tested in recent years (23-27), such as Mps1-IN-1, Mps1-IN-3, AZ3146, and MPI-0479605.

The designing and developing novel small molecule Mps1/TTK inhibitors as targeted therapies for TNBC and aggressive BC is disclosed. Such agents are contemplated to provide safe, effective interventions and reduce life-threatening toxicities which may replace standard cytotoxic chemotherapies as monotherapy or in combination with current treatment regimens. These studies will also identify the role of Mps1 in breast cancer growth and metastasis.

In one aspect, provided herein are compounds of Formula IV-A, IV-B, IV-C, V-A, V-B, or V-C:

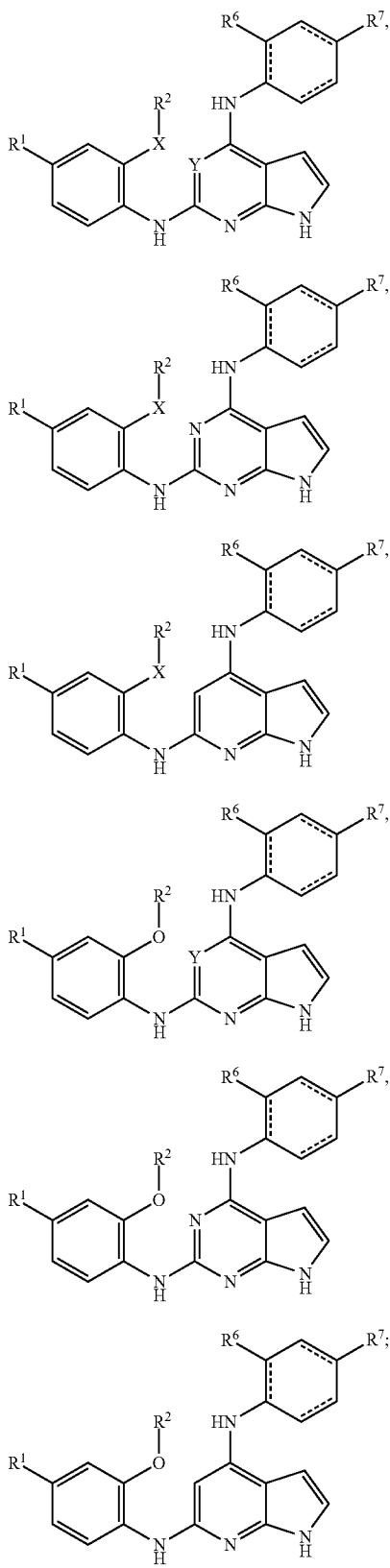

or a tautomer, a pharmaceutically acceptable salt and/or a solvate thereof;

wherein
R¹ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —C(O)O—$R^{10}$, —$NR^{10}R^{11}$, —C(O)$NR^{10}R^{11}$, —C(S)$NR^{10}R^{11}$, —$NR^{13}C(O)NR^{10}R^{11}$, —$NR^{13}C(S)NR^{10}R^{11}$, —O—C(O)$NR^{10}R^{11}$, —$S(O)_2NR^{10}R^{11}$, —O—$S(O)_2NR^{10}R^{11}$, —$NR^{13}$—$S(O)_2NR^{10}R^{11}$, CN, halo, $NO_2$, and —$S(O)_2$—$R^{12}$;

$R^2$ is selected from the group consisting of hydrogen, $C_1$-$C_3$ alkyl and $C_1$-$C_3$ haloalkyl; provided that when X is $SO_2$, or when $R^1$ is hydrogen, then $R^2$ is not hydrogen;

$R^6$ is selected from the group consisting of hydrogen, halo, —O—$R^{20}$, —C(O)—$R^{20}$, —C(O)O—$R^{20}$, —$NR^{20}R^{21}$, —C(S)$NR^{20}R^{21}$, —$NR^{23}C(O)NR^{20}R^{21}$, —$NR^{23}C(S)NR^{20}R^{21}$, —O—C(O)$NR^{20}R^{21}$, —$S(O)_2NR^{20}R^{21}$, —O—$S(O)_2NR^{20}R^{21}$, —$NR^{23}$—$S(O)_2NR^{20}R^{21}$, CN, $NO_2$, $C_1$-$C_6$ alkyl and —$S(O)_2$—$R^{22}$;

$R^7$ is selected from the group consisting of hydrogen, halo, —O—$R^{20}$, —C(O)—$R^{20}$, —C(O)O—$R^{20}$, —$NR^{20}R^{21}$, —C(O)$NR^{20}R^{21}$, —C(S)$NR^{20}R^{21}$, —$NR^{23}C(O)NR^{20}R^{21}$, —$NR^{23}C(S)NR^{20}R^{21}$, —O—C(O)$NR^{20}R^{21}$, —$S(O)_2NR^{20}R^{21}$, —O—$S(O)_2NR^{20}R^{21}$, —$NR^{23}$—$S(O)_2 NR^{20}R^{21}$, CN, $NO_2$, $C_1$-$C_6$ alkyl and —$S(O)_2$—$R^{22}$;

each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle; or $R^{20}$ and $R^{21}$ together with the atom attached thereto form a 5- to 7-membered heterocycle;

$R^{12}$ and $R^{22}$ is independently $C_1$-$C_6$ alkyl; and

==== represents a single bond or a double bond.

In some aspects, provided is a compound of Formula VI

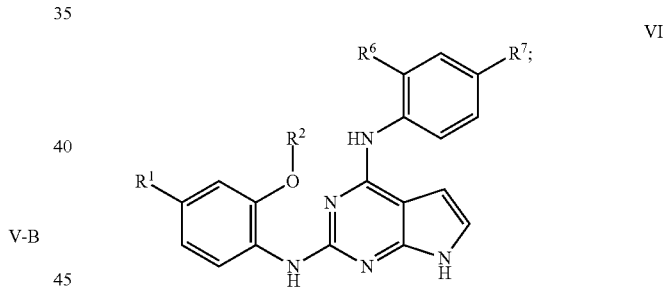

or a tautomer, a pharmaceutically acceptable salt and/or a solvate thereof, wherein $R^1$, $R^2$, $R^6$, and $R^7$ are defined as above.

In some aspect, provided is a compound of Formula VII

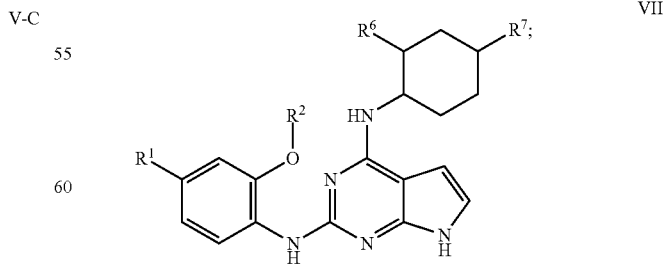

or a tautomer, a pharmaceutically acceptable salt and/or a solvate thereof, wherein $R^1$, $R^2$, $R^6$, and $R^7$ are defined as above.

In some aspects, provided is a compound of Formula VIII

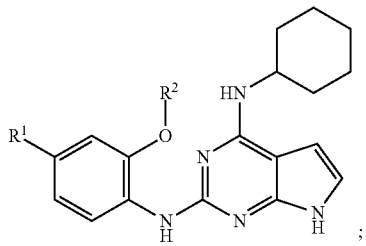

VIII or a tautomer, a pharmaceutically acceptable salt and/or a solvate thereof, wherein $R^1$ and $R^2$ are defined as above.

In some aspects of Formula IV-A, IV-B, IV-C, V-A, V-B, V-C, VI, VII or VIII, $R^1$ is hydrogen.

In some aspects of Formula IV-A, IV-B, IV-C, V-A, V-B, V-C, VI, VII or VIII, $R^1$ is 5- to 7-membered heterocycle selected from the group consisting of pyrrolidine, oxazolidine, isoxazolidine, thiazolidine, imidazolidine, piperidine, morpholine, piperazine, thiomorpholine, diazepane, 1,4-diazepane, oxazepane, 1,4-oxazepane, thiazepane, and 1,4-thiazepane, wherein the 5- to 7-membered heterocycle is optionally substituted with $R^3$.

In some aspects of Formula IV-A, IV-B, IV-C, V-A, V-B, V-C, VI, VII or VIII, $R^1$ is selected from the group consisting of

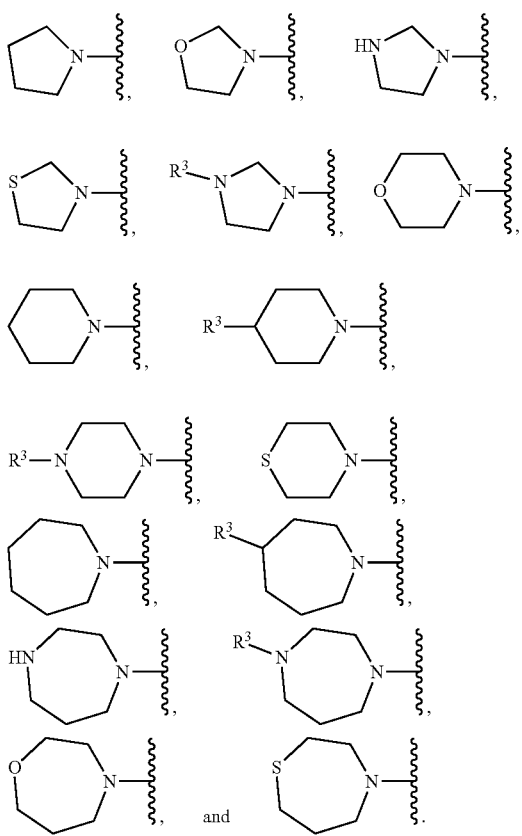

and

In some aspects of Formula IV-A, IV-B, IV-C, V-A, V-B, V-C, VI, VII or VIII, $R^1$ is selected from the group consisting of

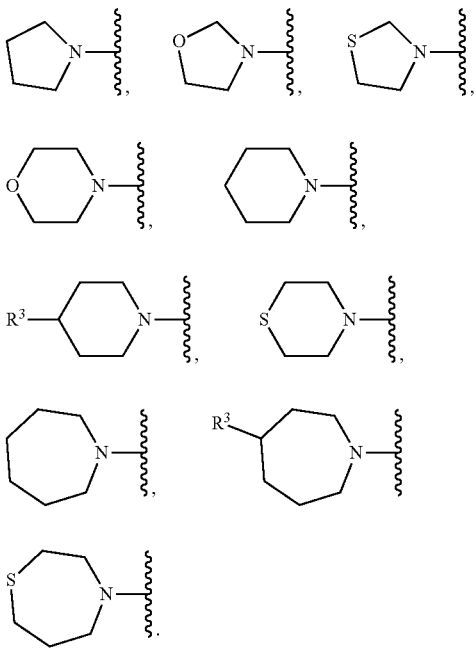

and

In some aspects, $R^3$ is OH.

In some aspects of Formula IV-A, IV-B, IV-C, V-A, V-B, V-C, VI, VII or VIII, $R^2$ is $C_1$-$C_3$ alkyl, such as methyl. In some aspects, $R^6$ is —S(O)$_2$—R$^{22}$. In some aspects, $R^6$ is hydrogen. In some aspects, $R^7$ is —C(O)NR$^{20}$R$^{21}$. In some aspects, $R^7$ is hydrogen.

In some aspects of Formula IV-A, IV-B, IV-C, V-A, V-B, V-C, VI, VII or VIII, $R^1$ is hydrogen, $R^2$ is $C_1$-$C_6$ alkyl, such as methyl, $R^6$ is —S(O)$_2$—R$^{22}$, and $R^7$ is hydrogen. In some aspects, $R^6$ is —SO$_2$CH(CH$_3$)$_2$.

In some aspects of Formula IV-A, IV-B, IV-C, V-A, V-B, V-C, VI, VII or VIII, $R^1$ is morpholinyl, $R^2$ is $C_1$-$C_6$ alkyl, such as methyl, $R^6$ is —S(O)$_2$—R$^{22}$, and $R^7$ is hydrogen. In some aspects, $R^6$ is —SO$_2$CH(CH$_3$)$_2$.

In some aspects of Formula IV-A, IV-B, IV-C, V-A, V-B, V-C, VI, VII or VIII, $R^1$ is piperidinyl optionally substituted with OH, $R^2$ is $C_1$-$C_6$ alkyl, such as methyl, $R^6$ is —S(O)$_2$—R$^{22}$, and $R^7$ is hydrogen. In some aspects, $R^6$ is —SO$_2$CH(CH$_3$)$_2$.

In some aspects of Formula IV-A, IV-B, IV-C, V-A, V-B, V-C, VI, VII or VIII, $R^1$ is hydrogen, $R^2$ is $C_1$-$C_6$ alkyl, such as methyl, $R^6$ is hydrogen, and $R^7$ is —C(O)NR$^{20}$R$^{21}$, such as —C(O)NHCH(CH$_3$)$_2$.

In some aspects of Formula IV-A, IV-B, IV-C, V-A, V-B, V-C, VI, VII or VIII, $R^1$ is morpholinyl, $R^2$ is $C_1$-$C_6$ alkyl, such as methyl, $R^6$ is hydrogen, and $R^7$ is —C(O)NR$^{20}$R$^{21}$, such as —C(O)NHCH(CH$_3$)$_2$.

In some aspects of Formula IV-A, IV-B, IV-C, V-A, V-B, V-C, VI, VII or VIII, $R^1$ is piperidinyl optionally substituted with $R^3$, such as OH, $R^2$ is $C_1$-$C_6$ alkyl, such as methyl, $R^6$ is hydrogen, and $R^7$ is —C(O)NR$^{20}$R$^{21}$, such as —C(O)NHCH(CH$_3$)$_2$.

In some aspects, provided herein are compounds selected from:

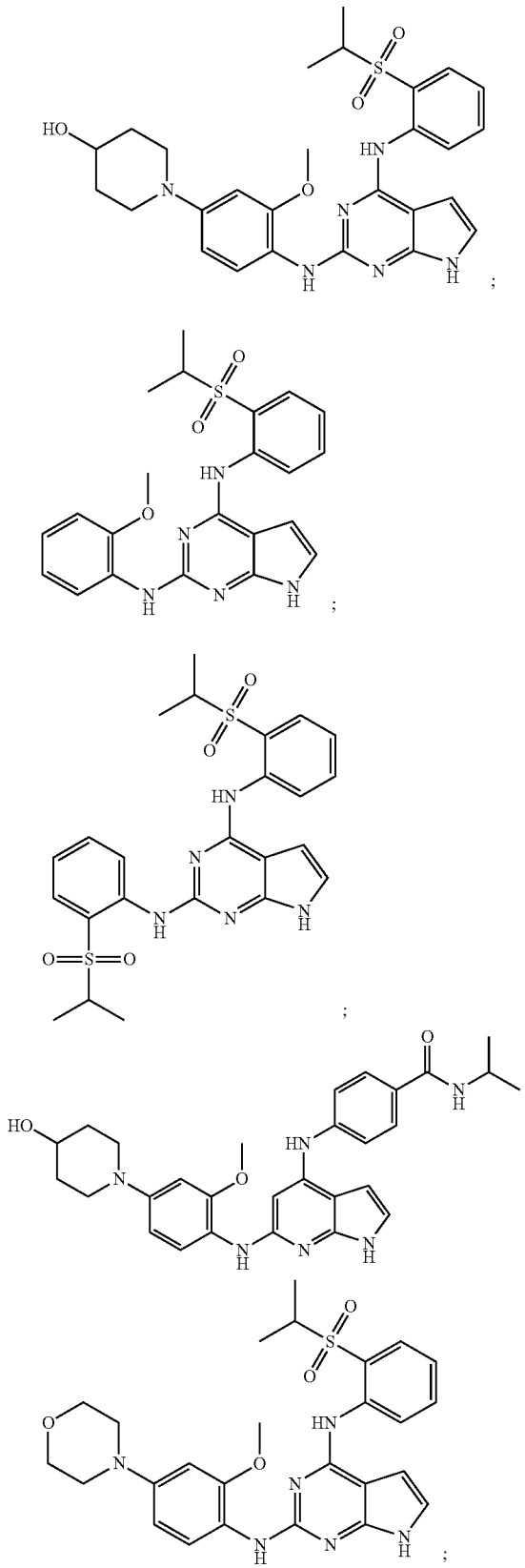

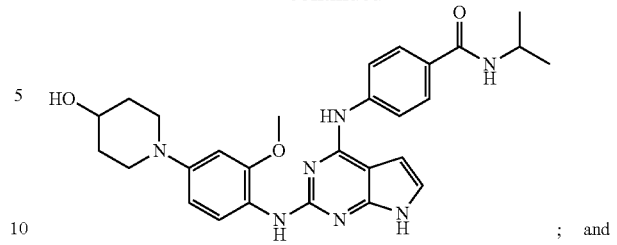

; and

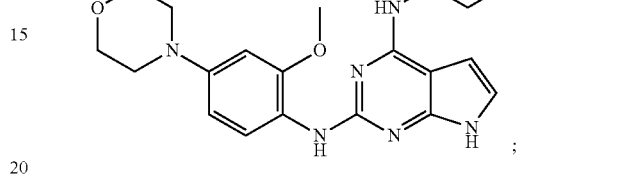

;

or a tautomer, a pharmaceutically acceptable salt and/or a solvate thereof.

In one aspect, provided herein are compounds of Formula X or XI:

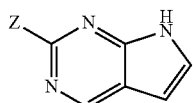  X

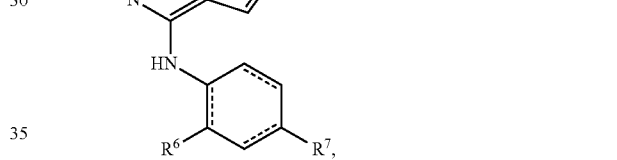

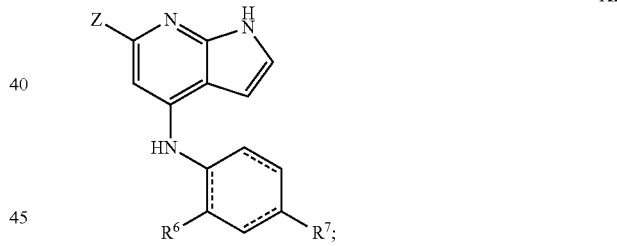  XI or a tautomer, a pharmaceutically acceptable salt and/or a solvate thereof;

wherein

Z is chloro or bromo;

$R^6$ is selected from the group consisting of hydrogen, halo, —O—$R^{20}$, —C(O)—$R^{20}$, —C(O)O—$R^{20}$, —$NR^{20}R^{21}$, —C(S)$NR^{20}R^{21}$, —$NR^{23}$C(O)$NR^{20}R^{21}$, —$NR^{23}$C(S) $NR^{20}R^{21}$, —O—C(O)$NR^{20}R^{21}$, —S(O)$_2$$NR^{20}R^{21}$, —O—S(O)$_2$$NR^{20}R^{21}$, —$NR^{23}$—S(O)$_2$$NR^{20}R^{21}$, CN, $NO_2$, $C_1$-$C_6$ alkyl and —S(O)$_2$—$R^{22}$;

$R^7$ is selected from the group consisting of hydrogen, halo, —O—$R^{20}$, —C(O)—$R^{20}$, —C(O)O—$R^{20}$, —$NR^{20}R^{21}$, —C(O)$NR^{20}R^{21}$, —C(S)$NR^{20}R^{21}$, —$NR^{23}$C(O) $NR^{20}R^{21}$, —$NR^{23}$C(S)$NR^{20}R^{21}$, —O—C(O)$NR^{20}R^{21}$, —S(O)$_2$$NR^{20}R^{21}$, —O—S(O)$_2$$NR^{20}R^{21}$, —$NR^{23}$—S (O)$_2$ $NR^{20}R^{21}$, CN, $NO_2$, $C_1$-$C_6$ alkyl and —S(O)$_2$—$R^{22}$;

each of $R^{20}$, $R^{21}$, and $R^{23}$ is independently hydrogen or $C_1$-$C_6$ alkyl; or $R^{20}$ and $R^{21}$ together with the atom attached thereto form a 5- to 7-membered heterocycle;

$R^{22}$ is $C_1$-$C_6$ alkyl; and

==== represents a single bond or a double bond.

In one aspect, provided herein are the following compounds

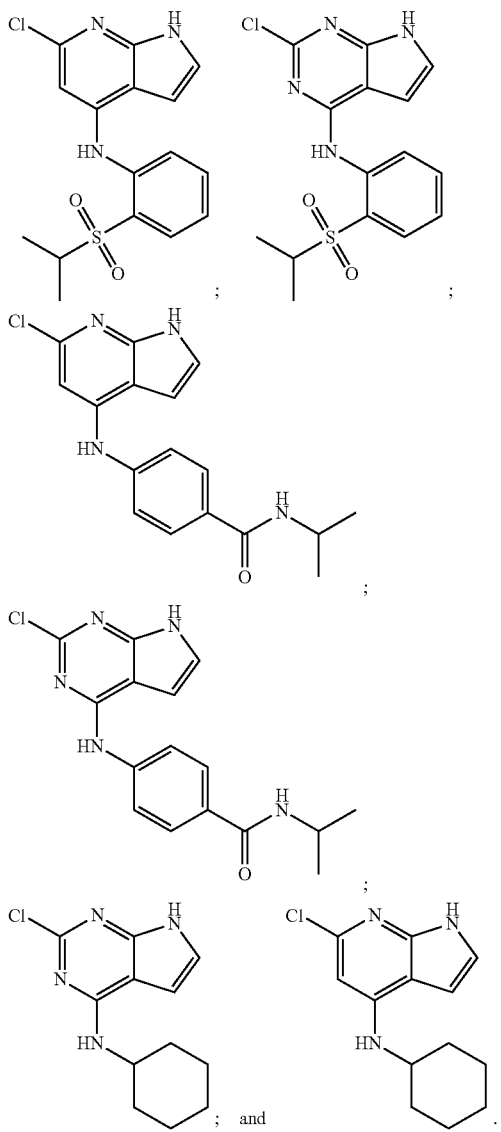

; and or a tautomer, a pharmaceutically acceptable salt and/or a solvate thereof.

Pharmaceutical Compositions

In another aspect, provided are compositions comprising a compound described herein, such as a compound of Formula IV-A, IV-B, IV-C, V-A, V-B, V-C, VI, VII, VIII, X or XI. In general, the compound is mixed with a suitable carrier or excipient in a therapeutically effective amount. By a "therapeutically effective dose", "therapeutically effective amount", or, interchangeably, "pharmacologically acceptable dose" or "pharmacologically acceptable amount", it is meant that a sufficient amount of the compound and a pharmaceutically acceptable carrier, will be present in order to achieve a desired result, e.g., treating a disease mediated at least in part by Mps1/TTK kinase.

In general, the compounds described herein will be administered in a therapeutically effective amount by any of the accepted modes of administration. The actual amount of the compound, i.e., the active ingredient, will depend upon numerous factors such as the severity of the disease to be treated, the age and relative health of the subject, the potency of the compound used, the route and form of administration, and other factors. The compound can be administered according to any suitable dosage regimes, such as once, twice, three times, or four times, etc. a day, or as needed. All of these factors are within the skill of the attending clinician. In some embodiments, the compound is administered one or more times during a treatment cycle. In further embodiments, the treatment cycle is 21 days. In other embodiments, the treatment cycle is 28 days. In some embodiments, the compound is administered one or more times during a treatment cycle for up to four treatment cycles.

Therapeutically effective amounts of the compounds may range from approximately 0.05 to 50 mg per kilogram body weight of the recipient per day; for example, about 0.1-25 mg/kg/day, or from about 0.5 to 10 mg/kg/day. Thus, for administration to a 70 kg person, the dosage range can be about 1-3500 mg per day.

In some of the embodiments of the present technology described herein, the pharmaceutical compositions are packaged in unit dosage form. The unit dosage form is effective in treating a disease and/or disorder. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

In some embodiments, the unit dosage comprises 0.01 mg/kg to 0.5 g/kg. In some embodiments, the unit dosage comprises 0.01 mg/kg to 100 mg/kg. In some embodiments, the unit dosage comprises 0.01 mg/kg to 50 mg/kg. In some embodiments, the unit dosage comprises 0.01 mg/kg to 10 mg/kg. In some embodiments, the unit dosage comprises 0.01 mg/kg to 5 mg/kg. In some embodiments, the unit dosage comprises 0.1 mg/kg to 0.5 g/kg. In some embodiments, the unit dosage comprises 0.1 mg/kg to 100 mg/kg. In some embodiments, the unit dosage comprises 0.1 mg/kg to 50 mg/kg. In some embodiments, the unit dosage comprises 0.01 mg/kg to 10 mg/kg. In some embodiments, the unit dosage comprises 0.1 mg/kg to 5 mg/kg.

In general, compounds described herein will be administered as pharmaceutical compositions by any one of the following routes: oral, transdermal, intranasal, by suppository, parenteral (e.g., intramuscular, intravenous or subcutaneous), or intrathecal administration. Compositions can take the form of tablets, pills, capsules, semisolids, powders, sustained release formulations, solutions, suspensions, elixirs, aerosols, or any other appropriate compositions. The choice of formulation depends on various factors such as the mode of drug administration and bioavailability of the drug substance.

Another manner for administering compounds is inhalation. This is an effective method for delivering a therapeutic agent directly to the respiratory tract (see U.S. Pat. No. 5,607,915). For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The compositions are comprised of in general, a compound described herein in combination with at least one pharmaceutically acceptable excipient. Acceptable excipients are non-toxic, aid administration, and do not adversely affect the therapeutic benefit of the compound. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, phosphate buffered saline, citrate buffer, aqueous dextrose, and glycols, etc.

Compressed gases may be used to disperse a compound in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain from about 0.01-99.99 wt % of the compound based on the total weight of the formulation, with the balance being one or more suitable pharmaceutical excipients. Preferably, the compound is present at a level of about 1-80 wt %.

Combination Therapy

In some embodiments, the compounds disclosed herein are combined with one or more additional therapeutic agents for treating a subject in need thereof. In some embodiments, the one or more additional therapeutic agents are selected from anti-cancer compounds. When a combination therapy is used, the one or more additional therapeutic agents may be administered sequentially or simultaneously with a compound described herein. In some embodiments, the one or more additional therapeutic agents is administered prior to the administration of a compound described herein. In some embodiments, the one or more additional therapeutic agents is administered after the administration of a compound described herein. In some embodiments, the one or more additional therapeutic agents is administered concurrently with the administration of a compound described herein.

In some embodiments, the one or more additional therapeutic agents is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKC.beta. inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors. Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF-0337210 (Pfizer), SU 14843 (Pfizer), AZD 2171 (AstraZeneca), ranibizumab (Lucentis®), Neovastat® (AE 941), tetrathiomolybdata (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which can be used in conjunction with a compound disclosed herein include celecoxib (Celebrex®), parecoxib (Dynastat®), deracoxib (SC 59046), lumiracoxib (Preige®), valdecoxib (Bextra®), rofecoxib (Vioxx®), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®) nabumetone (Relafen®), piroxicam (Feldene®), naproxen (Aleve®, Naprosyn®) diclofenac (Voltaren®), indomethacin (Indocin®), sulindac (Clinoril®), tolmetin (Tolectin®), etodolac (Lodine®), ketorolac (Toradol®), and oxaprozin (Daypro®).

Other anti-angiogenesis agents include ABT 510 (Abbott), apratastat (TMI 005), AZD 8955 (AstraZeneca), incyclinide (Metastat®), and PCK 3145 (*Procyon*).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem® (2-methoxyestradiol), PF-03446962 (Pfizer), rebimastat (BMS 275291), catumaxomab (Removab®), lenalidomide (Revlimid®) squalamine (EVIZON®), thalidomide (Thalomid®), Ukrain® (NSC 631570), Vitaxin® (MEDI 522), and zoledronic acid (Zometa®).

In some embodiments, the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, ALK inhibitors, ROS1 inhibitors, TrkA inhibitors, TrkB inhibitors, TrkC inhibitors, farnesyl protein transferase inhibitors, EGF inhibitor, ErbB-1 (EGFR), ErbB-2, pan erb, IGF 1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa®), cetuximab (Erbitux®), erlotinib (Tarceva®), trastuzumab (Herceptin®), sunitinib (Sutent®) imatinib (Gleevec®), and PD325901 (Pfizer).

Additional examples of signal transduction inhibitors include BMS 214662 (Bristol-Myers Squibb), lonafarnib (Sarasar®), pelitrexol (AG 2037), matuzumab (EMD 7200), nimotuzumab (TheraCIM h-R3®), panitumumab (Vectibix®), Vandetanib (Zactima®), pazopanib (SB 786034), ALT 110 (Alteris Therapeutics), BIBW 2992 (Boehringer Ingelheim), and Cervene® (TP 38).

Other examples of signal transduction inhibitor include PF-2341066 (Pfizer), PF-299804 (Pfizer), canertinib (CI 1033), pertuzumab (Omnitarg®), Lapatinib (Tycerb®), pelitinib (EKB 569), miltefosine (Miltefosin®), BMS 599626 (Bristol-Myers Squibb), Lapuleucel-T (Neuvenge®), NeuVax® (E75 cancer vaccine), Osidem® (IDM 1), mubritinib (TAK-165), CP-724,714 (Pfizer), panitumumab (Vectibix®), lapatinib (Tycerb®), PF-299804 (Pfizer), pelitinib (EKB 569), and pertuzumab (Omnitarg®).

Other examples of signal transduction inhibitors include ARRY 142886 (Array Biopharm), everolimus (Certican®), zotarolimus (Endeavor®), temsirolimus (Torisel®), AP 23573 (ARIAD), and VX 680 (Vertex).

Additionally, other signal transduction inhibitors include XL 647 (Exelixis), sorafenib (Nexavar®), LE-AON (Georgetown University), and GI-4000 (GlobeImmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), AG 024322 (Pfizer), LOXO-101 (Loxo Oncology), crizotinib, and ceritinib.

In some embodiments, a compound disclosed herein is used together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with a compound disclosed herein, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with a compound disclosed herein include, but are not limited to, suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In some embodiments, a compound disclosed herein is used together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda®), cytosine arabinoside, Gemzar® (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound disclosed herein, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta®), DMXAA (Antisoma), ibandronic acid, L-asparaginase, pegaspargase (Oncaspar®), Efaproxiral (Efaproxyn®—radiation therapy)), bexarotene (Targretin®), Tesmilifene (DPPE—enhances efficacy of cytotoxics)), Theratope® (Biomira), Tretinoin (Vesanoid®), tirapazamine (Trizaone®), motexafin gadolinium (Xcytrin®) Cotara® (mAb), and NBI-3001 (Protox Therapeutics), polyglutamate-paclitaxel (Xyotax®) and combinations thereof.

Further examples of classical antineoplastic agents used in combination therapy with a compound disclosed herein, optionally with one or more other agents including, but are not limited to, as Advexin (ING 201), TNFerade (GeneVec, one or more compounds which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Some embodiments relate to a method for the treatment of breast cancer in a subject in need of such treatment, comprising administering to said subject an amount of a compound disclosed herein, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

Treatment of Diseases

In one aspect, provided are methods of inhibiting Mps1/TTK kinase comprising, consisting of or consisting essentially of, contacting Mps1/TTK with a compound of Formula I-A, I-B or I-C:

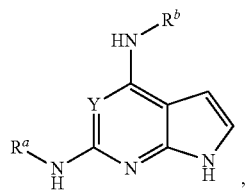

I-A

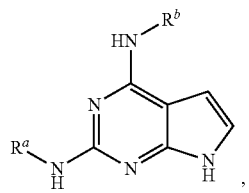

I-B

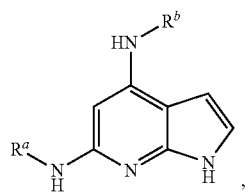

I-C or a pharmaceutically acceptable salt and/or solvate thereof;

wherein $R^a$ and $R^b$ are independently $C_3$-$C_8$ cycloalkyl, substituted $C_3$-$C_8$ cycloalkyl, phenyl, substituted phenyl, 5- to 7-membered heteroaryl, substituted 5- to 7-membered heteroaryl, 5- to 7-membered heterocycle, and substituted 5- to 7-membered heterocycle; and Y is CH or N.

In some aspects, $R^a$ is substituted phenyl and $R^b$ is $C_3$-$C_8$ cycloalkyl, substituted $C_3$-$C_8$ cycloalkyl or substituted phenyl. In some aspects, $R^a$ is substituted phenyl comprising at a 2-alkoxy substituent.

In another aspect, provided are methods of inhibiting Mps1/TTK comprising, consisting of or consisting essentially of, contacting Mps1/TTK with a compound of Formula II-A, II-B, II-C, III-A, III-B, or III-C:

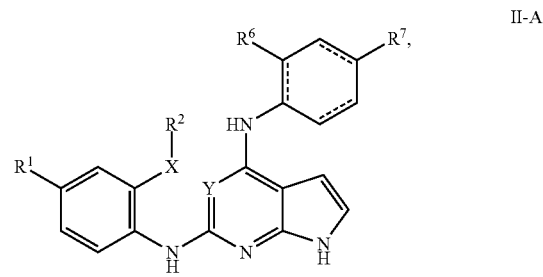

II-A

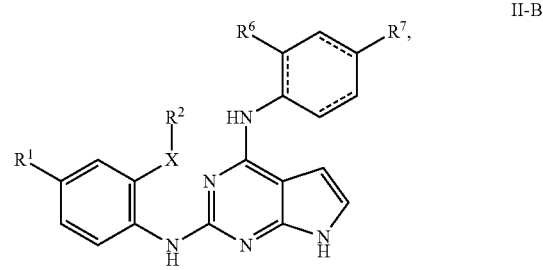

II-B

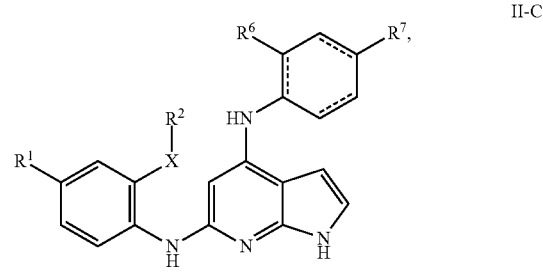

II-C

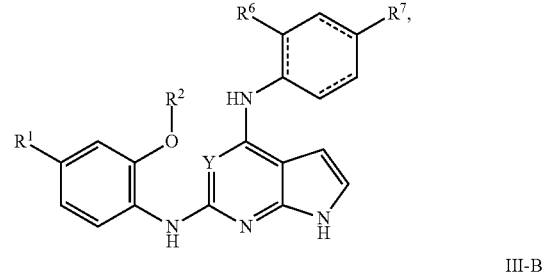

III-A

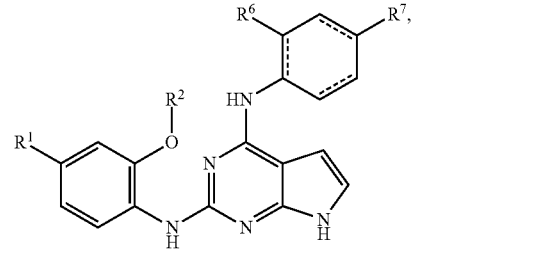

III-B

-continued

III-C
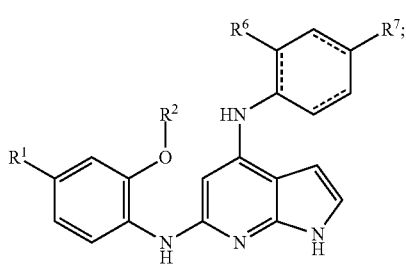

or a tautomer, a pharmaceutically acceptable salt and/or a solvate thereof;

wherein

X is O, S or $SO_2$;

Y is CH or N;

$R^1$ is selected from the group consisting of hydrogen, halo, —O—$R^{10}$, —C(O)—$R^{10}$, —$NR^{10}$C(O)$R^{13}$, —C(O)O—$R^{10}$, —$NR^{10}R^{13}$, —C(O)$NR^{10}R^{10}$, —C(S)$NR^{10}R^{11}$, —$NR^{13}$C(O)$NR^{10}R^{11}$, —$NR^{13}$C(S)$NR^{10}R^{11}$, —O—C(O)$NR^{10}R^{11}$, —S(O)$_2NR^{10}R^{11}$, —O—S(O)$_2NR^{10}R^{11}$, —$NR^{13}$—S(O)$_2NR^{10}R^{11}$, CN, $NO_2$, —S(O)$_2$—$R^{10}$ and 5- to 7-membered heterocycle optionally substituted with one or two oxo and/or $R^3$, wherein $R^3$ is independently selected from the group consisting of —O—$R^{10}$, —C(O)—$R^{10}$, —$NR^{10}$C(O)$R^{13}$, —C(O)O—$R^{10}$, —$NR^{10}R^{11}$, —C(O)$NR^{10}R^{11}$, —C(S)$NR^{10}R^{11}$, —$NR^{13}$C(O)$NR^{10}R^{11}$, —$NR^{13}$C(S)$NR^{10}R^{11}$, —O—C(O)$NR^{10}R^{11}$, —S(O)$_2NR^{10}R^{11}$, —O—S(O)$_2NR^{10}R^{11}$, —$NR^{13}$—S(O)$_2NR^{10}R^{11}$, CN, halo, $NO_2$, and —S(O)$_2$—$R^{12}$;

$R^2$ is selected from the group consisting of hydrogen, $C_1$-$C_3$ alkyl and $C_1$-$C_3$ haloalkyl; provided that when X is $SO_2$, or when $R^1$ is hydrogen, then $R^2$ is not hydrogen;

$R^6$ is selected from the group consisting of hydrogen, halo, —O—$R^{20}$, —C(O)—$R^{21}$, —C(O)O—$R^{20}$, —$NR^{20}R^{23}$, —C(O)$NR^{20}R^{21}$, —C(S)$NR^{20}R^{21}$, —$NR^{23}$C(O)$NR^{20}R^{21}$, —$NR^{23}$C(S)$NR^{20}R^{21}$, —O—C(O)$NR^{20}R^{21}$, —S(O)$_2NR^{20}R^{21}$, —O—S(O)$_2NR^{20}R^{21}$, —$NR^{23}$—S(O)$_2$ $NR^{20}R^{21}$, CN, $NO_2$, and —S(O)$_2$—$R^{20}$;

$R^7$ is selected from the group consisting of hydrogen, halo, —O—$R^{20}$, —C(O)—$R^{21}$, —C(O)O—$R^{20}$, —$NR^{20}R^{23}$, —C(O)$NR^{20}R^{21}$, —C(S)$NR^{20}R^{21}$, —$NR^{23}$C(O)$NR^{20}R^{21}$, —$NR^{23}$C(S)$NR^{20}R^{21}$, —O—C(O)$NR^{20}R^{21}$, —S(O)$_2R^{20}R^{21}$, —O—S(O)$_2NR^{20}R^{21}$, —$R^{23}$—S(O)$_2$ $NR^{20}R^{21}$, CN, $NO_2$, and —S(O)$_2$—$R^{22}$;

each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle;

or $R^{20}$ and $R^{21}$ together with the atom attached thereto form a 5- to 7-membered heterocycle;

each $R^{12}$ and $R^{22}$ is independently $C_1$-$C_6$ alkyl; and

==== represents a single bond or a double bond.

In some aspects, the compound is a compound of Formula VI-A, IV-B, IV-C, V-A, V-B, or V-C:

IV-A
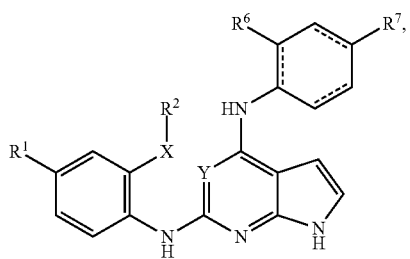

IV-B
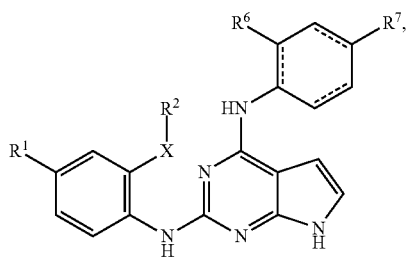

IV-C
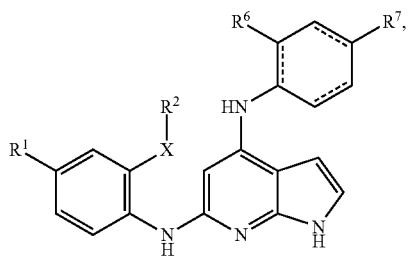

V-A
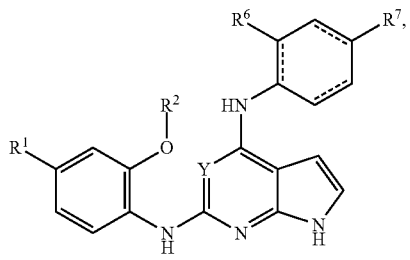

V-B
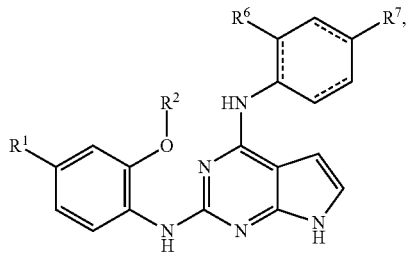

V-C
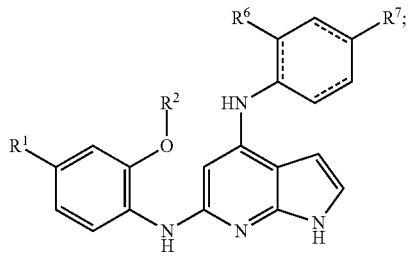

or a tautomer, a pharmaceutically acceptable salt and/or a solvate thereof;

wherein

X is O, S or SO$_2$;

Y is CH or N;

R$^1$ is selected from the group consisting of hydrogen and 5- to 7-membered heterocycle optionally substituted with one or two oxo and/or R$^3$, wherein R$^3$ is independently selected from the group consisting of —O—R$^{10}$, —NR$^{10}$C(O)R$^{12}$, —C(O)O—R$^{10}$, —NR$^{10}$R$^{11}$, —C(O)NR$^{10}$R$^{11}$, —C(S)NR$^{10}$R$^{11}$, —NR$^{13}$C(O)NR$^{10}$R$^{11}$, —NR$^{13}$C(S)NR$^{10}$R$^{11}$, —O—C(O)NR$^{10}$R$^{11}$, —S(O)$_2$NR$^{10}$R$^{11}$, —O—S(O)$_2$NR$^{10}$R$^{11}$, —NR$^{13}$—S(O)$_2$NR$^{10}$R$^{11}$, CN, halo, NO$_2$, and —S(O)$_2$—R$^{12}$;

R$^2$ is selected from the group consisting of hydrogen, C$_1$-C$_3$ alkyl and C$_1$-C$_3$ haloalkyl; provided that when X is SO$_2$, or when R$^1$ is hydrogen, then R$^2$ is not hydrogen;

R$^6$ is selected from the group consisting of hydrogen, halo, —O—R$^{20}$, —C(O)—R$^{20}$, —C(O)O—R$^{20}$, —NR$^{20}$R$^{21}$, —C(S)NR$^{20}$R$^{21}$, —NR$^{23}$C(O)NR$^{20}$R$^{21}$, —NR$^{23}$C(S) NR$^{20}$R$^{21}$, —O—C(O)NR$^{20}$R$^{21}$, —S(O)$_2$NR$^{20}$R$^{21}$, —O—S(O)$_2$NR$^{20}$R$^{21}$, —NR$^{23}$—S(O)$_2$NR$^{20}$R$^{21}$, CN, NO$_2$, C$_1$-C$_6$ alkyl and —S(O)$_2$—R$^{22}$;

R$^7$ is selected from the group consisting of hydrogen, halo, —O—R$^{20}$, —C(O)—R$^{20}$, —C(O)O—R$^{20}$, —NR$^{20}$R$^{21}$, —C(O)NR$^{20}$R$^{21}$, —C(S)NR$^{20}$R$^{21}$, —NR$^{23}$C(O) NR$^{20}$R$^{21}$, —NR$^{23}$C(S)NR$^{20}$R$^{21}$, —O—C(O)NR$^{20}$R$^{21}$, —S(O)$_2$NR$^{20}$R$^{21}$, —O—S(O)$_2$NR$^{20}$R$^{21}$, —NR$^{23}$—S(O)$_2$ NR$^{20}$R$^{21}$, CN, NO$_2$, C$_1$-C$_6$ alkyl and —S(O)$_2$—R$^{22}$;

each of R$^{10}$, R$^{11}$, R$^{13}$, R$^{20}$, R$^{21}$, and R$^{23}$ is independently hydrogen or C$_1$-C$_6$ alkyl; or R$^{10}$ and R$^{11}$ together with the atom attached thereto form a 5- to 7-membered heterocycle; or R$^{20}$ and R$^{21}$ together with the atom attached thereto form a 5- to 7-membered heterocycle;

R$^{12}$ and R$^{22}$ is independently C$_1$-C$_6$ alkyl; and

==== represents a single bond or a double bond.

In some embodiments, the compound is a compound of Formula VI

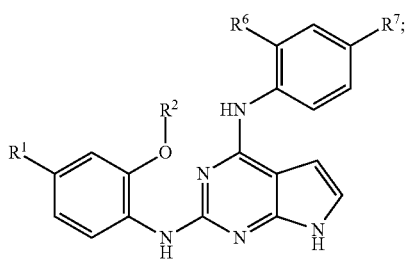

VI or a tautomer, a pharmaceutically acceptable salt and/or a solvate thereof, wherein R$^1$, R$^2$, R$^6$, and R$^7$ are defined as above.

In some embodiments, the compound of is a compound of Formula VII

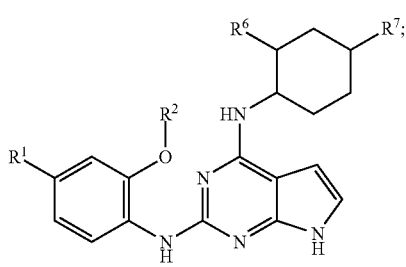

VII or a tautomer, a pharmaceutically acceptable salt and/or a solvate thereof, wherein R$^1$, R$^2$, R$^6$, and R$^7$ are defined as above.

In some embodiments, the compound is a compound of Formula VIII

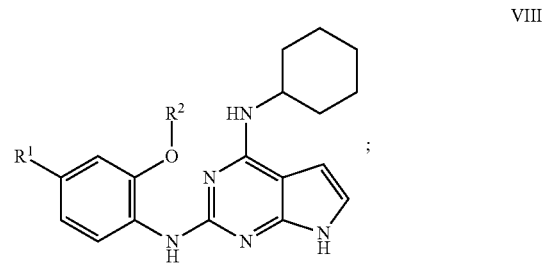

VIII or a tautomer, a pharmaceutically acceptable salt and/or a solvate thereof, wherein R$^1$ and R$^2$ are defined as above.

In some aspects of Formula II-A, II-B, II-C, III-A, III-B, III-C, IV-A, IV-B, IV-C, V-A, V-B, V-C, VI, VII or VIII, X is O. In some aspects, X is S. In some aspects, X is SO$_2$.

In some aspects of Formula II-A, II-B, II-C, III-A, III-B, III-C, IV-A, IV-B, IV-C, V-A, V-B, V-C, VI, VII or VIII, R$^3$ is selected from the group consisting of —O—R$^{10}$, —C(O)—R$^1$, —NR$^{10}$C(O)R$^{12}$, —C(O)O—R$^{10}$, —NR$^{10}$R$^{13}$, —C(O)NR$^{10}$R$^{11}$, —C(S)NR$^{10}$R$^{11}$, —NR$^{13}$C (O)NR$^{10}$R$^{11}$, —NR$^{13}$C(S)NR$^{10}$R$^{11}$, —O—C(O)NR$^{10}$R$^{11}$, —S(O)$_2$NR$^{10}$R$^{11}$, —O—S(O)$_2$NR$^{10}$R$^{11}$, —NR$^{13}$—S(O)$_2$ NR$^{10}$R$^{11}$, CN, halo, NO$_2$, and —S(O)$_2$—R$^{12}$.

In some aspects of Formula II-A, II-B, II-C, III-A, III-B, III-C, IV-A, IV-B, IV-C, V-A, V-B, V-C, VI, VII or VIII, R$^3$ is selected from the group consisting of —NR$^{10}$C(O)R$^{12}$, —C(O)O—R$^{10}$, —NR$^{10}$R$^{13}$, —C(O)NR$^{10}$R$^{11}$, —C(S) NR$^{10}$R$^{11}$, —NR$^{13}$C(O)NR$^{10}$R$^{11}$, —NR$^{13}$C(S)NR$^{10}$R$^{11}$, —O—C(O)NR$^{10}$R$^{11}$, and —O—S(O)$_2$NR$^{10}$R$^{11}$.

In some aspects of Formula II-A, II-B, II-C, III-A, III-B, III-C, IV-A, IV-B, IV-C, V-A, V-B, V-C, VI, VII or VIII, R$^3$ is selected from the group consisting of —O—R$^{10}$, —NR$^{10}$C(O)R$^{12}$, —C(O)O—R$^{10}$, —NR$^{10}$R$^{11}$, —C(O) NR$^{10}$R$^{11}$, —NR$^{13}$C(O)NR$^{10}$R$^{11}$, —O—C(O)NR$^{10}$R$^{11}$, —NR$^{13}$—S(O)$_2$NR$^{10}$R$^{11}$, CN, halo, and —S(O)$_2$—R$^{12}$.

In some aspects of Formula II-A, II-B, II-C, III-A, III-B, III-C, IV-A, IV-B, IV-C, V-A, V-B, V-C, VI, VII or VIII, R$^3$ is selected from the group consisting of —O—R$^{10}$, —NR$^{10}$C(O)R$^{12}$, —NR$^{10}$R$^{11}$, —NR$^{13}$C(O)NR$^{10}$R$^{11}$, —O—C(O)NR$^{10}$R$^{11}$, and —NR$^{13}$—S(O)$_2$NR$^{10}$R$^{11}$.

In some aspects of Formula II-A, II-B, II-C, III-A, III-B, III-C, IV-A, IV-B, IV-C, V-A, V-B, V-C, VI, VII or VIII, R$^3$ is selected from the group consisting of —O—R$^{10}$ and —O—C(O)NR$^{10}$R$^{11}$.

In some aspects of Formula II-A, II-B, II-C, III-A, III-B, III-C, IV-A, IV-B, IV-C, V-A, V-B, V-C, VI, VII or VIII, R$^3$ is —O—R$^{10}$.

In some aspects of Formula II-A, II-B, II-C, III-A, III-B, III-C, IV-A, IV-B, IV-C, V-A, V-B, V-C, VI, VII or VIII, R$^1$ is hydrogen.

In some aspects of Formula II-A, II-B, II-C, III-A, III-B, III-C, IV-A, IV-B, IV-C, V-A, V-B, V-C, VI, VII or VIII, R$^1$ is a 5- to 7-membered heterocycle.

In some aspects of Formula II-A, II-B, II-C, III-A, III-B, III-C, IV-A, IV-B, IV-C, V-A, V-B, V-C, VI, VII or VIII, R$^1$ is 5- to 7-membered heterocycle selected from the group consisting of pyrrolidine, oxazolidine, isoxazolidine, thiazolidine, imidazolidine, piperidine, morpholine, piperazine, thiomorpholine, diazepane, 1,4-diazapane, oxazepane, 1,4-oxazepane, thiazepane, and 1,4-thiazepane, wherein the 5- to 7-membered heterocycle is optionally substituted with $R^3$. In some embodiments, $R^3$ is independently selected from the group consisting of —O—$R^{10}$ and —O—C(O)N$R^{10}R^{11}$.

In some aspects of Formula II-A, II-B, II-C, III-A, III-B, III-C, IV-A, IV-B, IV-C, V-A, V-B, V-C, VI, VII or VIII, $R^1$ is selected from the group consisting of

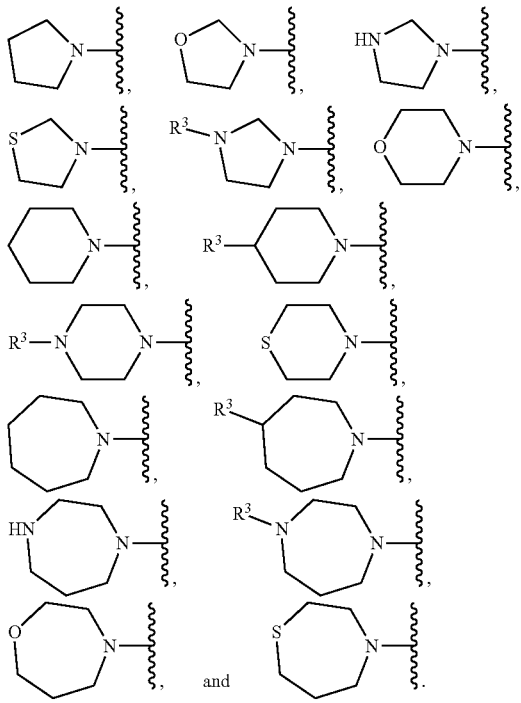

In some aspects of Formula II-A, II-B, II-C, III-A, III-B, III-C, IV-A, IV-B, IV-C, V-A, V-B, V-C, VI, VII or VIII, $R^1$ is selected from the group consisting of

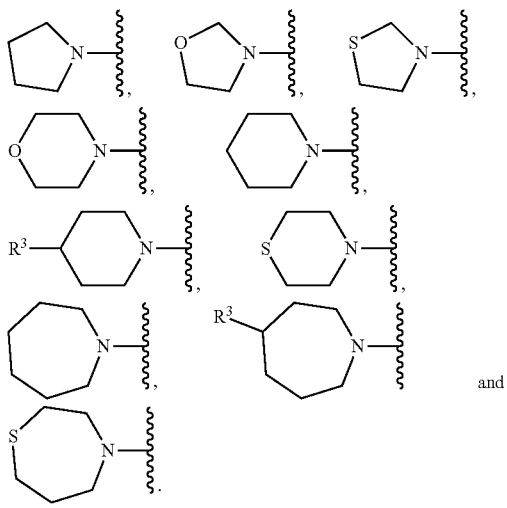

In some aspects of Formula II-A, II-B, II-C, III-A, III-B, III-C, IV-A, IV-B, IV-C, V-A, V-B, V-C, VI, VII or VIII, $R^3$ is OH.

In some aspects of Formula II-A, II-B, II-C, III-A, III-B, III-C, IV-A, IV-B, IV-C, V-A, V-B, V-C, VI, VII or VIII, $R^6$ is selected from the group consisting of hydrogen, halo, —O—$R^{20}$, —C(O)—$R^{20}$, —C(O)O—$R^{20}$, —N$R^{20}R^{21}$, —N$R^{23}$C(O)N$R^{20}R^{21}$, —O—C(O)N$R^{20}R^{21}$, —S(O)$_2$N$R^{20}R^{21}$, CN, $C_1$-$C_6$ alkyl and —S(O)$_2$—$R^{22}$.

In some aspects of Formula II-A, II-B, II-C, III-A, III-B, III-C, IV-A, IV-B, IV-C, V-A, V-B, V-C, VI, VII or VIII, $R^6$ is selected from the group consisting of hydrogen, halo, —C(O)—$R^{20}$, —C(O)O—$R^{20}$, —S(O)$_2$N$R^{20}R^{21}$, CN, and —S(O)$_2$—$R^{22}$.

In some aspects of Formula II-A, II-B, II-C, III-A, III-B, III-C, IV-A, IV-B, IV-C, V-A, V-B, V-C, VI, VII or VIII, $R^6$ is selected from the group consisting of hydrogen, and —S(O)$_2$—$R^{22}$.

In some aspects of Formula II-A, II-B, II-C, III-A, III-B, III-C, IV-A, IV-B, IV-C, V-A, V-B, V-C, VI, VII or VIII, $R^7$ is selected from the group consisting of hydrogen, halo, —C(O)—$R^{20}$, —C(O)O—$R^{20}$, —C(O)N$R^{20}R^{21}$, —S(O)$_2$N$R^{20}R^{21}$, CN, NO$_2$, and —S(O)$_2$—$R^{22}$.

In some aspects of Formula II-A, II-B, II-C, III-A, III-B, III-C, IV-A, IV-B, IV-C, V-A, V-B, V-C, VI, VII or VIII, $R^7$ is selected from the group consisting of hydrogen, halo, —C(O)—$R^{20}$, —C(O)O—$R^{20}$, —C(O)N$R^{20}R^{21}$, and CN.

In some aspects of Formula II-A, II-B, II-C, III-A, III-B, III-C, IV-A, IV-B, IV-C, V-A, V-B, V-C, VI, VII or VIII, $R^7$ is selected from the group consisting of hydrogen, and —C(O)N$R^{20}R^{21}$.

In some aspects of Formula II-A, II-B, II-C, III-A, III-B, III-C, IV-A, IV-B, IV-C, V-A, V-B, V-C, VI, VII or VIII, $R^6$ is hydrogen and $R^7$ is —C(O)N$R^{20}R^{21}$.

In some aspects of Formula II-A, II-B, II-C, III-A, III-B, III-C, IV-A, IV-B, IV-C, V-A, V-B, V-C, VI, VII or VIII, $R^6$ is —S(O)$_2$—$R^{22}$ and $R^7$ is hydrogen.

In some aspects of Formula II-A, II-B, II-C, III-A, III-B, III-C, IV-A, IV-B, IV-C, V-A, V-B, V-C, VI, VII or VIII, $R^2$ is $C_1$-$C_3$ alkyl, such as methyl. In some aspects of Formula II-A, II-B, II-C, III-A, III-B, III-C, IV-A, IV-B, IV-C, V-A, V-B, V-C, VI, or VII, $R^6$ is —S(O)$_2$—$R^{22}$. In some embodiments, $R^6$ is hydrogen. In some aspects of Formula II-A, II-B, II-C, III-A, III-B, III-C, IV-A, IV-B, IV-C, V-A, V-B, V-C, VI, VII or VIII, $R^7$ is —C(O)N$R^{20}R^{21}$. In some aspects, $R^7$ is hydrogen.

In some aspects of Formula II-A, II-B, II-C, III-A, III-B, III-C, IV-A, IV-B, IV-C, V-A, V-B, V-C, VI, VII or VIII, $R^1$ is hydrogen, $R^2$ is $C_1$-$C_6$ alkyl, such as methyl, $R^6$ is —S(O)$_2$—$R^{22}$, and $R^7$ is hydrogen. In some aspects, $R^6$ is —SO$_2$CH(CH$_3$)$_2$.

In some aspects of Formula II-A, II-B, II-C, III-A, III-B, III-C, IV-A, IV-B, IV-C, V-A, V-B, V-C, VI, or VII, $R^1$ is morpholinyl, $R^2$ is $C_1$-$C_6$ alkyl, such as methyl, $R^6$ is —S(O)$_2$—$R^{22}$, and $R^7$ is hydrogen. In some aspects of Formula II-A, II-B, II-C, III-A, III-B, III-C, IV-A, IV-B, IV-C, V-A, V-B, V-C, VI, or VII, $R^6$ is —SO$_2$CH(CH$_3$)$_2$.

In some aspects of Formula II-A, II-B, II-C, III-A, III-B, III-C, IV-A, IV-B, IV-C, V-A, V-B, V-C, VI, or VII, $R^1$ is piperidinyl optionally substituted with OH, $R^2$ is $C_1$-$C_6$ alkyl, such as methyl, $R^6$ is —S(O)$_2$—$R^{22}$, and $R^7$ is hydrogen. In some aspects, $R^6$ is —SO$_2$CH(CH$_3$)$_2$.

In some aspects of Formula II-A, II-B, II-C, III-A, III-B, III-C, IV-A, IV-B, IV-C, V-A, V-B, V-C, VI, or VII, $R^1$ is hydrogen, $R^2$ is $C_1$-$C_6$ alkyl, such as methyl, $R^6$ is hydrogen, and $R^7$ is —C(O)N$R^{20}R^{21}$, such as —C(O)NHCH(CH$_3$)$_2$.

In some aspects of Formula II-A, II-B, II-C, III-A, III-B, III-C, IV-A, IV-B, IV-C, V-A, V-B, V-C, VI, or VII, $R^1$ is morpholinyl, $R^2$ is $C_1$-$C_6$ alkyl, such as methyl, $R^6$ is hydrogen, and $R^7$ is —C(O)NR$^{20}$R$^{21}$, such as —C(O)NHCH(CH$_3$)$_2$.

In some aspects of Formula II-A, II-B, II-C, III-A, III-B, III-C, IV-A, IV-B, IV-C, V-A, V-B, V-C, VI, or VII, $R^1$ is piperidinyl optionally substituted with $R^3$, such as OH, $R^2$ is $C_1$-$C_6$ alkyl, such as methyl, $R^6$ is hydrogen, and $R^7$ is —C(O)NR$^{20}$R$^{21}$, such as —C(O)NHCH(CH$_3$)$_2$.

In some aspects of Formula II-A, II-B, II-C, III-A, III-B, III-C, IV-A, IV-B, IV-C, V-A, V-B, V-C, VI, or VII, the compound is selected from:

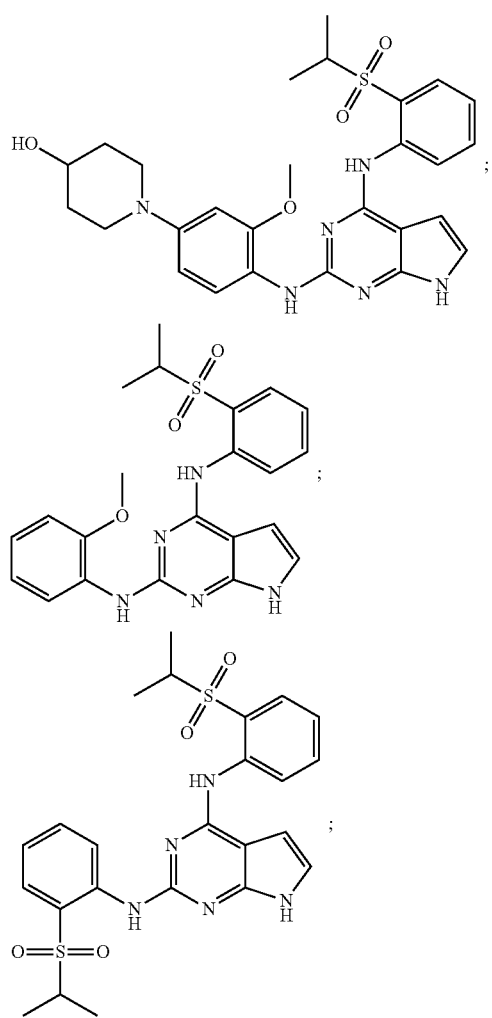

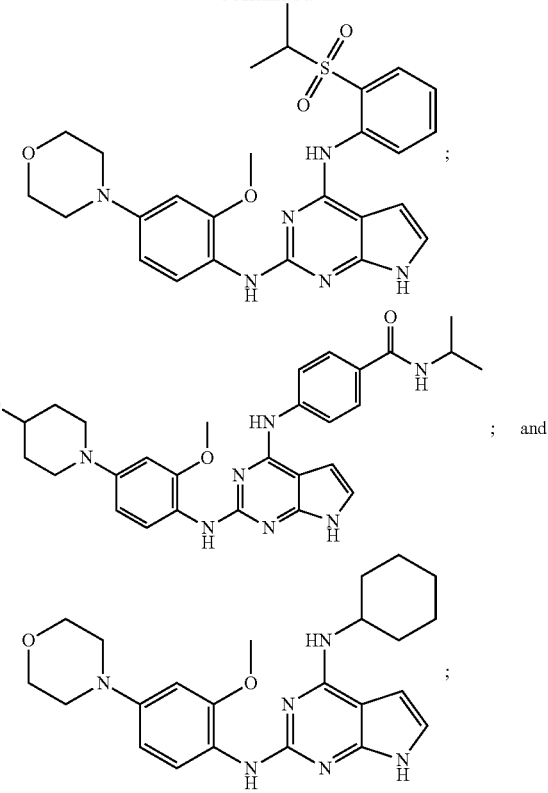

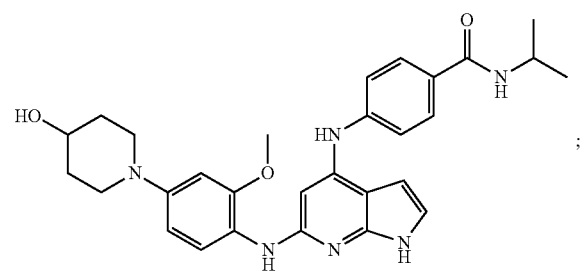

or a tautomer, a pharmaceutically acceptable salt and/or a solvate thereof. In some aspects of Formula II-A, II-B, II-C, III-A, III-B, III-C, IV-A, IV-B, IV-C, V-A, V-B, V-C, VI, or VII, the compound is 1-(4-((4-((2-(isopropylsulfonyl)phenyl)amino)-7H-pyrrolo[2,3-d]pyrimidin-2-yl)amino)-3-methoxyphenyl)piperidin-4-ol, or a tautomer, a pharmaceutically acceptable salt and/or a solvate thereof. In some aspects of Formula II-A, II-B, II-C, III-A, III-B, III-C, IV-A, IV-B, IV-C, V-A, V-B, V-C, VI, or VII, the compound is N4-(2-(isopropylsulfonyl)phenyl)-N2-(2-methoxyphenyl)-7H-pyrrolo-[2,3-d]pyrimidine-2,4-diamine, or a tautomer, a pharmaceutically acceptable salt and/or a solvate thereof. In some aspects of Formula II-A, II-B, II-C, III-A, III-B, III-C, IV-A, IV-B, IV-C, V-A, V-B, V-C, VI, or VII, the compound is N4-(2-(isopropylsulfonyl)phenyl)-N2-(2-methoxy-4-morpholinophenyl)-7H-pyrrolo[2,3-d]pyrimidine-2,4-diamine, or a tautomer, a pharmaceutically acceptable salt and/or a solvate thereof. In some aspects of Formula II-A, II-B, II-C, III-A, III-B, III-C, IV-A, IV-B, IV-C, V-A, V-B, V-C, VI, or VII, the compound is N4-cyclohexyl-N2-(2-methoxy-4-morpholinophenyl)-7H-pyrrolo[2,3-d]pyrimidine-2,4-diamine, or a tautomer, a pharmaceutically acceptable salt and/or a solvate thereof.

In one aspect, provided are methods of treating a disease mediated in part by Mps1/TTK, comprising, consisting of or consisting essentially of, administering a therapeutically effective amount of a compound described herein, such as a compound of Formula I-A, I-B, I—C, II-A, II-B, II-C, III-A, III-B, III-C, IV-A, IV-B, IV-C, V-A, V-B, V-C, VI, VII or VIII, or a tautomer, and/or a pharmaceutically acceptable salt and/or solvate thereof, to a patient in need thereof. In some aspects, the disease mediated in part by Mps1/TTK is correlated with the presence in the patient of cells that over express protein kinase Mps1/TTK, such as expressing Mps1/TTK at a level that is at least 120%, 150%, or 200% of the normal Mps1/TTK expression level. The normal Mps1/TTK expression level can be determined by Mps1/TTK expression levels of healthy individuals using methods known in the art.

In one aspect, provided are methods of treating a disease mediated at least in part by protein kinase Mps1 in a patient in need thereof, which method comprising administering to the patient a therapeutically effective amount of a compound of Formula I-A

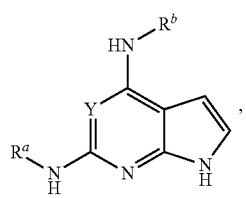

I-A or a pharmaceutically acceptable salt and/or solvate thereof; wherein $R^a$ and $R^b$ are independently $C_3$-$C_8$ cycloalkyl, substituted $C_3$-$C_8$ cycloalkyl, phenyl, substituted phenyl, 5- to 7-membered heteroaryl, substituted 5- to 7-membered heteroaryl, 5- to 7-membered heterocycle, and substituted 5- to 7-membered heterocycle; and Y is CH or N. In some embodiments, Y is N. In some embodiments, Y is CH. In some embodiments, the compound is a compound of Formula II-A or III-A, or a tautomer, a pharmaceutically acceptable salt and/or a solvate thereof. In some embodiments, the disease is breast cancer. In some embodiments, the disease is triple negative breast cancer.

In one aspect, provided are methods of treating a cancer, in particular breast cancer, comprising, consisting of or consisting essentially of, administering a therapeutically effective amount of a compound described herein, such as a compound of Formula I-A, I-B, I-C, II-A, II-B, II-C, III-A, III-B, III-C, IV-A, IV-B, IV-C, V-A, V-B, V-C, VI, VII or VIII, or a pharmaceutically acceptable salt and/or solvate thereof, to a patient in need thereof. In some aspects, the cancer is an invasive breast cancer. In some aspects, the cancer is an aggressive breast cancer. In some aspects, the cancer is a triple negative breast cancer. In some aspects, the cancer comprises, consisting of or consisting essentially of, cells that over express protein kinase Mps1/TTK, such as expressing Mps1/TTK at a level that is at least 120%, 150%, or 200% of the normal Mps1/TTK expression level. The normal Mps1/TTK expression level can be determined by Mps1/TTK expression levels of healthy individuals using methods known in the art.

In another aspect, provided are compounds for use in the treatment of cancer, in particular breast cancer. In some embodiments, the compounds are compounds of Formula I-A, I-B, I-C, II-A, II-B, II-C, III-A, III-B, III-C, IV-A, IV-B, IV-C, V-A, V-B, V-C, VI, VII or VIII, or a pharmaceutically acceptable salt and/or solvate thereof. In some embodiments, the cancer is an invasive breast cancer. In some embodiments, the cancer is an aggressive breast cancer. In some aspects, the cancer is a triple negative breast cancer. In some embodiments, the cancer comprises, consisting of or consisting essentially of, cells that over express protein kinase Mps1/TTK, such as expressing Mps1/TTK at a level that is at least 120%, 150%, or 200% of the normal Mps1/TTK expression level. The normal Mps1/TTK expression level can be determined by Mps1/TTK expression levels of healthy individuals using methods known in the art.

In another aspect, provided are uses of compounds described herein for the manufacture of a medicament for use in treatment of cancer, in particular breast cancer. In some embodiments, the compounds are compounds of Formula I-A, I-B, I-C, II-A, II-B, II-C, III-A, III-B, III-C, IV-A, IV-B, IV-C, V-A, V-B, V-C, VI, VII or VIII, or a pharmaceutically acceptable salt and/or solvate thereof. In some embodiments, the cancer is an invasive breast cancer. In some embodiments, the cancer is an aggressive breast cancer. In some aspects, the cancer is a triple negative breast cancer. In some embodiments, the cancer comprises, consisting of or consisting essentially of, cells that over express protein kinase Mps1/TTK, such as expressing Mps1/TTK at a level that is at least 120%, 150%, or 200% of the normal Mps1/TTK expression level. The normal Mps1/TTK expression level can be determined by Mps1/TTK expression levels of healthy individuals using methods known in the art.

In another aspect, provided are uses of a compound described herein for the treatment of cancer, in particular breast cancer. In some embodiments, the compound is a compound of Formula I-A, I-B, I-C, II-A, II-B, II-C, III-A, III-B, III-C, IV-A, IV-B, IV-C, V-A, V-B, V-C, VI, VII or VIII, or a pharmaceutically acceptable salt and/or solvate thereof. In some embodiments, the cancer is an invasive breast cancer. In some embodiments, the cancer is an aggressive breast cancer. In some aspects, the cancer is a triple negative breast cancer. In some embodiments, the cancer comprises, consisting of or consisting essentially of, cells that over express protein kinase Mps1/TTK, such as expressing Mps1/TTK at a level that is at least 120%, 150%, or 200% of the normal Mps1/TTK expression level. The normal Mps1/TTK expression level can be determined by Mps1/TTK expression levels of healthy individuals using methods known in the art.

Methods for determining the presence and level of Mps1/TTK protein and/or mRNA are known in the art, such as those described in Kasbek C, et al. 2010. Antizyme Restrains Centrosome Amplification by Regulating the Accumulation of Mps1 at Centrosomes. *Molecular Biology of the Cell* 21:3879-89; and Mills G B, et al. 1992. Expression of TTK, a Novel Human Protein-Kinase, Is Associated with Cell-Proliferation. *Journal of Biological Chemistry* 267:16000-6.

In a still further aspect, provided is a method of treating a patient in need of an inhibitor of protein kinase Mps1/TTK, which method comprises, consists of or consists essentially of, determining the level of Mps1/TTK protein and/or mRNA in a cell, such as a cancer cell, of the patient; and administering a therapeutically effective amount of a compound of Formula I-A, I-B, I-C, II-A, II-B, II-C, III-A, III-B, III-C, IV-A, IV-B, IV-C, V-A, V-B, V-C, VI, VII or VIII, or a tautomer, and/or a pharmaceutically acceptable salt and/or solvate thereof, to the patient if the presence of Mps1/TTK protein and/or mRNA is detected. In some embodiments, the compound is a compound of Formula I-A, or a tautomer, and/or a pharmaceutically acceptable salt and/or solvate thereof. In further embodiments, Y is N. In further embodiments, Y is CH.

In some aspects, the patient is administered a compound described herein after detection of an over-expression of Mps1/TTK in a cell of the patient, such as an expression of Mps1/TTK that is at least 120%, 150%, or 200% of the normal Mps1/TTK expression level.

In some aspects, the patient is a breast cancer patient.

In a still further aspect, provided is a method of treating a patient in need of an inhibitor of protein kinase Mps1/TTK, which method comprises, consists of or consists essentially of, determining the triple negative status of a breast cancer patient in a cancer cell of the patient; and administering a therapeutically effective amount of a compound of Formula I-A, I-B, I-C, II-A, II-B, II-C, III-A, III-B, III-C, IV-A, IV-B, IV-C, V-A, V-B, V-C, VI, VII or VIII, or a tautomer, and/or a pharmaceutically acceptable salt and/or solvate thereof, to the patient if the cancer cell is triple negative status. In some embodiments, the compound is a compound of Formula I-A, or a tautomer, and/or a pharmaceutically acceptable salt and/or solvate thereof. In further embodiments, Y is N. In further embodiments, Y is CH.

In any of the embodiments of the methods described herein, the method may involve administration of a pharmaceutical composition, where the pharmaceutical composition includes any one of the embodiments of the compounds of the present technology or a pharmaceutically acceptable salt thereof as well as a pharmaceutically acceptable carrier or excipient.

In any of the embodiments of the methods described herein, the method may involve administration of a pharmaceutical composition, where the pharmaceutical composition includes an effective amount of any one of the embodiments of the compounds of the present technology or a pharmaceutically acceptable salt thereof and a pharmaceutically acceptable carrier or excipient. In some embodiments, the effective amount is from about 0.01 µg to about 900 mg of the compound per gram of the composition. In some embodiments, the effective amount is from about 0.01 µg to about 800 mg of the compound per gram of the composition. In some embodiments, the effective amount is from about 0.01 µg to about 700 mg of the compound per gram of the composition. In some embodiments, the effective amount is from about 0.01 µg to about 600 mg of the compound per gram of the composition. In some embodiments, the effective amount is from about 0.01 µg to about 500 mg of the compound per gram of the composition. In some embodiments, the effective amount is from about 0.01 µg to about 400 mg of the compound per gram of the composition. In some embodiments, the effective amount is from about 0.01 µg to about 300 mg of the compound per gram of the composition. In some embodiments, the effective amount is from about 0.01 µg to about 200 mg of the compound per gram of the composition. In some embodiments, the effective amount is from about 0.01 µg to about 100 mg of the compound per gram of the composition. In some embodiments, the effective amount is from about 0.1 µg to about 500 µg of the compound per gram of the composition.

In some embodiments, the effective amount of the compound is 0.5, 1, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 mg or more, including increments therein. In some embodiments, the effective amount of the compound is from about 10 mg to about 500 mg. In some embodiments, the compositions per unit dosage contain from about 0.1% to about 99% of the compound. In some embodiments, the compositions per unit dosage contain from about 10% to about 60% of the compound.

In some aspects, provided is a kit comprising, consisting essentially of, or consisting of an effective amount of a compound described herein such as any one of Formula I-A, I-B, I-C, II-A, II-B, II-C, III-A, III-B, III-C, IV-A, IV-B, IV-C, V-A, V-B, V-C, VI, VII or VIII, and optionally instructions for use. In some aspects, the instructions comprise, consist essentially of, or consist of a description of a method of treatment as described herein.

General Synthetic Methods

In one aspect, the invention relates to methods of preparing the compounds described herein.

The compounds can be prepared from readily available starting materials using methods described herein and known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials are generally known compounds or can be prepared by known procedures or obvious modifications thereof. For example, many of the starting materials, such as amino acids, are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Schemes 1 and 2 exemplify methods for preparing the compounds described herein. In Scheme 1, the starting material 2,4-dichloro-7H-pyrrolo[2,3-d]pyrimidine (30) and 4,6-dichloro-1H-pyrrolo[2,3-b]pyridine (available at, e.g., VWR International LLC), respectively. In Scheme 1, 2,4-Dichloro-7H-pyrrolo[2,3-d]pyrimidine is first protected by a suitable protecting group Pg by reacting with Pg-Lg (Lg is a leaving group, such as halo) to give Compound 1-A. In some aspects, Pg is Boc and Pg-Lg is Boc$_2$O. Compound 1-A is then subjected to sequential nucleophilic aromatic substitutions by reactions with starting materials Compounds B and D followed by deprotection afforded the compound of Formula B or I, wherein $R^1$, $R^2$, $R^3$, X, m and n are as defined in Formula II-B, respectively. The reactions of Scheme 2 are similar to those of Scheme 1. Compounds of Formula I-B or I—C can be prepared similarly by replacing starting materials Compounds B and D with $R^b$—NH$_2$ and $R^a$—NH$_2$, respectively.

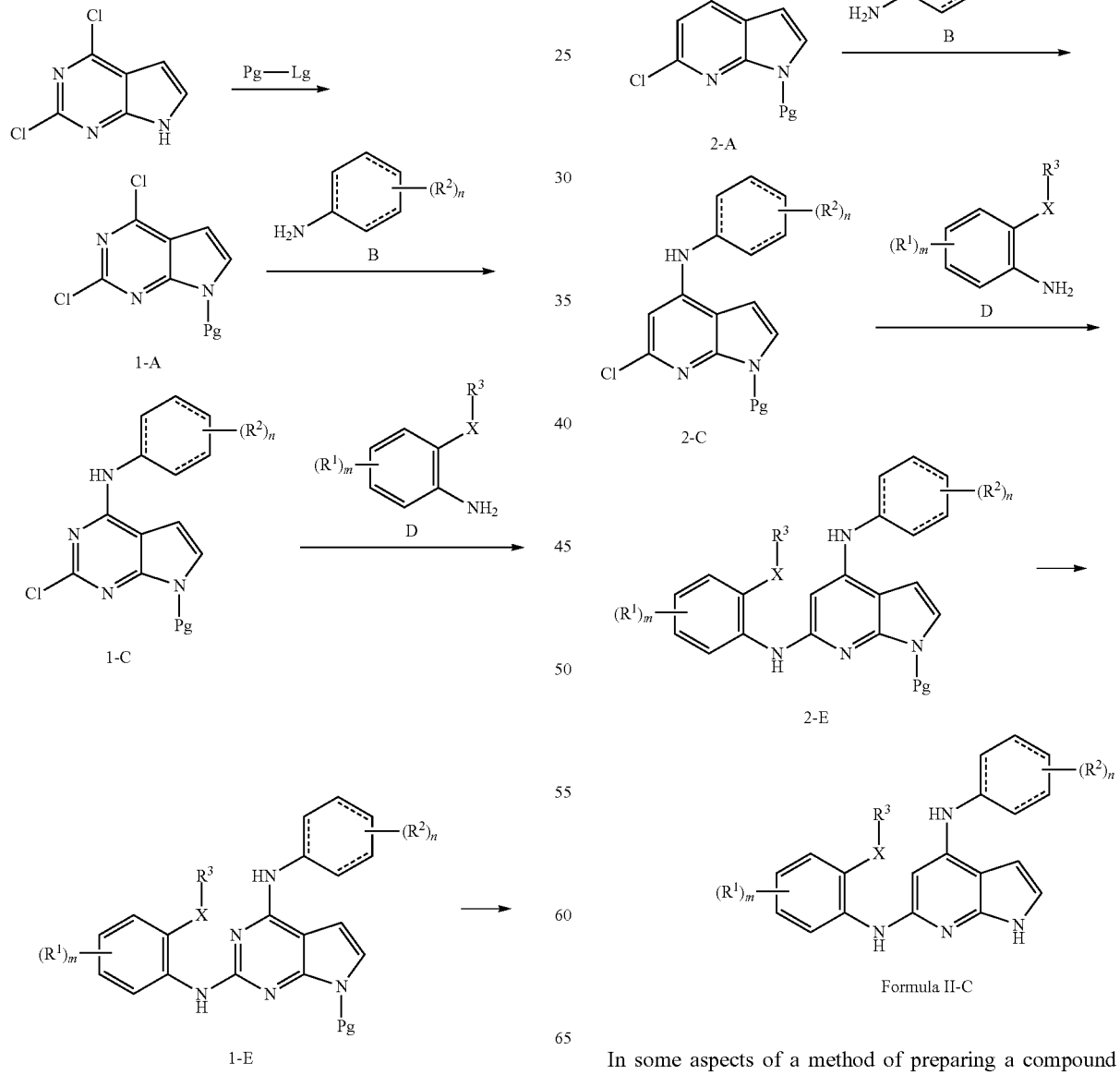

In some aspects of a method of preparing a compound described herein, or a tautomer, a pharmaceutically acceptable salt and/or a solvate thereof, the method comprises reacting a 2,4-dihalo-7H-pyrrolo[2,3-d]pyrimidine or an N-protected 2,4-dihalo-7H-pyrrolo[2,3-d]pyrimidine with an optionally substituted aryl amine or an optionally substituted cycloalkyl amine. In some embodiments, the 2,4-dihalo-7H-pyrrolo[2,3-d]pyrimidine is 2,4-dichloro-7H-pyrrolo[2,3-d]pyrimidine. In some embodiments, the 2,4-dihalo-7H-pyrrolo[2,3-d]pyrimidine is 2,4-dibromo-7H-pyrrolo[2,3-d]pyrimidine. In some embodiments, the 2,4-dihalo-7H-pyrrolo[2,3-d]pyrimidine is 2-bromo-4-chloro-7H-pyrrolo[2,3-d]pyrimidine. In some embodiments, the 2,4-dihalo-7H-pyrrolo[2,3-d]pyrimidine is 2-chloro-4-bromo-7H-pyrrolo[2,3-d]pyrimidine. In some embodiments, the N-protected 2,4-dihalo-7H-pyrrolo[2,3-d]pyrimidine is a Boc-protected 2,4-dihalo-7H-pyrrolo[2,3-d]pyrimidine. In some embodiments, the N-protected 2,4-dihalo-7H-pyrrolo[2,3-d]pyrimidine is tert-butyl 2,4-dichloro-7H-pyrrolo[2,3-d]pyrimidine-7-carboxylate.

EXAMPLES

Example 1

This example describes the development of novel small molecule Mps1/TTK inhibitors as targeted therapies for TNBC and other aggressive BC using drug discovery technologies. Using computational modeling, medicinal chemistry, biochemistry and cell culture assays, the inventors have identified novel small molecules as potential Mps1/TTK inhibitors. The compounds were evaluated in anti-proliferative assays of a panel of 15 BC cell lines and further examined for their ability to inhibit a variety of Mps1-dependent biological functions. Preliminary data indicated that the compounds have strong anti-proliferative potential through Mps1/TTK inhibition in triple negative BC and other aggressive BC cell lines, exhibiting $IC_{50}$ values ranging from 0.35 to 1.0 µM. In addition, the compounds inhibit Mps1 kinase enzymatic activity with $IC_{50}$ values from 30 nM to 155 nM.

1) Computational Drug Design:

AutoDock version 4.0.0 was used for the docking simulation. The Lamarckian genetic algorithm (LGA) for ligand conformational searching was selected because it has enhanced performance relative to simulated annealing or the simple genetic algorithm. For all compounds, all hydrogens were added and Gasteiger charges were assigned, then non-polar hydrogens were merged. 80×100×70 3-D affinity grids centered on the empty binding site with 0.375 Å spacing were calculated for each of the following atom types: a) protein: A (aromatic C), C, HD, N, NA, OA, SA; b) ligand: C, A, OA, HD, NA, SA, e (electrostatic) and d (desolvation) using Autogrid4. The ligand's translation, rotation and internal torsions are defined as its state variables and each gene represents a state variable. LGA adds local minimization to the genetic algorithm, enabling modification of the gene population. The docking parameters were as follows: trials of 100 dockings, population size of 250, random starting position and conformation, translation step ranges of 2.0 Å, rotation step ranges of 50°, elitism of 1, mutation rate of 0.02, crossover rate of 0.8, local search rate of 0.06, and 100 million energy evaluations. Final docked conformations were clustered using a tolerance of 1.5 Å root-mean-square deviations (RMSD).

In silico analysis of the scaffold identified twin hydrogen bonds between the novel chemical scaffold, a pyrrolopyrimidine ring, and the kinase hinge loop, which, not wishing to be bound by any theories, are contemplated to impart strong inhibitor binding (FIG. 1).

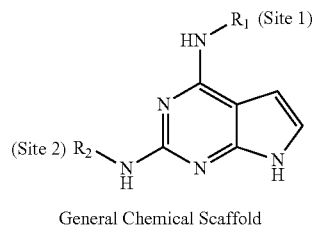

General Chemical Scaffold

Fragments were added into Site 1 to gain potency and selectivity and fragments were replaced at Site 2 to gain potency and improve drug properties. Site 1 is a particularly attractive site for modifications as this site is not occupied by substituents in current inhibitors. Site 2 affords opportunities for fragment substitutions that will enhance pharmacokinetic parameters.

The study led to development of the following compounds as Mps1/TTK inhibitors.

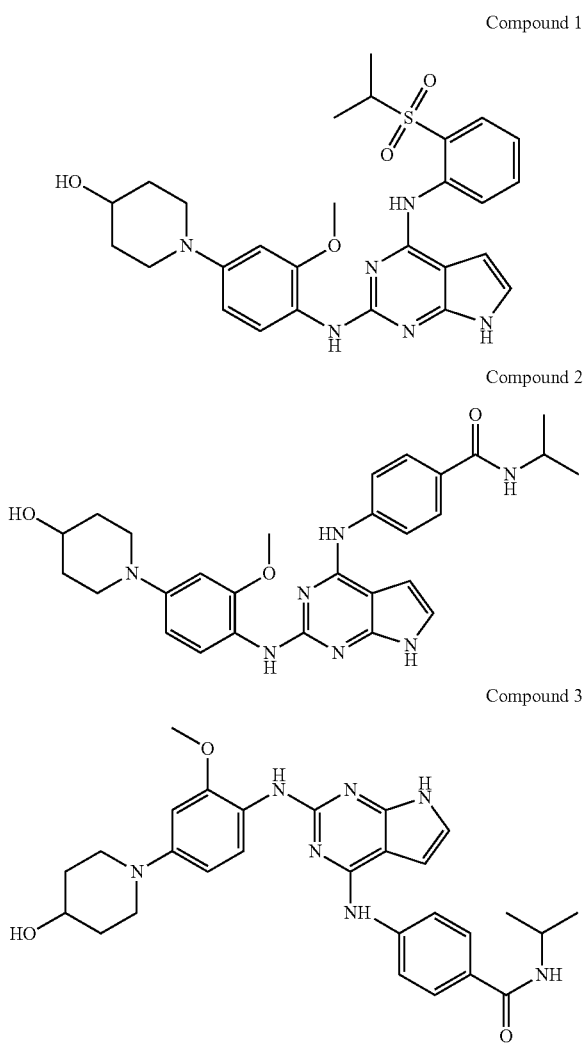

Compound 9

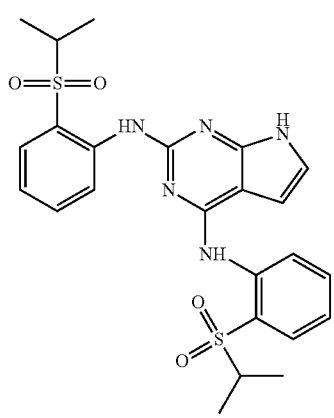

Compound 10

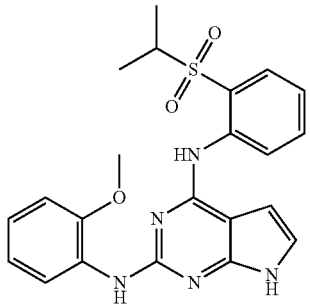

Compound 11

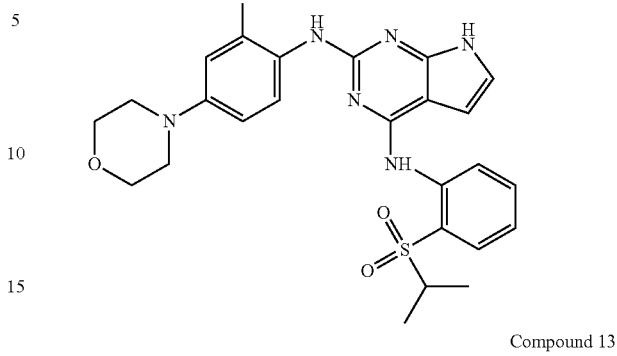

Compound 13

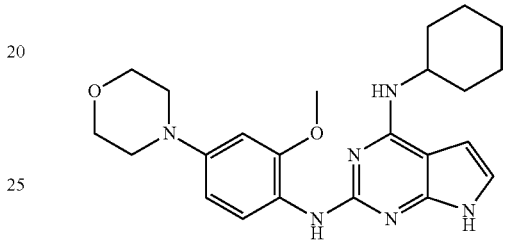

2) Synthesis of the Inhibitors:

The synthesis of compound 1 is shown in Scheme 3. The synthesis began with the known compound 2,4-dichloro-7H-pyrrolo[2,3-d]pyrimidine (30). Sequential nucleophilic aromatic substitutions with the respective groups on site 1 and 2 followed by deprotection afforded compound 1. Compounds 2, 10 and 13 were synthesized in a similar manner as compound 1.

Scheme 3

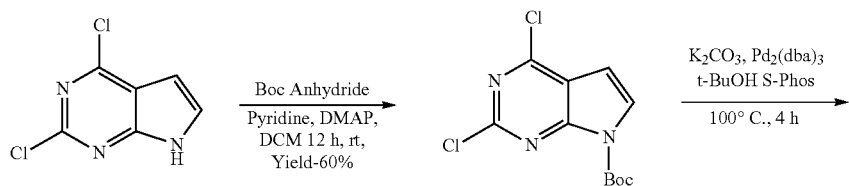

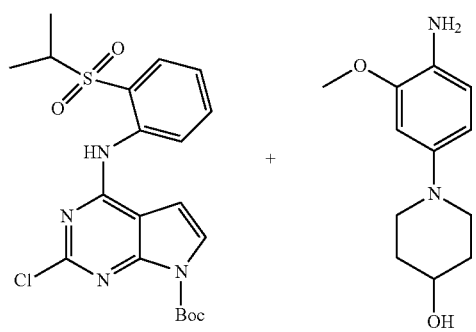

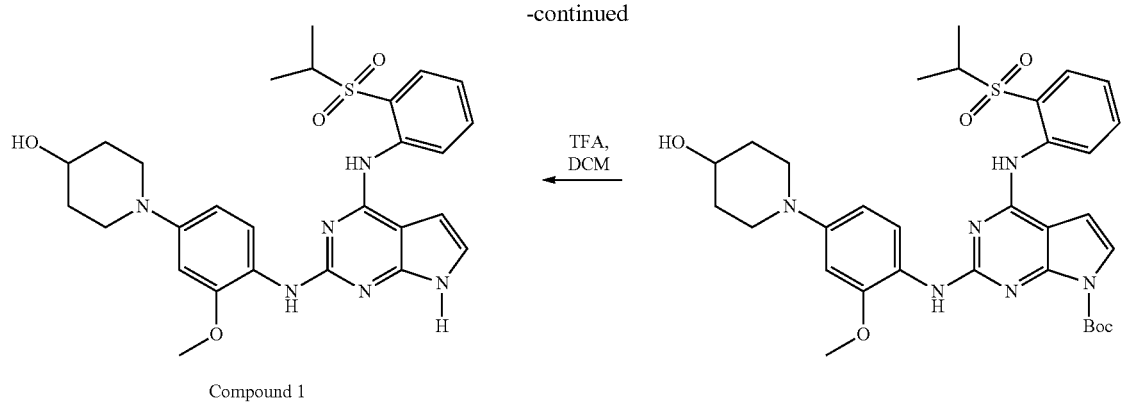

Compound 1

Alternatively, compounds 1, 10, 11, and 13 were synthesized as follows.

Preparation of Compound 1

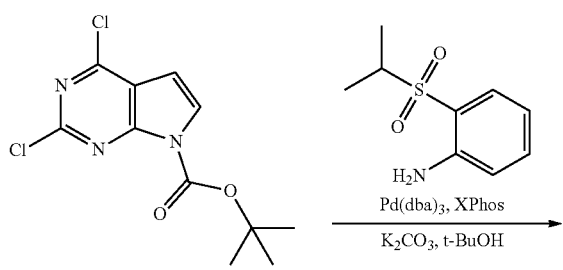

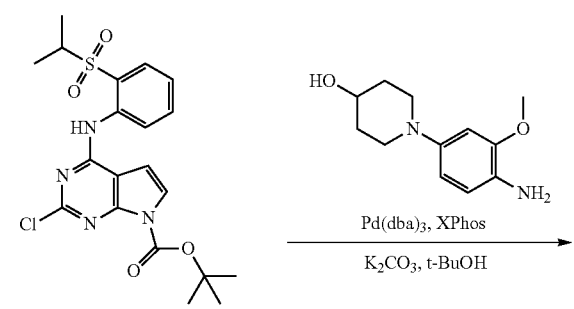

Step 1. Synthesis of tert-butyl 2-chloro-4-((2-(isopropylsulfonyl)phenyl)amino)-7H-pyrrolo[2,3-d]pyrimidine-7-carboxylate The synthesis of tert-butyl 2,4-dichloro-7H-pyrrolo[2,3-d]pyrimidine-7-carboxylate was achieved from 2,4-dichloro-7H-pyrrolo[2,3-d]pyrimidine according to Tumkevicius et al. (*Tet. Lett.*, 2010; 51:3902-3906). For the synthesis of the title compound, tert-butyl 2,4-dichloro-7H-pyrrolo[2,3-d]pyrimidine-7-carboxylate (0.239 g, 0.83 mmol), 2-(isopropylsulfonyl)-aniline (0.165 g, 0.83 mmol) and $K_2CO_3$ (0.220 g, 1.6 mmol) were dissolved in 3 mL t-butanol. The reaction mixture was degassed for 15 minutes. $Pd_2(dba)_3$ (0.046 g, 0.05 mmol) and XPhos (0.036 g, 0.076 mmol) were added to the reaction mixture under nitrogen atmosphere and stirred for 4 hours at 100° C. The reaction mixture was cooled to room temperature, filtered, partitioned between ethyl acetate and water. The aqueous layer was extracted three times with ethyl acetate. The combined organic layer was washed with water and brine, dried over sodium sulfate and concentrated under reduced pressure. The title compound was purified using silica gel column chromatography with 20-30% ethyl acetate hexane mixture as the solvent system (Yield 56%). $^1$H NMR (300 MHz, $CDCl_3$) δ 9.97 (s, 1H), 8.82 (d, J=8.5 Hz, 1H), 7.87 (d, J=7.7 Hz, 1H), 7.72 (t, J=7.3 Hz, 1H), 7.53 (d, J=4.0 Hz, 1H), 7.25 (t, J=7.7 Hz, 1H), 6.59 (d, J=3.9 Hz, 1H), 3.23 (m, 1H), 1.68 (s, 9H), 1.30 (d, J=6.8 Hz, 6H).

Step 2. Synthesis of tert-butyl 2-((4-(4-hydroxypiperidin-1-yl)-2-methoxyphenyl)amino)-4-((2-(isopropylsulfonyl)phenyl)amino)-7H-pyrrolo[2,3-d]pyrimidine-7-carboxylate tert-Butyl 2-chloro-4-((2-(isopropylsulfonyl)phenyl)amino)-7H-pyrrolo[2,3-d]pyrimidine-7-carboxylate (0.211 g, 0.47 mmol), 1-(4-amino-3-methoxyphenyl)piperidin-4-ol (0.125 g, 0.56 mmol) and K₂CO₃ (0.195 g, 1.41 mmol) were dissolved in 2 mL t-butanol. The reaction mixture was degassed for 15 minutes. Pd₂(dba)₃ (0.025 g, 0.028 mmol) and XPhos (0.020 g, 0.042 mmol) were added to the reaction mixture under nitrogen atmosphere and stirred for 6 hours at 100° C. The reaction mixture was cooled to room temperature, filtered, partitioned between ethyl acetate and water. The aqueous layer was extracted three times with ethyl acetate. The combined organic layer was washed with water and brine, dried over sodium sulfate and concentrated under reduced pressure. The title compound was purified using silica gel column chromatography with 80-90% ethyl acetate-hexane mixture as the solvent system (Yield 59%). ¹H NMR (300 MHz, CDCl₃) δ 8.37 (d, J=5.1 Hz, 1H), 7.99 (d, J=5.2 Hz, 1H), 7.89 (s, 1H), 7.55 (d, J=1.5 Hz, 1H), 7.38-7.25 (m, 1H), 7.24-7.03 (m, 1H), 6.84 (s, 1H), 6.59 (s, 1H), 6.53 (d, J=4.2 Hz, 1H), 6.30 (d, J=4.0 Hz, 1H), 4.24-4.05 (m, 1H), 3.87 (d, J=6.6 Hz, 3H), 3.50 (s, 2H), 3.29 (dd, J=10.1, 5.6 Hz, 1H), 2.91 (s, 2H), 2.06 (d, J=2.9 Hz, 2H), 1.78 (s, 2H), 1.69 (s, 9H), 1.29 (d, J=3.6 Hz, 6H).

Step 3. Synthesis of 1-(4-((4-((2-(isopropylsulfonyl)phenyl)amino)-7H-pyrrolo[2,3-d]pyrimidin-2-yl)amino)-3-methoxyphenyl)piperidin-4-ol (compound 1)

tert-Butyl 2-((4-(4-hydroxypiperidin-1-yl)-2-methoxyphenyl)amino)-4-((2-(isopropylsulfonyl)phenyl)amino)-7H-pyrrolo[2,3-d]pyrimidine-7-carboxylate (0.063 g, 0.10 mmol) was dissolved in 5 mL DCM. TFA (1 mL) was added to the reaction mixture and stirred for 4 hour at room temperature. The reaction was neutralized with saturated NaHCO₃ solution and extracted three times with ethyl acetate. The combined organic layer was washed with water and brine, dried over sodium sulfate and was concentrated under reduced pressure. Compound 1 was purified using preparative thin layer chromatography with ethyl acetate and few drops of methanol as the solvent system (Yield 35%). ¹H NMR (300 MHz, DMSO-d₆) δ 11.40 (s, 1H), 9.48 (s, 1H), 8.81 (d, J=8.4 Hz, 1H), 7.81 (m, 2H), 7.74-7.66 (m, 1H), 7.50 (s, 1H), 7.36-7.17 (m, 1H), 6.99 (s, 1H), 6.64 (s, 1H), 6.48 (d, J=9.9 Hz, 1H), 6.22 (s, 1H), 4.69 (d, J=3.2 Hz, 1H), 3.81 (s, 3H), 3.72-3.55 (m, 1H), 3.58-3.39 (m, 3H), 2.80 (t, J=11.2 Hz, 2H), 1.93-1.77 (m, 2H), 1.65-1.41 (m, 2H), 1.17 (d, J=6.2 Hz, 6H). HR-MS (M+Na)⁺ calculated 559.2103. observed 559.2132.

Preparation of Compound 10

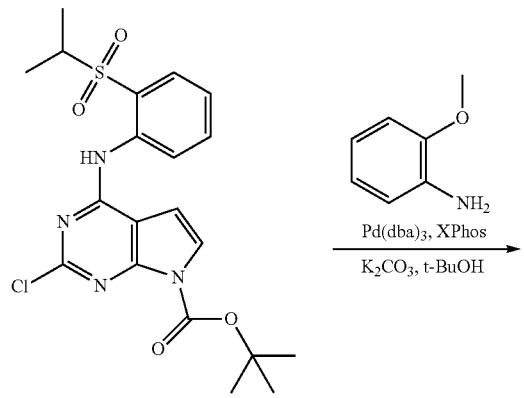

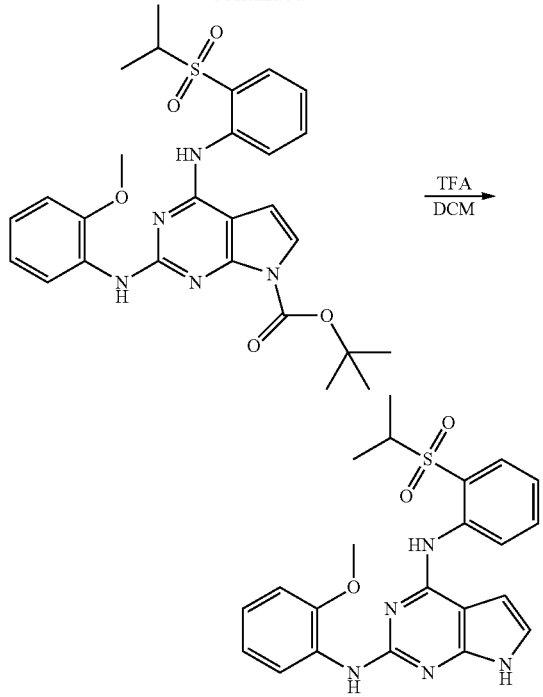

Step 1. Synthesis of tert-butyl 4-((2-(isopropylsulfonyl)phenyl)amino)-2-((2-methoxy-phenyl)amino)-7H-pyrrolo[2,3-d]pyrimidine-7-carboxylate tert-Butyl 2-chloro-4-((2-(isopropylsulfonyl)phenyl)amino)-7H-pyrrolo[2,3-d]pyrimidine-7-carboxylate (0.350 g, 0.78 mmol), 2-methoxyaniline (0.106 g, 0.86 mmol) and K₂CO₃ (0.317 g, 2.3 mmol) were dissolved in 4 mL t-butanol. The reaction mixture was degassed for 15 minutes. Pd₂(dba)₃ (0.045 g, 0.049 mmol) and XPhos (0.040 g, 0.084 mmol) were added to the reaction mixture under nitrogen atmosphere and stirred for 6 hours at 100° C. The reaction mixture was cooled to room temperature, filtered, partition between ethyl acetate and water. The aqueous layer was extracted three times with ethyl acetate. The combined organic layer was washed with water and brine, dried over sodium sulfate and concentrated under reduced pressure. The title compound was purified using silica gel column chromatography (Yield 49%). ¹H NMR (300 MHz, DMSO-d₆) δ 9.56 (s, 1H), 8.47 (d, J=8.8 Hz, 1H), 8.40 (d, J=7.2 Hz, 1H), 7.88 (d, J=8.6 Hz, 1H), 7.78 (m, 2H), 7.42 (m, 2H), 7.02 (d, J=7.8 Hz, 1H), 6.96 (t, J=6.5 Hz, 1H), 6.84 (t, J=8.1 Hz, 1H), 6.54 (d, J=3.8 Hz, 1H), 3.87 (s, 3H), 3.50-3.33 (m, 1H), 1.63 (s, 9H), 1.13 (d, J=6.8 Hz, 6H).

Step 2. Synthesis of N4-(2-(isopropylsulfonyl)phenyl)-N2-(2-methoxyphenyl)-7H-pyrrolo-[2,3-d]pyrimidine-2,4-diamine (compound 10)

tert-Butyl 4-((2-(isopropylsulfonyl)phenyl)amino)-2-((2-methoxy-phenyl)amino)-7H-pyrrolo[2,3-d]pyrimidine-7-carboxylate (0.100 g, 0.19 mmol) was dissolved in 5 mL DCM. TFA (1 mL) was added to the reaction mixture and stirred for 4 hour at room temperature. The reaction was neutralized with saturated NaHCO₃ solution and extracted three times with ethyl acetate. The combined organic layer was washed with water and brine, dried over sodium sulfate and concentrated under reduced pressure. Compound 10 was purified using silica gel column chromatography (Yield 48%). ¹H NMR (300 MHz, DMSO-d₆) δ 11.51 (s, 1H), 9.48 (s, 1H), 8.71 (d, J=8.5 Hz, 1H), 8.29 (d, J=6.6 Hz, 1H), 7.84 (d, J=7.9 Hz, 1H), 7.75 (t, J=6.7 Hz, 1H), 7.63 (s, 1H), 7.32 (t, J=6.8 Hz, 1H), 7.13-7.00 (m, 2H), 6.98-6.78 (m, 2H), 6.27 (s, 1H), 3.86 (s, 3H), 3.52-3.27 (m, 1H), 1.16 (d, J=6.9 Hz, 6H). HR-MS (M+Na)⁺ calculated 460.1419. observed 460.1312.

Preparation of Compound 11

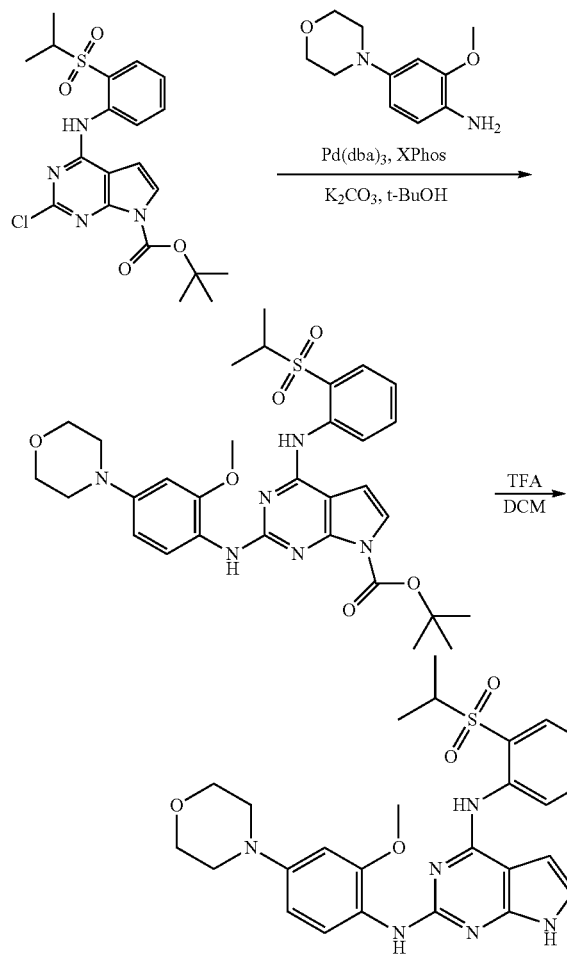

Step 1. Synthesis of tert-butyl 4-((2-(isopropylsulfonyl)phenyl)amino)-2-((2-methoxy-4-morpholinophenyl) amino)-7H-pyrrolo[2,3-d]pyrimidine-7-carboxylate tert-Butyl 2-chloro-4-((2-(isopropylsulfonyl)phenyl) amino)-7H-pyrrolo[2,3-d]pyrimidine-7-carboxylate (0.350 g, 0.78 mmol), 2-methoxy-4-morpholinoaniline (0.162 g, 0.78 mmol) and K₂CO₃ (0.317 g, 2.3 mmol), were dissolved in 4 mL t-butanol. The reaction mixture was degassed for 15 minutes. Pd₂(dba)₃ (0.045 g, 0.049 mmol) and XPhos (0.040 g, 0.084 mmol) were added to the reaction mixture under nitrogen atmosphere and stirred for 4 hours at 100° C. The reaction mixture was cooled to room temperature, filtered, partition between ethyl acetate and water. The aqueous layer was extracted three times with ethyl acetate. The combined organic layer was washed with water and brine, dried over sodium sulfate and concentrated under reduced pressure. The title compound was purified using silica gel column chromatography (Yield 42%). ¹H NMR (300 MHz, CDCl₃) δ 9.58 (s, 1H), 8.85 (d, J=8.4 Hz, 1H), 8.49 (d, J=9.1 Hz, 1H), 7.91 (d, J=7.4 Hz, 1H), 7.67 (t, J=8.0 Hz, 1H), 7.55 (s, 1H), 7.33 (d, J=4.0 Hz, 1H), 7.23 (t, J=7.8 Hz, 1H), 6.58 (d, J=10.2 Hz, 2H), 6.51 (d, J=4.0 Hz, 1H), 3.91 (m, 7H), 3.37-3.22 (m, 1H), 3.21-3.13 (m, 4H), 1.74 (s, 9H), 1.34 (d, J=6.8 Hz, 6H).

Step 2. Synthesis of N4-(2-(isopropylsulfonyl)phenyl)-N2-(2-methoxy-4-morpholinophenyl)-7H-pyrrolo[2,3-d]pyrimidine-2,4-diamine (compound 11)

tert-Butyl 4-((2-(isopropylsulfonyl)phenyl)amino)-2-((2-methoxy-4-morpholinophenyl) amino)-7H-pyrrolo[2,3-d] pyrimidine-7-carboxylate (0.100 g, 0.16 mmol) was dissolved in 5 mL DCM. TFA (1 mL) was added to the reaction mixture and stirred for 4 hour at room temperature. The reaction was neutralized with saturated NaHCO₃ solution and extracted three times with ethyl acetate. The combined organic layer was washed with water and brine, dried over sodium sulfate and concentrated under reduced pressure. Compound 11 was purified using silica gel column chromatography (Yield 36%). ¹H NMR (300 MHz, CDCl₃) δ 9.52 (s, 1H), 9.28 (s, 1H), 8.88 (d, J=8.2 Hz, 1H), 8.27 (d, J=8.6 Hz, 1H), 7.89 (dd, J=8.1, 1.3 Hz, 1H), 7.65 (t, J=7.2 Hz, 1H), 7.19 (dd, J=9.1, 5.8 Hz, 2H), 6.80-6.73 (m, 1H), 6.60 (d, J=2.4 Hz, 1H), 6.55 (dd, J=9.0, 1.7 Hz, 1H), 6.47-6.37 (m, 1H), 3.90 (m, 7H), 3.29 (dt, J=13.9, 6.9 Hz, 1H), 3.21-3.10 (m, 4H), 1.32 (d, J=6.9 Hz, 6H). HR-MS (M+Na)⁺ calculated 545.1947. observed 545.1882.

Preparation of Compound 13

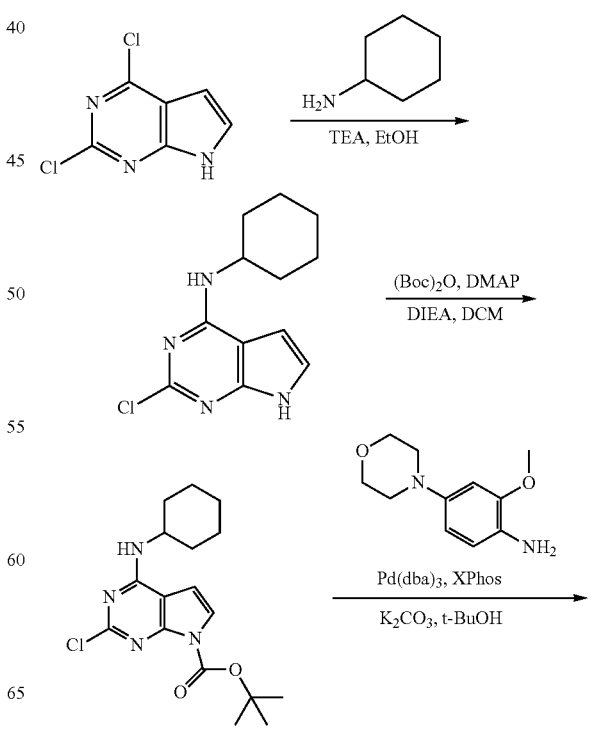

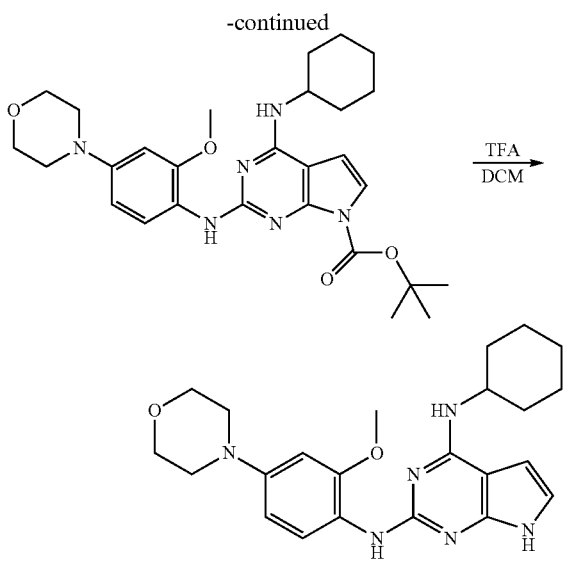

Step 1. Synthesis of 2-chloro-N-cyclohexyl-7H-pyrrolo[2,3-d]pyrimidin-4-amine 2,4-Dichloro-7H-pyrrolo[2,3-d]pyrimidine (0.695 g, 3.75 mmol), cyclohexylamine (0.406 g, 4.1 mmol) and TEA (0.758 g, 7.5 mmol) were dissolved in 18 mL ethanol and refluxed overnight. The solvent was reduced and the residue was dissolved in ethyl acetate. The organic layer was washed with water and brine, dried over sodium sulfate and concentrated under reduced pressure. The title compound was purified by silica gel column chromatography with 30-40% ethyl acetate-hexane mixture (Yield 78%). $^1$H NMR (300 MHz, DMSO-$d_6$) δ 11.60 (s, 1H), 7.60 (d, J=7.6 Hz, 1H), 7.40 (d, J=3.8 Hz, 1H), 6.60 (d, J=3.3 Hz, 1H), 3.95 (m, 1H), 1.94-1.90 (m, 2H), 1.77-1.74 (m, 2H), 1.65-1.61 (m, 1H), 1.42-1.20 (m, 4H), 1.18-1.13 (m, 1H).

Step 2. Synthesis of tert-butyl 2-chloro-4-(cyclohexylamino)-7H-pyrrolo[2,3-d]pyrimidine-7-carboxylate 2-Chloro-N-cyclohexyl-7H-pyrrolo[2,3-d]pyrimidin-4-amine (10, 0.400 g, 1.6 mmol) was dissolved in 6 mL of DCM. Di-tert-butyl dicarbonate (0.419 g, 1.92 mmol), DIEA (0.248 g, 1.92 mmol) and DMAP (0.010 g, 0.08 mmol) were added to the reaction mixture, and the mixture was refluxed for 10 minutes. The reaction mixture was cooled, diluted with water and the aqueous layer was extracted three times with DCM. The combined organic layer was washed with water and brine, dried over sodium sulfate and concentrated under reduced pressure. The title compound was purified using silica gel column chromatography with 5-10% ethyl acetate-hexane mixture as the solvent system (Yield 85%). $^1$H NMR (300 MHz, DMSO-$d_6$) δ 7.90 (d, J=7.6 Hz, 1H), 7.40 (d, J=3.8 Hz, 1H), 6.86 (d, J=3.3 Hz, 1H), 3.94 (s, 1H), 1.93 (s, 2H), 1.73 (s, 2H), 1.57 (s, 9H), 1.32 (m, 4H), 1.17 (m, 2H).

Step 3. Synthesis of tert-butyl 4-(cyclohexylamino)-2-((2-methoxy-4-morpholinophenyl)amino)-7H-pyrrolo[2,3-d]pyrimidine-7-carboxylate tert-Butyl 2-chloro-4-(cyclohexylamino)-7H-pyrrolo[2,3-d]pyrimidine-7-carboxylate (0.518 g, 1.48 mmol), 2-methoxy-4-morpholinoaniline (0.323 g, 1.55 mmol) and $K_2CO_3$ (0.290 g, 2.1 mmol) was dissolved in 4 mL t-butanol. The reaction mixture was degassed for 15 minutes. $Pd_2$(dba)$_3$ (0.068 g, 0.075 mmol) and XPhos (0.048 g, 0.102 mmol) were added to the reaction mixture under nitrogen atmosphere and stirred for 6 hours at 100° C. The reaction mixture was cooled to room temperature, filtered, partitioned between ethyl acetate and water. The aqueous layer was extracted three times with ethyl acetate. The combined organic layer was washed with water and brine, dried over sodium sulfate and concentrated under reduced pressure. The title compound was purified using silica gel column chromatography with 60-70% ethyl acetate-hexane mixture as the solvent system (Yield 45%). $^1$H NMR (300 MHz, DMSO-$d_6$) δ 8.48 (d, J=8.8 Hz, 1H), 7.27 (d, J=7.4 Hz, 1H), 7.17 (s, 1H), 7.14 (d, J=4.0 Hz, 1H), 6.71 (d, J=4.0 Hz, 1H), 6.66 (d, J=2.3 Hz, 1H), 6.43 (dd, J=8.9, 2.1 Hz, 1H), 3.98 (m, 1H), 3.89 (s, 3H), 3.81-3.70 (m, 4H), 3.15-3.01 (m, 4H), 1.96 (s, 1H), 1.78 (d, J=9.8 Hz, 2H), 1.73-1.67 (m, 1H), 1.60 (s, 9H), 1.44-1.21 (m, 6H).

Step 4. Synthesis of N4-cyclohexyl-N2-(2-methoxy-4-morpholinophenyl)-7H-pyrrolo[2,3-d]pyrimidine-2,4-diamine (compound 13)

tert-Butyl 4-(cyclohexylamino)-2-((2-methoxy-4-morpholinophenyl)amino)-7H-pyrrolo[2,3-d]pyrimidine-7-carboxylate (0.100 g, 0.19 mmol) was dissolved in 5 mL DCM. TFA (1 mL) was added to the reaction mixture and stirred for 4 hour at room temperature. The reaction was neutralized with saturated $NaHCO_3$ solution and extracted three times with ethyl acetate. The combined organic layer was washed with water and brine, dried over sodium sulfate and concentrated under reduced pressure. The product, Compound 13, was purified using silica gel column chromatography with 90% ethyl acetate-hexane as the solvent system (Yield 33%). $^1$H NMR (300 MHz, DMSO-$d_6$) δ 11.22 (s, 1H), 8.10 (s, 1H), 7.72 (s, 2H), 6.83 (s, 1H), 6.67 (d, J=2.1 Hz, 1H), 6.55 (s, 1H), 6.49 (dd, J=8.8, 2.1 Hz, 1H), 3.96 (d, J=5.6 Hz, 1H), 3.86 (s, 3H), 3.80-3.69 (m, 4H), 3.16-3.02 (m, 4H), 1.97 (1.80 d, J=10.2 Hz, 2H), 1.78 (d, J=10.2 Hz, 2H), 1.67 (m, 1H), 1.35-1.25 (m, 5H). HR-MS (M+Na)$^+$ calculated 445.2328; observed 445.2277.

3) Drug Validation:

In vitro evaluation of synthesized molecules include determination of anti-proliferative effects on BC cell lines, anchorage-independent cell transformation assays, kinase inhibition assays, and functional cell biology studies on centriole assembly and the spindle checkpoint.

The anti-proliferative effects and $IC_{50}$ values of the compounds in the BC cell line panel were determined by MTS assay.

The cells, except Sk-Br-3, AU565 and BT-474 were maintained in a mixture of Dulbecco's modified Eagle's medium and Ham's F12 medium (1:1) (DMEM/F12) without phenol red supplemented with 5% fetal bovine serum (FBS) and 1× antibiotic-antimycotic (100 U/mL penicillin G sodium, 100 μg/mL streptomycin sulfate and 0.25 μg/mL amphotericin B) and were plated separately in flasks in a humidified incubator (5% CO2: 95% air, 37° C.). The media used for Sk-Br-3, AU565 and BT-474 cell lines was described in (1) Brueggemeier et al., *J. Steroid Biochem. Mol. Biol.*, 2005; 95:129-136; and (2) Diaz-Cruz et al., *J. Clin. Endocrinol. Metab.*, 2005; 90:2563-2570. The media were changed every 2-days. When the cells grew to about 80% confluence, cells were washed twice with calcium- and magnesium-free phosphate-buffered saline (PBS, pH 7.4), and then trypsinized with 0.05% trypsin-5.3 mm EDTA. The trypsinization was stopped by addition of culture medium with 5% FBS. After centrifugation, the dissociated cells were resuspended in the same medium and subcultured into 75-cm² culture flasks at a ratio of 1:5 flasks.

Figure 2:
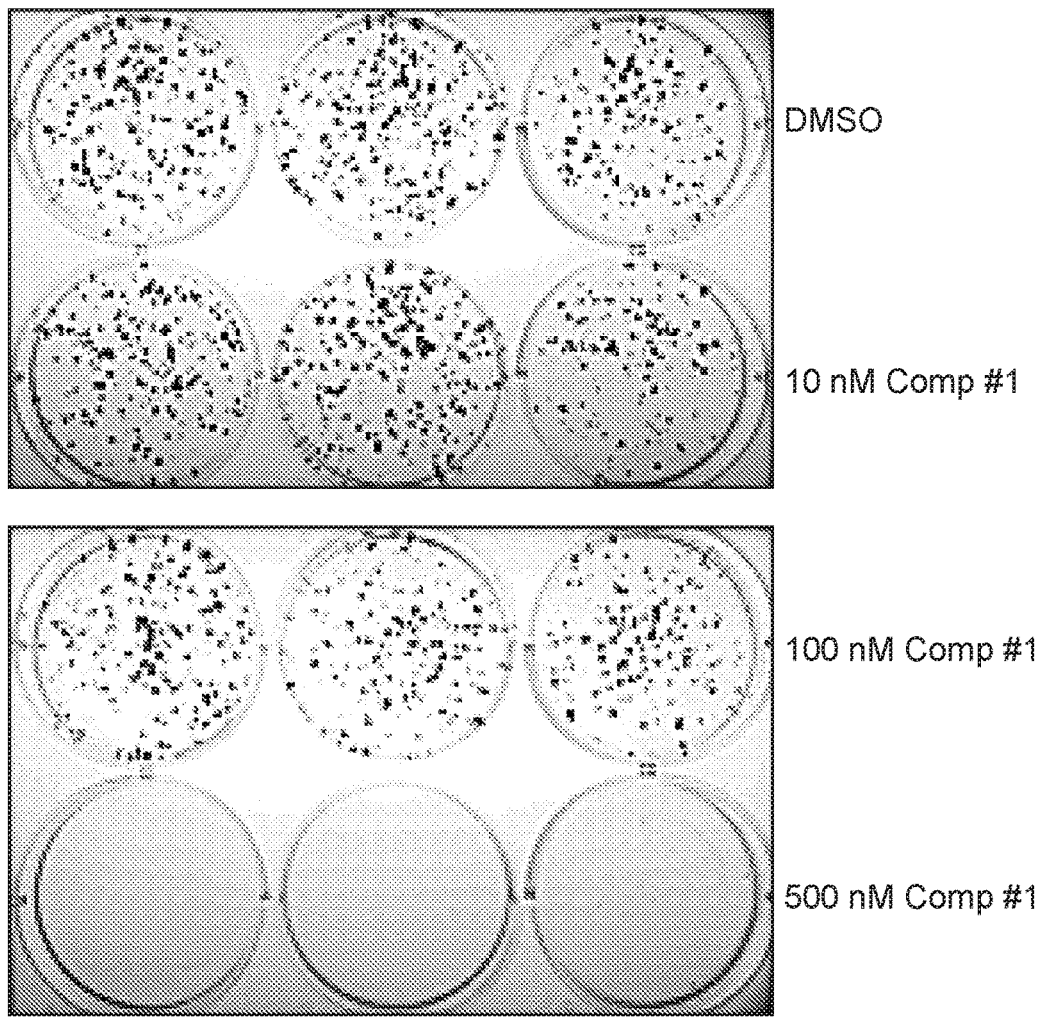
FIG. 2 shows the effects of compound 1 on colony formation.

The BC cells were seeded at the density of 1,000 cells per well (100 μL) into 96 well plate in DMEM/F-12 (1:1), supplemented with 5% (v/v) FCS and incubated overnight at 37° C. Test compounds are solubilized in dimethyl sulfoxide (DMSO), diluted in cell culture medium to a range of final assay concentrations of 1 nM to 10 μM, added to cells and incubated for 7 days at 37° C. The medium including the test compound are refreshed at days 3 and 5. The MTS assay are carried out by using the CellTiter 96® AQueous One Solution Cell Proliferation Assay kit following the manufacturer's instruction. In preliminary studies of the initial series, compounds 1 and 13 demonstrated an anti-proliferative effect with a moderate selectivity toward TNBC cells (Table 1).

reduction in colony formation was observed at 100 nM, and no breast cancer cell colonies were formed at the 500 nM concentration (see FIG. 2)

Mps1 Kinase Inhibition:

To determine the efficacy of the compounds against Mps1/TTK kinase activity, assays were performed as previously described (11) using recombinant Mps1, Cetn2 (specific substrate), and varying concentration of compound. This enzyme assay using Cetn2 exhibits greater sensitivity than using a generic substrate (e.g., MBP).

Briefly, the inhibition potency to Mps1 kinase activity was determined by measurement of radioactive phosphotransfer to the specific substrate, Cetn2. The autophosphorylation of Mps1 was also measured using the same method without adding Cetn2 in the kinase assay reaction mixture. The absolute Km values for ATP and the Cetn2 were initially determined and each reaction was carried out at optimum ATP and Cetn2 concentrations, 2×Km and 5×Km, respectively. Mps1 activity was measured using 0.25 ng of recom-

TABLE 1

IC$_{50}$ determinations of compounds 1, 10, 11, 13, and known inhibitor, Mps1-IN-1, in panel of breast cancer cell lines

| Cell line | BASAL subtype | IC$_{50}$ (μM) | | | | |
|---|---|---|---|---|---|---|
| | | Cpd 1 | Cpd 10 | Cpd 11 | Cpd 13 | Mps1-IN-1 |
| BT-549 | TNBC basal B | 0.81 | 1.60 | 1.31 | 0.06 | 2.44 |
| CAL-51 | TNBC basal | 0.23 | 1.50 | 0.30 | 0.45 | 1.84 |
| HCC1937 | TNBC basal | 0.73 | 0.99 | 1.10 | 1.09 | >10 |
| MDA-MB-436 | TNBC basal B | 0.90 | 1.29 | 1.23 | 0.66 | >10 |
| MDA-MB-468 | TNBC basal B | 0.19 | 1.86 | 0.36 | 0.57 | 1.85 |
| CAMA-1 | luminal | 0.36 | 1.55 | 0.78 | 1.10 | >10 |
| MDA-MB-453 | luminal A | 0.82 | >10 | >10 | 0.35 | >10 |
| BT-20 | TNBC basal A | 0.35 | 0.05 | 1.50 | 0.57 | >10 |
| Hs578T | TNBC basal B | >10 | >10 | >10 | >10 | >10 |
| MDA-MB-231 | TNBC basal B | >10 | 0.45 | >10 | >10 | >10 |
| MCF-7 | luminal A | 0.44 | 0.35 | 0.40 | >10 | >10 |
| Sk-Br-3 | luminal | >10 | 0.97 | 0.37 | 0.78 | >10 |
| AU565 | luminal | >10 | >10 | | 0.90 | >10 |
| T47D | luminal | >10 | 0.34 | | >10 | >10 |
| BT-474 | luminal B | >10 | 0.72 | 0.33 | 0.05 | >10 |

IC$_{50}$ values are averages of three independent assays and are determined by ten-point dosage treatment for 7 days.
n = 6;
blank spaces = in progress No notable cytotoxicity was observed after 24 hours of treatment at concentrations as high as 10 μM. Compounds 1 and 13 were also tested in the primary cultures of normal breast epithelial cells; both compounds exhibited no inhibition or incomplete dose-response curves up to 20 μM. Compounds 1, 10, 11 and 13 are significantly more potent as compared to the known Mps1/TTK inhibitor, Mps1-IN-1, in some or all of the cell based assays in the panel.

Clonogenic Assay:

A breast cancer cell line MDA-MB-468 was harvested at the exponential growing phase and counted the density of 2,000 cells per well (100 μL) into 6 well plate in phenol read free Dulbecco's Modified Eagles Medium (DMEM)/F-12 (1:1), (Sigma-Aldrich, Catalogue D2906) supplemented with 5% (v/v) FCS and incubated overnight at 37° C. Once the cells were attached cells were treated with the test compound at the concentration of 10 nM, 100 nM or 500 nM for 72 hours. DMSO was used as a vehicle control. Moderate binant GST-Mps1 protein in 50 mM TrisCl pH 7.5, 0.5 mM DTT, 10 mM MgCl$_2$, 300 μM recombinant Cetn2 and 3 μM $^{32}$P-γ-ATP. The assay was run in a 96 well plate; eleven serial 1:4 compound dilutions (from 0.025 nM to 25 μM) were tested to determine IC$_{50}$ values. ATP was added to initiate the kinase assay, incubated at 30° C. for 30 min and five-fold volume of 50 μM EDTA was added to quench the reaction. The whole reaction was immobilized on Immobilon-P$^{SQ}$ PVDF membrane (Millipore) using a dot blotter connected to vacuum line. Each well was washed three times with 300 μL of PBS. The membrane was further washed by soaking in PBS, dried, and exposed overnight to a Phosphor Screen. The image was acquired by the Storm imaging system (Amersham). The density analyses were performed by using Image-J program, and kinetic constants were calculated by GraphPad Prism 5 software. Commercial kinase profiling assays were performed by Reaction Biology Corp., Malvern, Pa.

In preliminary investigations, compound 1 inhibited in vitro kinase activity of Mps1 with an IC$_{50}$ value of 155 nM and compound 13 with an $IC_{50}$ value of 30 nM. On the other hand, Mps1-IN-1 exhibited an $IC_{50}$ value of 7 µM in the assay system.

In additional investigations (see Table 2), compound 1 inhibited in vitro kinase activity of Mps1 with an $IC_{50}$ value of 809 nM and compound 13 with an $IC_{50}$ value of 356 nM. Compound 10 and compound 11 were less effective, with $IC_{50}$ values of 3.4 and 13.1 µM, respectively. On the other hand, Mps1-IN-1 exhibited an $IC_{50}$ value of 1.7 µM in the assay system. Compound 13 was further evaluated in kinase profiling assays for twenty common kinases and exhibited inhibition of only two kinases, FAK/PTK2 and JNK1, with $IC_{50}$ values at 0.89 µM and 1.67 µM, respectively. Thus, compound 13 demonstrated selectivity for Mps1/TTK kinase.

TABLE 2

$IC_{50}$ determination of inhibitors (in vitro kinase assay)

|  | w/Cetn 2 (µM) | w/o Cetn 2 (µM) |
| --- | --- | --- |
| Compound 1 | 0.809 |  |
| Compound 10 | 3.422 |  |
| Compound 11 | 13.142 |  |
| Compound 13 | 0.356 | 0.312 |
| Mps1-IN-1 | 1.745 |  |
| AZ3146 | 0.015 | 0.072 |

$IC_{50}$ are determined by triplicate manner and are by 12 points dosage

To determine the functional cellular activity of the Mps1/TTK inhibitors, the reported centriole assembly (11), centrosome re-duplication (13-15), and spindle checkpoint assays (31) are performed.

For these cell biology assays, cells were plated onto poly-L-lysine coated coverslips in 24 well dishes using the medium and growth conditions described above, but using medium containing phenol red. At 24 hours after plating, compounds (or the equivalent amount of DMSO) were added to individual wells at various concentrations. Cells were incubated for 24 hours at 37° C. BrdU was added during the last 4 hours of the incubation, after which cells were fixed in pre-chilled methanol at -20 OC for 10 minutes, stained with centrosome markers, then treated with acid to denature chromosomal DNA prior to staining for BrdU. To assess centriole biogenesis, centriole number was determined for triplicate samples in cells that had entered S-phase as judged by incorporation of BrdU. Primary antibodies used were mouse anti-γTubulin (pericentriolar material) and rabbit anti-Centrin 2 (centrioles). Secondary antibodies used were Alexa594-conjugated donkey anti-mouse and Alexa488-conjugated donkey anti-rabbit.

For centriole assembly assays, Cal-51 and MDA-MB-468 cells were treated with candidate compounds prior to a short pulse of BrdU. Because the centriole pair is replicated at the G1/S transition, compounds that block centrosome assembly will lead to an increased number of BrdU-positive cells with two centrioles. In addition, like many breast cancer cells Cal-51 and MDA-MB-468 are capable of centrosome amplification, and compounds that block this centrosome amplification should reduce the number of BrdU-positive cells with more than four centrioles.

Figure 3:
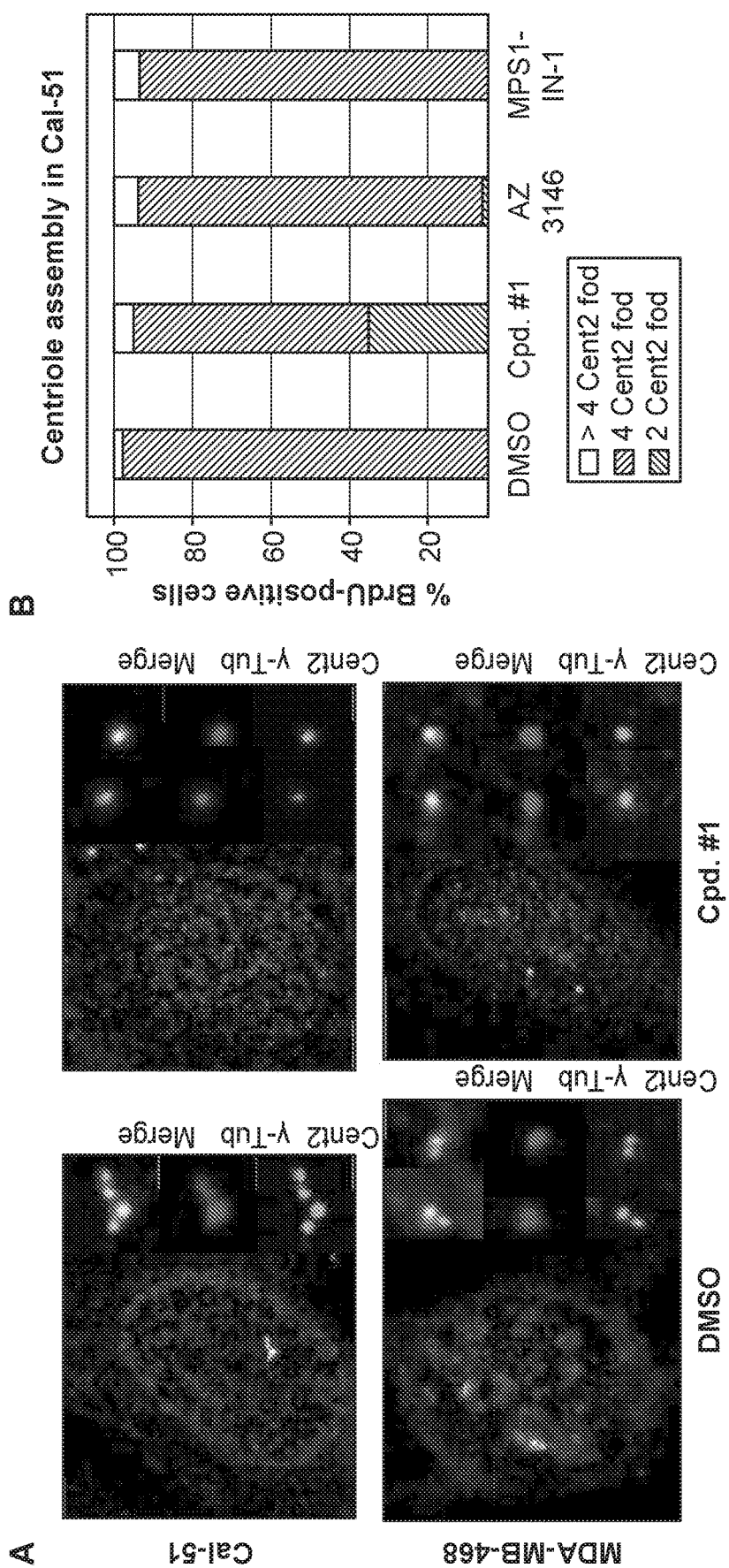
FIGS. 3A-3B show the effects of compound 1, AZ3146, or Mps1-IN-1 on centriole number in S-phase cells.

In preliminary investigations, the effects of compound 1, AZ3146, or Mps1-IN-1 on centriole number in S-phase cells were examined. Cells were treated with drug for 20 hours followed by a 4 hour pulse of BrdU. Roughly 94% of BrdU-positive DMSO-treated cells had completed centriole assembly (which normally occurs rapidly upon S-phase entry) and had four centrioles, but compound 1 led to a 5- to 10-fold increase in the percentage of BrdU positive cells that failed to assemble new centrioles and had just two centrioles despite having entered S-phase, while AZ3146 and Mps1-IN-1 had little effect on centriole assembly. As shown in FIG. 3A, centriole number was determined in at least 100 BrdU-positive cells per sample by counting the number of centrin2 foci associated with γ-Tubulin after staining with antibodies against BrdU (left), centrin2 (Cetn2, right, bottom), and γ-tubulin (γ-Tub, right, middle).

Figure 4:
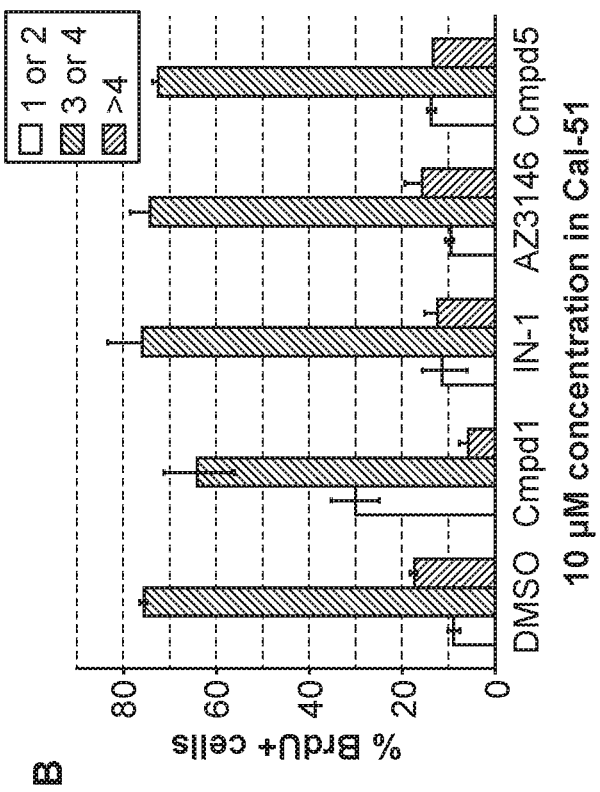
FIGS. 4A-4D show the effects of compound 1, AZ3146, or Mps1-IN-1 on centriole number in S-phase cells. Centriole number was determined in at least 100 BrdU-positive cells per sample for triplicate samples by counting the number of Cetn2 foci associated with γ-Tubulin after staining with antibodies against BrdU, Cetn2, and γ-Tubulin.
Figure 4:
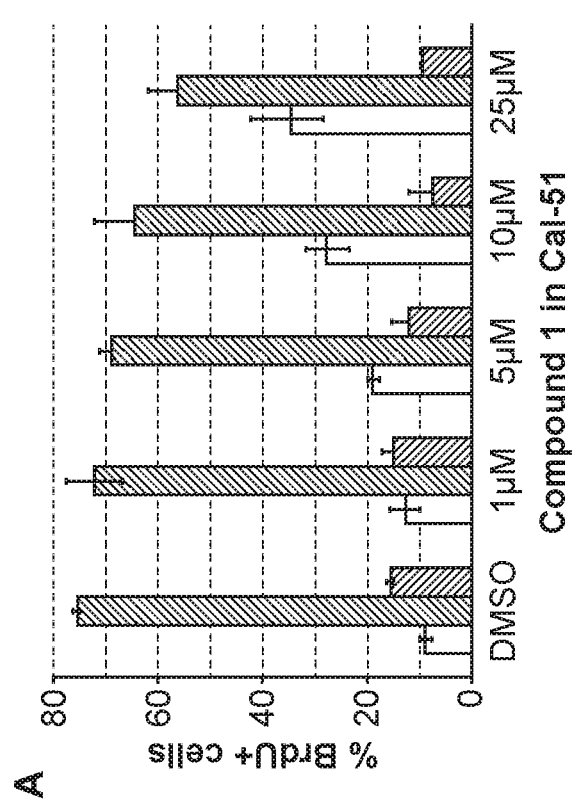
Figure 4:
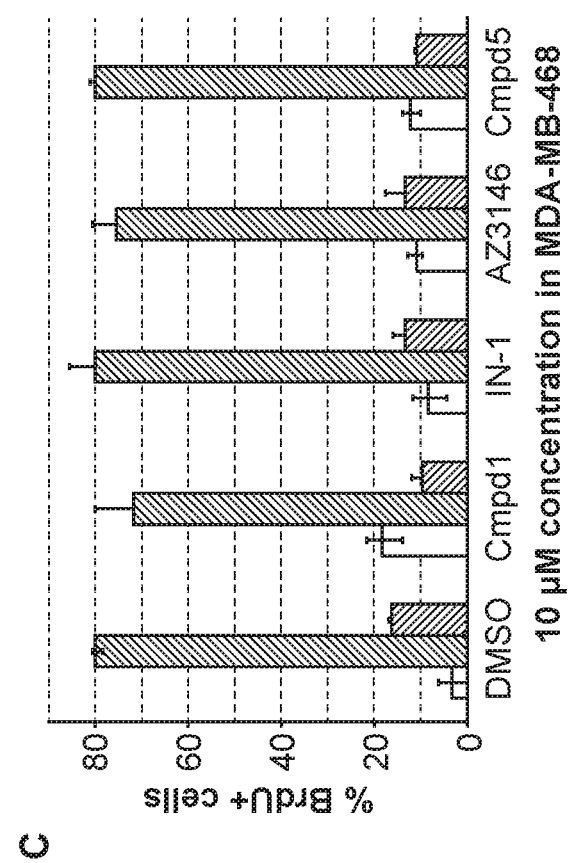

In continued investigations, treatment with compound 1 led to a dose-dependent increase in the percentage of BrdU positive cells that have failed to complete centriole assembly and have just two centrioles (see FIG. 4). Compound 1 also blocked centrosome amplification in Cal-51 cells, as evidenced by a dose-dependent reduction in the percentage of cells with more than four centrioles. In contrast, at 10 µM AZ3146 and Mps1-IN-1 have little effect on either centriole assembly or centrosome amplification. Compound 1 has a similar effect in MDA-MB-468 cells where it increases the percentage of BrdU-positive cells that have just two centrioles, and decreases the percentage with more than four centrioles, compared to IN-1, AZ3146, and Compound 5 that was included as a negative control that did not inhibit Mps1 kinase activity in vitro.

For centrosome re-duplication assays, cell lines [HeLa, 293(13), RPE-1, and MCF10A (unpublished)] engineered to inducibly express either wild type Mps1/TTK or Mps1Δ12/13 (which cannot be degraded at centrosomes) were treated with candidate compounds prior to a short pulse of BrdU. Compounds that prevent Mps1/TTK-driven centrosome amplification will attenuate the Mps1Δ12/13-dependent increase in BrdU-positive cells that have more than four centrioles. Compounds that prevent Mps1/TTK-driven centrosome amplification will also attenuate the increase in BrdU-positive cells that have more than four centrioles caused by inducible overexpression of wild type Mps1/TTK in MCF10A-derived lines. Alternatively, cells can be treated with candidate compounds prior to a prolonged S-phase arrest in a classical centrosome re-duplication assay. Compounds that prevent Mps1/TTK-driven centrosome amplification will attenuate the Mps1Δ12/13-dependent (and in MCF10A-derived lines the wild type Mps1/TTK-dependent) increase in S-phase arrested cells with more than four centrioles.

Figure 5:
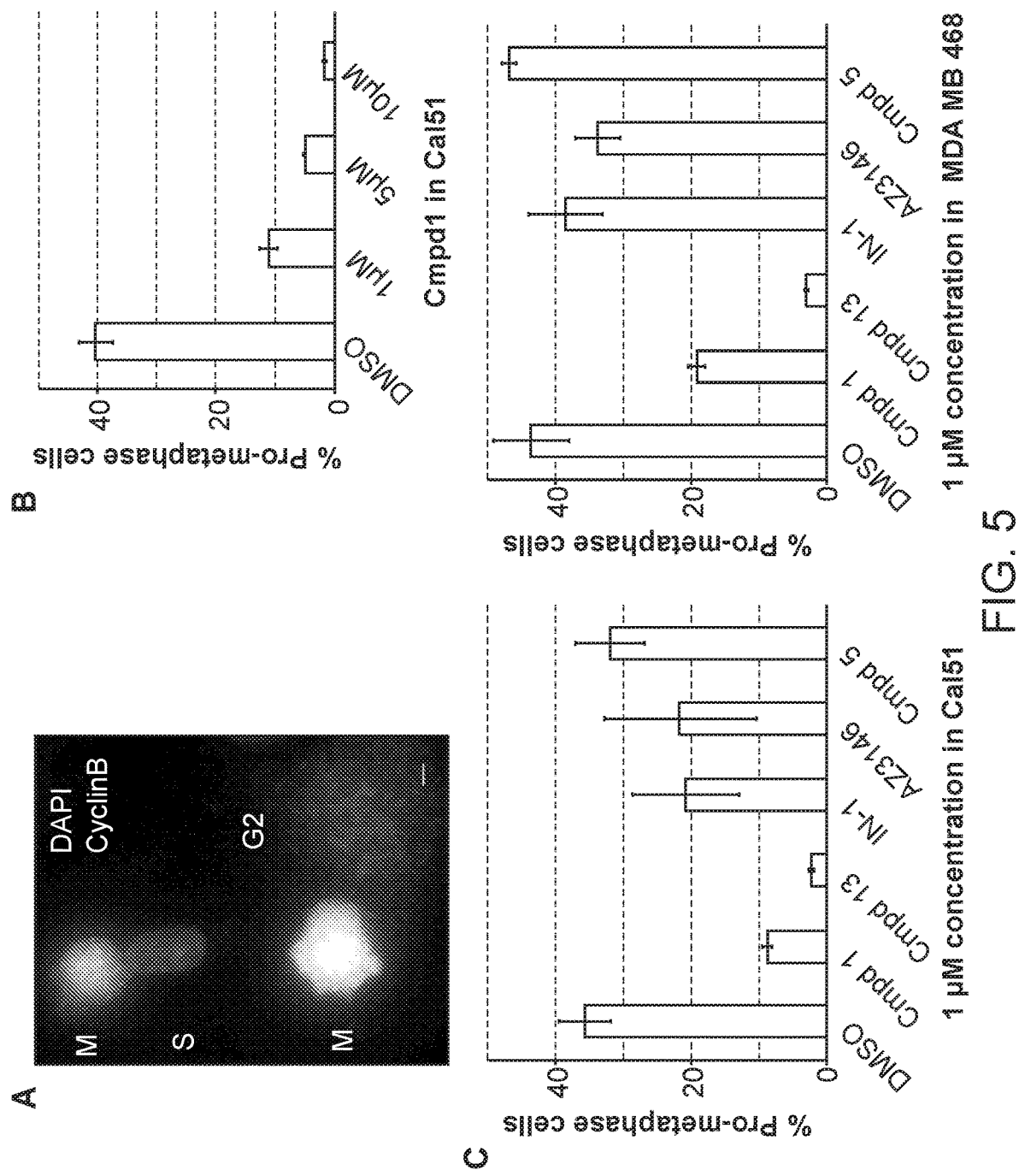
FIGS. 5A-5C show the effects of compound 1 and compound 13 on spindle checkpoint function. The percentage of prometaphase cells was determined in at least 100 cells per sample from triplicate samples by counting cyclin B-positive cells with condensed DNA in nocodazole treated samples.

For spindle checkpoint assays, S-phase arrested cells treated with candidate compounds were released into medium containing the spindle poison nocodazole. Because the spindle checkpoint prevents the metaphase to anaphase transition in the presence of spindle damage, compounds that block the spindle checkpoint will lead to a decreased number of mitotic cells in the presence of nocodazole. Briefly, cells were arrested in S-phase with a 24 hour treatment with 2 mM thymidine. Three hours after removing thymidine to release cells from S-phase arrest, nocodazole was added at 200 ng/mL. After 12 hours in the presence of nocodazole, cells were fixed and stained with mouse anti-cyclin B and Hoechst, and the percentage of cyclin B positive cells with condensed chromosomes was determined in triplicate samples. Roughly 40% of Cal-51 cells were arrested in metaphase after being released from S-phase arrest into nocodazole, but compound 1 led to a dose-dependent reduction in the ability of cells to arrest in response to nocodazole (see FIG. 5). At 1 µM, compound 13 was the most effective at abrogating the spindle checkpoint, and both compounds 1 and 13 were more effective than IN-1, AZ3146, or compound 5 that was included as a negative control. Compounds 1 and 13 had similar effects in MDA-MB-468 cells.

Alternatively, cells are treated with candidate compounds prior to arrest with monastrol (an inhibitor of the Eg5 kinesin). Compounds that block the spindle checkpoint will generate cells with misaligned chromosomes that prematurely enter anaphase upon release from monastrol arrest.

Figure 6:
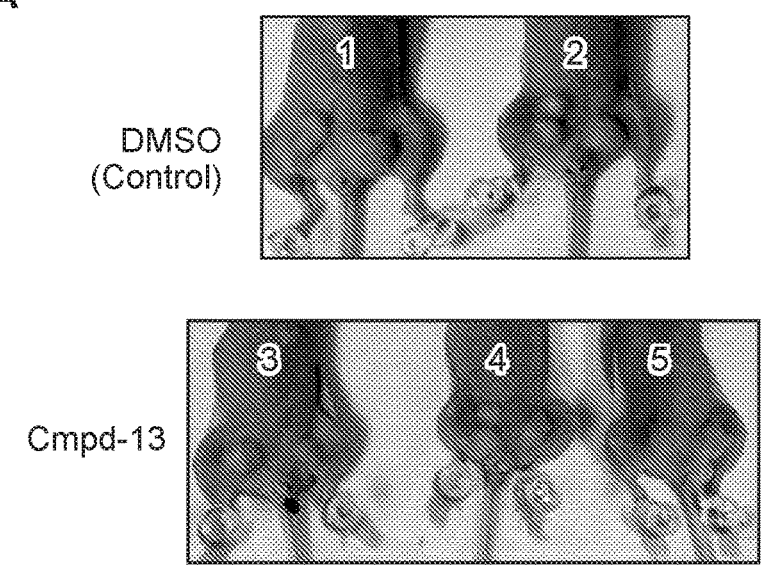
FIGS. 6A-6C shows an investigation of compound 13 on tumor progression in athymic nude mice.
Figure 6:
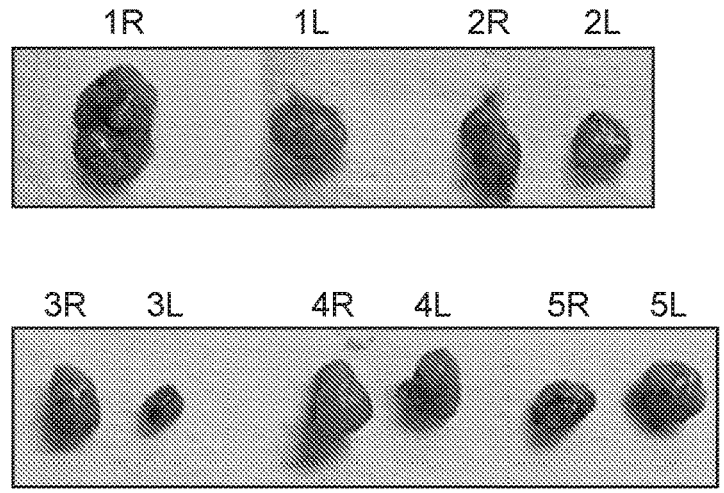
Figure 7:
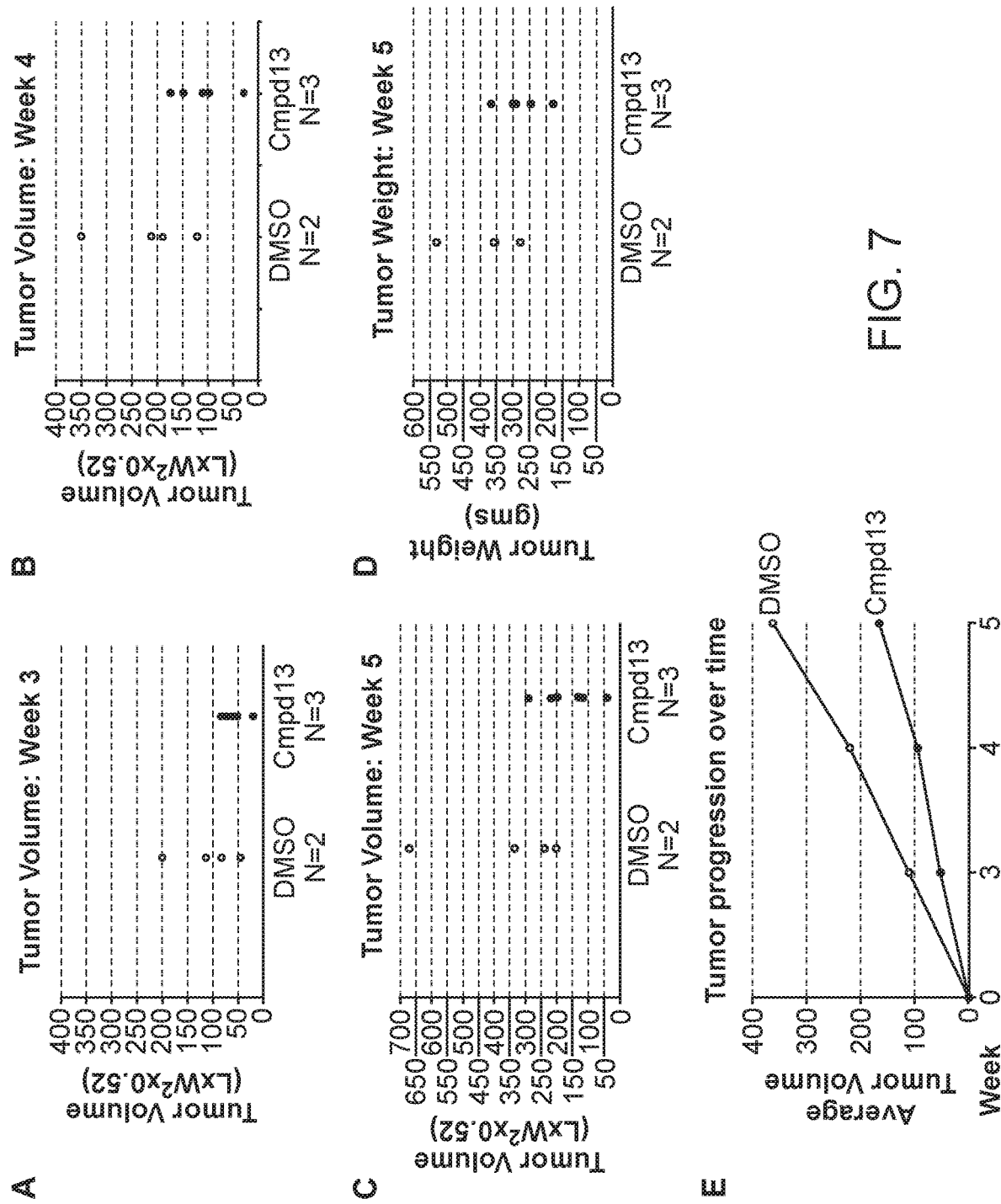
FIGS. 7A-7E shows an investigation of compound 13 on tumor progression in athymic nude mice.

The effect of compound 13 on tumor progression was investigated using athymic nude mice (total mice=5: 2 control, 3 test). Compound 13 in DMSO was administered to the test mice by i.p. injection. Cal-51 cells were injected to induce tumor growth. At the end of the five-week study, the mice were sacrificed, and the tumors were measured, dissected and weighed (FIGS. 6 and 7). The data suggested that compound 13 slowed the tumor progression in athymic nude mice.

Example 2

This example describes a human clinical trial of compound 1 in triple negative breast cancer. This phase 2 study determines the pathologic complete response rate (pCR). Time frame: biopsy at baseline and tissue removed at time of surgery (after approximately 12 weeks of therapy). Compound 1 is administered orally or intravenously to the patient. Treatment is administered over the course of each 21-day cycle for four cycles.

Patient Eligibility:
Inclusion Criteria:
Patients must have histologically confirmed breast cancer; diagnosis must be reviewed and confirmed prior to registration on study, and all biopsy materials need to be reviewed and available for correlative studies.

Patients must have stage I-III breast cancer.

Patients must have estrogen receptor-negative (ER−), progesterone receptor-negative (PR−), human epidermal growth factor receptor 2-negative (Her2−) (0, 1+) or fluorescent in situ hybridization (FISH)<ratio of 1.8.

Patients must have measurable disease, defined as at least one lesion that can be accurately measured in at least one dimension (longest diameter to be recorded) by mammogram, ultrasound or physical exam.

Prior diagnosis of cancer is allowed as long as patient is free of disease and has been off treatment for the prior malignancy for a minimal interval of one year.

Patients must have a life expectancy of >12 weeks.

Patients must exhibit an Eastern Cooperative Oncology Group (ECOG) performance status=<1 (Karnofsky >=80%).

Leukocytes >=3,000/µl.

Absolute neutrophil count >=1,500/µl.

Platelets >=100,000/µl.

Total bilirubin within normal institutional limits.

Aspartate aminotransferase (AST) (serum glutamic oxaloacetic transaminase [SGOT])/alanine transaminase (ALT) (serum glutamic pyruvic transaminase [SGPT]) =<2.5× institutional upper limit of normal.

Creatinine: within normal institutional limits.

OR creatinine clearance >=60 mL/min/1.73^2 for patients with creatinine levels above institutional normal.

Women of childbearing potential must commit to the use of effective contraception while on study.

Eligibility of patients receiving medications of substances known to affect, or with the potential to affect, the activity or pharmacokinetics of eribulin will be determined following review of their use by the Principal Investigator.

All patients must have given signed, informed consent prior to registration on study.

Exclusion Criteria

Prior chemotherapy, immunotherapy or hormonal therapy for breast cancer is NOT allowed.

Concomitant radiotherapy is NOT allowed.

Patients may NOT be receiving any other investigational agents or concurrent anticancer therapies; in addition, use of any herbal (alternative) medicines is NOT permitted.

Patients with uncontrolled inter-current illness including, but not limited to, ongoing or active infection, symptomatic congestive heart failure, unstable angina pectoris, cardiac arrhythmia, or psychiatric illness/social situations what would limit compliance with study requirements are NOT eligible to participate.

Women who are pregnant or lactating are NOT eligible to participate.

Example 3

This example describes a human clinical trial of compound 10 in triple negative breast cancer and is performed analogously to Example 2, replacing compound 1 for compound 10.

Example 4

This example describes a human clinical trial of compound 11 in triple negative breast cancer and is performed analogously to Example 2, replacing compound 1 for compound 11.

Example 5

This example describes a human clinical trial of compound 13 in triple negative breast cancer and is performed analogously to Example 2, replacing compound 1 for compound 13.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention such as for example, embodiments described in Appendix A attached hereto. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Sorlie T, Perou C M, Tibshirani R, Aas T, Geisler S, et al. 2001. Gene expression patterns of breast carcinomas distinguish tumor subclasses with clinical implications. *Proceedings of the National Academy of Sciences of the United States of America* 98:10869-74
2. Khalifeh I M, Albarracin C, Diaz L K, Symmans F W, Edgerton M E, et al. 2008. Clinical, histopathologic, and immunohistochemical features of microglandular adenosis and transition into in situ and invasive carcinoma. *American Journal of Surgical Pathology* 32:544-52
3. Blows F M, Driver K E, Schmidt M K, Broeks A, van Leeuwen F E, et al. 2010. Subtyping of Breast Cancer by Immunohistochemistry to Investigate a Relationship between Subtype and Short and Long Term Survival: A Collaborative Analysis of Data for 10,159 Cases from 12 Studies. *Plos Medicine* 7
4. Brough R, Frankum J R, Sims D, Mackay A, Mendes-Pereira A M, et al. 2011. Functional Viability Profiles of Breast Cancer. *Cancer Discovery* 1:260-73
5. Daniel J, Coulter J, Woo J H, Wilsbach K, Gabrielson E. 2011. High levels of the Mps1 checkpoint protein are protective of aneuploidy in breast cancer cells. *Proceedings of the National Academy of Sciences of the United States of America* 108:5384-9
6. Maire V, Baldeyron C, Richardson M, Tesson B, Vincent-Salomon A, et al. 2013. TTK/hMPS1 is an attractive therapeutic target for triple-negative breast cancer. *PloS one* 8:e63712
7. Winey M, Goetsch L, Baum P, Byers B. 1991. MPS1 and MPS2: Novel yeast genes defining distinct steps of spindle pole body duplication. *J. of Cell Biol.* 114:745-54
8. Lindberg R A, Fischer W H, Hunter T. 1993. Characterization of a human protein threonine kinase isolated by screening an expression library with antibodies to phosphotyrosine. *Oncogene* 8:351-9
9. Mills G B, Schmandt R, McGill M, Amendola A, Hill M, et al. 1992. Expression of TTK, a novel human protein kinase, is associated with cell proliferation. *J. Biol. Chem.* 267:16000-6
10. Fisk H A, Mattison C P, Winey M. 2003. Human Mps1 protein kinase is required for centrosome duplication and normal mitotic progression. *Proceedings of the National Academy of Sciences of the United States of America* 100:14875-80
11. Yang C H, Kasbek C, Majumder S, Mohd Yusof A, Fisk H A. 2010. Mps1 phosphorylation sites regulate the function of Centrin 2 in centriole assembly. *Molecular Biology of the Cell* 21:4361-72
12. Liu J, Cheng X, Zhang Y, Li S, Cui H, et al. 2013. Phosphorylation of Mps1 by BRAFV600E prevents Mps1 degradation and contributes to chromosome instability in melanoma. *Oncogene* 32:713-23
13. Kasbek C, Yang, C.-H., and Fisk, H. A. 2009. Mps1 as a link between centrosomes and genetic instability. *Environmental and Molecular Mutagenesis* 50:654-65
14. Kasbek C, Yang C H, Fisk H A. 2010. Antizyme Restrains Centrosome Amplification by Regulating the Accumulation of Mps1 at Centrosomes. *Molecular Biology of the Cell* 21:3879-89
15. Kasbek C, Yang C H, Yusof A M, Chapman H M, Winey M, Fisk H A. 2007. Preventing the degradation of mps1 at centrosomes is sufficient to cause centrosome reduplication in human cells. *Mol Biol Cell* 18:4457-69
16. Wei J H, Chou Y F, Ou Y H, Yeh Y H, Tyan S W, et al. 2005. TTK/hMps1 participates in the regulation of DNA damage checkpoint response by phosphorylating CHK2 on threonine 68. *Journal of Biological Chemistry* 280:7748-57
17. Mills G B, Schmandt R, Mcgill M, Amendola A, Hill M, et al. 1992. Expression of Ttk, a Novel Human Protein-Kinase, Is Associated with Cell-Proliferation. *Journal of Biological Chemistry* 267:16000-6
18. Schmandt R, Hill M, Amendola A, Mills G B, Hogg D. 1994. Il-2-Induced Expression of Ttk, a Serine, Threonine, Tyrosine Kinase, Correlates with Cell-Cycle Progression. *Journal of Immunology* 152:96-105
19. Saal L H, Gruvberger-Saal S K, Persson C, Loevgren K, Jumppanen M, et al. 2008. Recurrent gross mutations of the PTEN tumor suppressor gene in breast cancers with deficient DSB repair. *Nature Genetics* 40:102-7
20. Lingle W L, Barrett S L, Negron V C, D'Assoro A B, Boeneman K, et al. 2002. Centrosome amplification drives chromosomal instability in breast tumor development. *Proceedings of the National Academy of Sciences of the United States of America* 99:1978-83
21. Lingle W L, Salisbury J L. 1999. Altered centrosome structure is associated with abnormal mitoses in human breast tumors. *Am J Pathol* 155:1941-51.
22. Lingle W L, Lutz W H, Ingle J N, Maihle N J, Salisbury J L. 1998. Centrosome hypertrophy in human breast tumors: implications for genomic stability and cell polarity. *Proceedings of the National Academy of Sciences of the United States of America* 95:2950-5
23. Hewitt L, Tighe A, Santaguida S, White A M, Jones C D, et al. 2010. Sustained Mps1 activity is required in mitosis to recruit O-Mad2 to the Mad1-C-Mad2 core complex. *Journal of Cell Biology* 190:25-34
24. Kwiatkowski N, Jelluma N, Filippakopoulos P, Soundararaj an M, Manak M S, et al. 2010. Small-molecule kinase inhibitors provide insight into Mps1 cell cycle function. *Nature Chemical Biology* 6:359-68
25. Santaguida S, Tighe A, D'Alise A M, Taylor S S, Musacchio A. 2010. Dissecting the role of MPS1 in chromosome biorientation and the spindle checkpoint through the small molecule inhibitor reversine. *Journal of Cell Biology* 190:73-87
26. Tardif K D, Rogers A, Cassiano J, Roth B L, Cimbora D M, et al. 2011. Characterization of the Cellular and Antitumor Effects of MPI-0479605, a Small-Molecule Inhibitor of the Mitotic Kinase Mps1. *Molecular Cancer Therapeutics* 10:2267-75
27. Tannous B A, Kerami M, Van der Stoop P M, Kwiatkowski N, Wang J, et al. 2013. Effects of the selective MPS1 inhibitor MPS1-IN-3 on glioblastoma sensitivity to antimitotic drugs. *Journal of the National Cancer Institute* 105:1322-31
28. Li H, Liu A, Zhao Z, Xu Y, Lin J, et al. 2011. Fragment-based drug design and drug repositioning using multiple ligand simultaneous docking (MLSD): identifying celecoxib and template compounds as novel inhibitors of signal transducer and activator of transcription 3 (STAT3). *Journal of medicinal chemistry* 54:5592-6
29. Li H, Li C. 2010. Multiple ligand simultaneous docking: orchestrated dancing of ligands in binding sites of protein. *Journal of computational chemistry* 31:2014-22
30. CHEN B, JIANG T, MARSILJE T, H., MICHELLYS P-y, NGUYEN T, Ngoc, et al. 2009. COMPOUNDS AND COMPOSITIONS AS PROTEIN KINASE INHIBITORS. In US Patent WO2009/126515A1
31. Liu C, van Dyk D, Choe V, Yan J, Majumder S, et al. 2011. Ubiquitin ligase Ufd2 is required for efficient degradation of Mps1 kinase. *J Biol Chem* 286:43660-7
32. Chou T C, Talalay P. 1984. Quantitative analysis of dose-effect relationships: the combined effects of multiple drugs or enzyme inhibitors. *Advances in enzyme regulation* 22:27-55
33. Greco W R, Bravo G, Parsons J C. 1995. The search for synergy: a critical review from a response surface perspective. *Pharmacological reviews* 47:331-85
34. Rozewski D M, Herman S E, Towns W H, 2nd, Mahoney E, Stefanovski M R, et al. 2012. Pharmacokinetics and tissue disposition of lenalidomide in mice. *The AAPS journal* 14:872-82

The invention claimed is:

1. A compound of Formula IV-A or V-A:

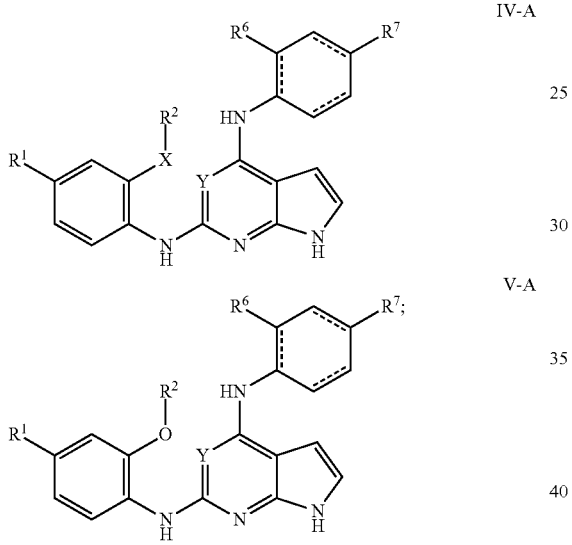

or a tautomer, a pharmaceutically acceptable salt and/or a solvate thereof;
wherein
X is O, S or $SO_2$;
Y is N;
$R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —C(O)O—$R^{10}$, —$NR^{10}R^{11}$, —C(O)$NR^{10}R^{11}$, —C(S)$NR^{10}R^{11}$, —$NR^{13}C(O)NR^{10}R^{11}$, —$NR^{13}C(S)NR^{10}R^{11}$, —O—C(O)$NR^{10}R^{11}$, —$S(O)_2NR^{10}R^{11}$, —O—$S(O)_2NR^{10}R^{11}$, —$NR^{13}$—$S(O)_2NR^{10}R^{11}$, CN, halo, $NO_2$, and —$S(O)_2$—$R^{12}$;
$R^2$ is selected from the group consisting of hydrogen, $C_1$-$C_3$ alkyl and $C_1$-$C_3$ haloalkyl; provided that when X is $SO_2$, or when $R^1$ is hydrogen, then $R^2$ is not hydrogen;
$R^6$ is selected from the group consisting of hydrogen, halo, —O—$R^{20}$, —C(O)—$R^{20}$, —C(O)O—$R^{20}$, —$NR^{20}R^{21}$, —C(S)$NR^{20}R^{21}$, —$NR^{23}C(O)NR^{20}R^{21}$, —$NR^{23}C(S)NR^{20}R^{21}$, —O—C(O)$NR^{20}R^{21}$, —$S(O)_2NR^{20}R^{21}$, —O—$S(O)_2NR^{20}R^{21}$, —$NR^{23}$—$S(O)_2NR^{20}R^{21}$, CN, $NO_2$, $C_1$-$C_6$ alkyl and —$S(O)_2$—$R^{22}$;

$R^7$ is selected from the group consisting of hydrogen, halo, —O—$R^{20}$, —C(O)—$R^{20}$, —C(O)O—$R^{20}$, —$NR^{20}R^{21}$, —C(O)$NR^{20}R^{21}$, —C(S)$NR^{20}R^{21}$, —$NR^{23}C(O)NR^{20}R^{21}$, —$NR^{23}C(S)NR^{20}R^{21}$, —O—C(O)$NR^{20}R^{21}$, —$S(O)_2NR^{20}R^{21}$, —O—$S(O)_2NR^{20}R^{21}$, —$NR^{23}$—$S(O)_2NR^{20}R^{21}$, CN, $NO_2$, $C_1$-$C_6$ alkyl and —$S(O)_2$—$R^{22}$;
each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle; or $R^{20}$ and $R^{21}$ together with the atom attached thereto form a 5- to 7-membered heterocycle;
$R^{12}$ and $R^{22}$ are independently $C_1$-$C_6$ alkyl; and
==== represents a single bond or a double bond.

2. The compound of claim 1, or a tautomer, a pharmaceutically acceptable salt and/or a solvate thereof, wherein
a) $R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —C(O)O—$R^{10}$, —$NR^{10}R^{11}$, —C(O)$NR^{10}R^{11}$, —$NR^{13}C(O)NR^{10}R^{11}$, —O—C(O)$NR^{10}R^{11}$, —$NR^{13}$—$S(O)_2NR^{10}R^{11}$, CN, halo, and —$S(O)_2$—$R^2$; or
b) $R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —$NR^{10}R^{11}$, —$NR^{13}C(O)NR^{10}R^{11}$, —O—C(O)$NR^{10}R^{11}$, and —$NR^{13}$—$S(O)_2NR^{10}R^{11}$; or
c) $R^1$ is selected from the group consisting of hydrogen and 5- to 7-membered heterocycle optionally substituted with one or two $R^3$, wherein $R^3$ is independently selected from the group consisting of —O—$R^{10}$ and —O—C(O)$NR^{10}R^{11}$; or
d) $R^1$ is a 5- to 7-membered heterocycle substituted with one or two $R^3$, wherein $R^3$ is independently selected from the group consisting of —O—$R^{00}$ and —O—C(O)$NR^{10}R^{11}$.

3. The compound of claim 1, or a tautomer, a pharmaceutically acceptable salt and/or a solvate thereof, wherein $R^1$ is hydrogen or a 5- to 7-membered heterocycle.

4. The compound of claim 1, or a tautomer, a pharmaceutically acceptable salt and/or a solvate thereof, wherein
a) $R^6$ is selected from the group consisting of hydrogen, halo, —O—$R^{20}$, —C(O)—$R^{20}$, —C(O)O—$R^{20}$, —$NR^{20}R^{21}$, —$NR^{23}C(O)NR^{20}R^{21}$, —O—C(O)$NR^{20}R^{21}$, —$S(O)_2NR^{20}R^{21}$, CN, $C_1$-$C_6$ alkyl and —$S(O)_2$—$R^{22}$; or
b) $R^6$ is selected from the group consisting of hydrogen, halo, —C(O)—$R^{20}$, —C(O)O—$R^{20}$, —$S(O)_2NR^{20}R^{21}$, CN, and —$S(O)_2$—$R^{22}$; or
c) $R^6$ is selected from the group consisting of hydrogen, and —$S(O)_2$—$R^{22}$.

5. The compound of claim 1, or a tautomer, a pharmaceutically acceptable salt and/or a solvate thereof, wherein
a) $R^7$ is selected from the group consisting of hydrogen, halo, —C(O)—$R^{20}$, —C(O)O—$R^{20}$, —C(O)$NR^{20}R^{21}$, —$S(O)_2NR^{20}R^{21}$, CN, $NO_2$, and —$S(O)_2$—$R^{22}$; or
b) $R^7$ is selected from the group consisting of hydrogen, halo, —C(O)—$R^{20}$, —C(O)O—$R^{20}$, —C(O)$NR^{20}R^{21}$, and CN; or
c) $R^7$ is selected from the group consisting of hydrogen, and —C(O)$NR^{20}R^{21}$.

6. The compound of claim 1, or a tautomer, a pharmaceutically acceptable salt and/or a solvate thereof, wherein X is O.

7. The compound of claim 1, which is of Formula VI

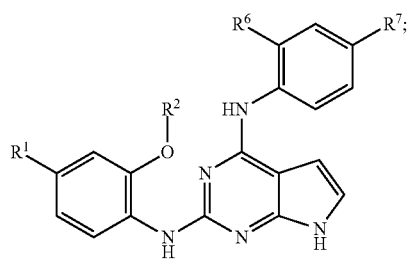

VI or a tautomer, a pharmaceutically acceptable salt and/or a solvate thereof, wherein $R^1$, $R^2$, $R^6$, and $R^7$ are as defined in claim 1.

8. The compound of claim 1, which is of Formula VII

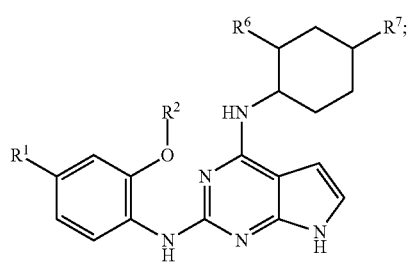

VII or a tautomer, a pharmaceutically acceptable salt and/or a solvate thereof.

9. The compound of claim 1, which is of Formula VIII

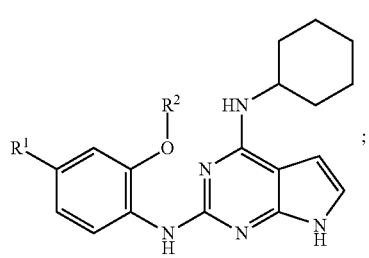

VIII or a tautomer, a pharmaceutically acceptable salt and/or a solvate thereof, wherein $R^1$ and $R^2$ are as defined in claim 1.

10. The compound of claim 1, or a tautomer, a pharmaceutically acceptable salt and/or a solvate thereof, wherein X is S or $SO_2$.

11. The compound of claim 1 selected from the group consisting of

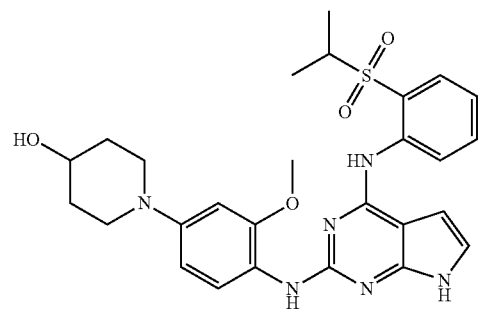

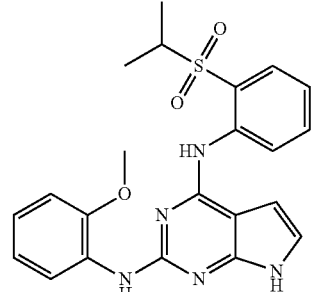

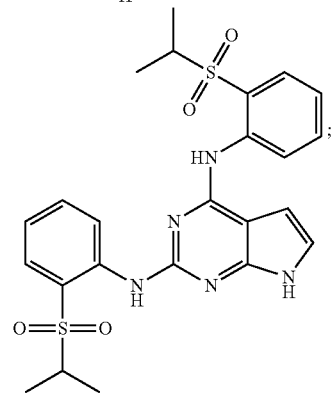

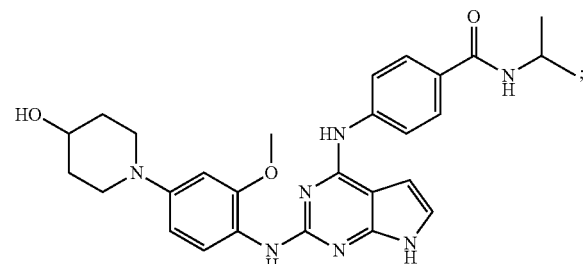

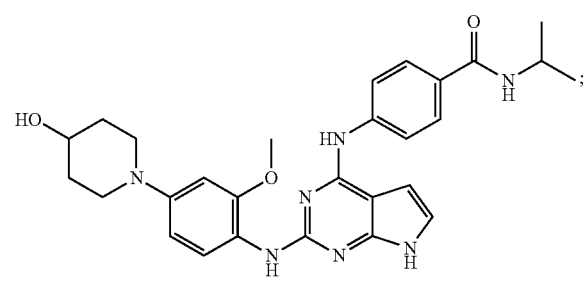

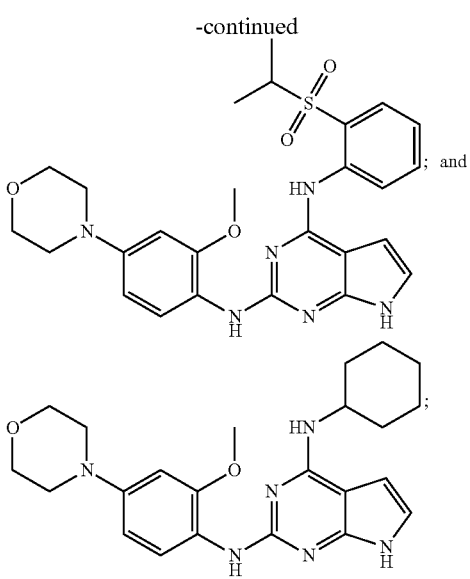

; and or a tautomer, a pharmaceutically acceptable salt and/or a solvate thereof.

12. A pharmaceutical composition comprising the compound of claim 1 and a carrier, optionally a pharmaceutically acceptable carrier.

13. A method of treating a disease mediated at least in part by protein kinase Mps1 in a patient in need thereof, which method comprising administering to the patient a therapeutically effective amount of a compound of Formula IV-A or V-A:

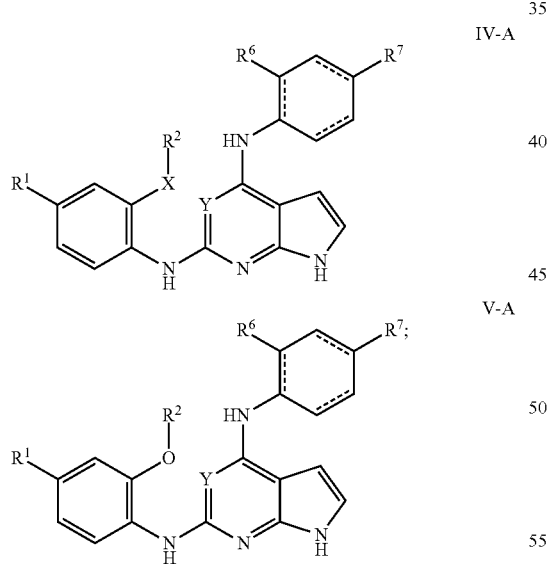

or a tautomer, a pharmaceutically acceptable salt and/or a solvate thereof;
wherein
X is O, S or $SO_2$;
Y is N;
$R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —C(O)O—$R^{10}$, —$NR^{10}R^{11}$, —C(O) $NR^{10}R^{11}$, —$C(S)NR^{10}R^{11}$, —$NR^{13}C(O)NR^{10}R^{11}$, —$NR^{13}C(S)NR^{10}R^{11}$, —O—$C(O)NR^{10}R^{11}$, —$S(O)_2 NR^{10}R^{11}$, —O—$S(O)_2NR^{10}R^{11}$, —$NR^{13}$—$S(O)_2 NR^{10}R^{11}$, CN, halo, $NO_2$, and —$S(O)_2$—$R^2$;

$R^2$ is selected from the group consisting of hydrogen, $C_1$-$C_3$ alkyl and $C_1$-$C_3$ haloalkyl; provided that when X is $SO_2$, or when $R^1$ is hydrogen, then $R^2$ is not hydrogen;

$R^6$ is selected from the group consisting of hydrogen, halo, —O—$R^{20}$, —C(O)—$R^{20}$, —C(O)O—$R^{20}$, —$NR^{20}R^{21}$, —$C(S)NR^{20}R^{21}$, —$NR^{23}C(O)NR^{20}R^{21}$, —$NR^{23}C(S)NR^{20}R^{21}$, —O—$C(O)NR^{20}R^{21}$, —$S(O)_2 NR^{20}R^{21}$, —O—$S(O)_2NR^{20}R^{21}$, —$NR^{23}$—$S(O)_2 NR^{20}R^{21}$, CN, $NO_2$, $C_1$-$C_6$ alkyl and —$S(O)_2$—$R^{22}$;

$R^7$ is selected from the group consisting of hydrogen, halo, —O—$R^{20}$, —C(O)—$R^{20}$, —C(O)O—$R^{20}$, —$NR^{20}R^{21}$, —$C(O)NR^{20}R^{21}$, —$C(S)NR^{20}R^{21}$, —$NR^{23}C(O)NR^{20}R^{21}$, —$NR^{23}C(S)NR^{20}R^{21}$, —O—$C(O)NR^{20}R^{21}$, —$S(O)_2NR^{20}R^{21}$, —O—$S(O)_2NR^{20}R^{21}$, —$NR^{23}$—$S(O)_2NR^{20}R^{21}$, CN, $NO_2$, $C_1$-$C_6$ alkyl and —$S(O)_2$—$R^{22}$;

each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle; or $R^{20}$ and $R^{21}$ together with the atom attached thereto form a 5- to 7-membered heterocycle;

$R^{12}$ and $R^{22}$ are independently $C_1$-$C_6$ alkyl; and
==== represents a single bond or a double bond;
wherein the disease is breast cancer or triple negative breast cancer.

14. A method of treating a patient in need of an inhibitor of protein kinase Mps1/TTK, which method comprises
a) determining the level of Mps1/TTK protein and/or mRNA in a cell of the patient; and administering a therapeutically effective amount of a compound of Formula IV-A or V-A or a tautomer, and/or a pharmaceutically acceptable salt and/or solvate thereof to the patient if the presence of Mps1/TTK protein and/or mRNA is detected, wherein the compound of Formula IV-A or V-A is:

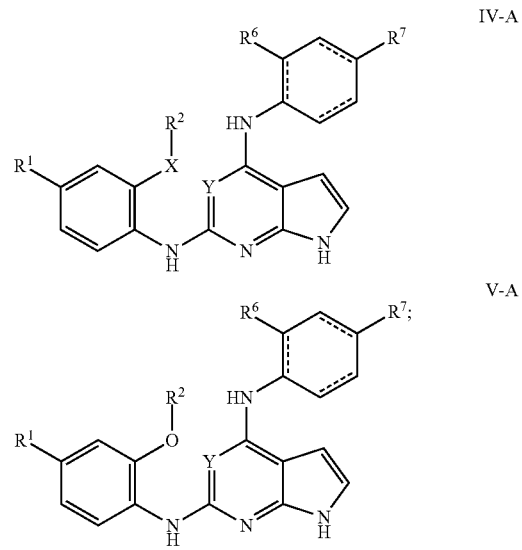

or a tautomer, a pharmaceutically acceptable salt and/or a solvate thereof;

wherein

X is O, S or $SO_2$;

Y is N;

$R^1$ is selected from the group consisting of hydrogen and 5- to 7-membered heterocycle optionally substituted with one or two oxo and/or $R^3$, wherein $R^3$ is independently selected from the group consisting of —O—$R^{10}$, —$NR^{10}C(O)R^{12}$, —$C(O)O-R^{10}$, —$NR^{10}R^{11}$, —$C(O)NR^{10}R^{11}$, —$C(S)NR^{10}R^{11}$, —$NR^{13}C(O)NR^{10}R^{11}$, —$NR^{13}C(S)NR^{10}R^{11}$, —O—$C(O)NR^{10}R^{11}$, —$S(O)_2NR^{10}R^{11}$, —O—$S(O)_2NR^{10}R^{11}$, —$NR^{13}$—$S(O)_2NR^{10}R^{11}$, CN, halo, $NO_2$, and —$S(O)_2$—$R^{12}$;

$R^2$ is selected from the group consisting of hydrogen, $C_1$-$C_3$ alkyl and $C_1$-$C_3$ haloalkyl; provided that when X is $SO_2$, or when $R^1$ is hydrogen, then $R^2$ is not hydrogen;

$R^6$ is selected from the group consisting of hydrogen, halo, —O—$R^{20}$, —C(O)—$R^{20}$, —C(O)O—$R^{20}$, —$NR^{20}R^{21}$, —$C(S)NR^{20}R^{21}$, —$NR^{23}C(O)NR^{20}R^{21}$, —$NR^{23}C(S)NR^{20}R^{21}$, —O—$C(O)NR^{20}R^{21}$, —$S(O)_2NR^{20}R^{21}$, —O—$S(O)_2NR^{20}R^{21}$, —$NR^{23}$—$S(O)_2NR^{20}R^{21}$, CN, $NO_2$, $C_1$-$C_6$ alkyl and —$S(O)_2$—$R^{22}$;

$R^7$ is selected from the group consisting of hydrogen, halo, —O—$R^{20}$, —C(O)—$R^{20}$, —C(O)O—$R^{20}$, —$NR^{20}R^{21}$, —$C(O)NR^{20}R^{21}$, —$C(S)NR^{20}R^{21}$, —$NR^{23}C(O)NR^{20}R^{21}$, —$NR^{23}C(S)NR^{20}R^{21}$, —O—C(O)$NR^{20}R^{21}$, —$S(O)_2NR^{20}R^{21}$, —O—$S(O)_2NR^{20}R^{21}$, —$NR^{23}$—$S(O)_2NR^{20}R^{21}$, CN, $NO_2$, $C_1$-$C_6$ alkyl and —$S(O)_2$—$R^{22}$;

each of $R^{10}$, $R^{11}$, $R^{13}$, $R^{20}$, $R^{21}$, and $R^{23}$ is independently hydrogen or $C_1$-$C_6$ alkyl; or $R^{10}$ and $R^{11}$ together with the atom attached thereto form a 5- to 7-membered heterocycle; or $R^{20}$ and $R^{21}$ together with the atom attached thereto form a 5- to 7-membered heterocycle;

$R^{12}$ and $R^{22}$ are independently $C_1$-$C_6$ alkyl; and

==== represents a single bond or a double bond;

wherein the patient is a breast cancer patient.

* * * * *

UNITED STATES PATENT AND TRADEMARK OFFICE
CERTIFICATE OF CORRECTION

PATENT NO. : 10,611,765 B2
APPLICATION NO. : 15/524606
DATED : April 7, 2020
INVENTOR(S) : Robert Brueggemeier et al.

Page 1 of 1

It is certified that error appears in the above-identified patent and that said Letters Patent is hereby corrected as shown below:

In the Specification

Column 1, Lines 18-23 replace the Government Support Clause with:
--This invention was made with government support under grant numbers TR001070, TR000090, RR025755, and GM077311 awarded by the National Institutes of Health. The government has certain rights in the invention.--

Signed and Sealed this
Sixth Day of October, 2020

Andrei Iancu
*Director of the United States Patent and Trademark Office*